US010059723B2

(12) United States Patent
Jacques et al.

(10) Patent No.: US 10,059,723 B2
(45) Date of Patent: Aug. 28, 2018

(54) HISTONE DEACETYLASE INHIBITORS

(71) Applicant: BIOMARIN PHARMACEUTICAL INC., Novato, CA (US)

(72) Inventors: Vincent Jacques, Somerville, MA (US); James R. Rusche, Framingham, MA (US); Norton P. Peet, North Andover, MA (US); Jasbir Singh, Naperville, IL (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 0 days.

(21) Appl. No.: 15/346,877

(22) Filed: Nov. 9, 2016

(65) Prior Publication Data

US 2017/0050984 A1 Feb. 23, 2017

Related U.S. Application Data

(62) Division of application No. 13/823,708, filed as application No. PCT/US2012/026874 on Feb. 28, 2012, now Pat. No. 9,540,395.

(60) Provisional application No. 61/447,416, filed on Feb. 28, 2011.

(51) Int. Cl.
*C07D 513/04* (2006.01)
*C07D 277/593* (2006.01)
*C07D 231/12* (2006.01)
*C07D 263/32* (2006.01)
*C07D 261/08* (2006.01)
*C07D 471/04* (2006.01)
*C07D 403/06* (2006.01)
*C07D 211/34* (2006.01)
*C07D 401/06* (2006.01)

(52) U.S. Cl.
CPC .......... *C07D 513/04* (2013.01); *C07D 211/34* (2013.01); *C07D 231/12* (2013.01); *C07D 261/08* (2013.01); *C07D 263/32* (2013.01); *C07D 277/593* (2013.01); *C07D 401/06* (2013.01); *C07D 403/06* (2013.01); *C07D 471/04* (2013.01)

(58) Field of Classification Search
CPC .................................................. C07D 513/04
USPC ......................................................... 514/210
See application file for complete search history.

(56) References Cited

U.S. PATENT DOCUMENTS

| 4,174,958 A | 11/1979 | Pilgram |
| 4,855,442 A | 8/1989 | Lee et al. |
| 6,518,268 B1 | 2/2003 | Chin et al. |
| 6,710,060 B2 | 3/2004 | Yamamoto et al. |
| 6,740,670 B2 | 5/2004 | Orchard et al. |
| 7,728,131 B2 | 6/2010 | Asaki et al. |
| 8,329,946 B2 | 12/2012 | Schreiber et al. |
| 8,957,066 B2 | 2/2015 | Jacques et al. |
| 9,512,143 B2 | 12/2016 | Jacques et al. |
| 9,540,395 B2 | 1/2017 | Jacques et al. |
| 2004/0002503 A1 | 1/2004 | Chang et al. |
| 2004/0029885 A1 | 2/2004 | Bauer et al. |
| 2004/0077690 A1 | 4/2004 | Zhu et al. |
| 2004/0106599 A1 | 6/2004 | Delorme et al. |
| 2004/0142859 A1 | 7/2004 | Steffan et al. |
| 2004/0142953 A1 | 7/2004 | Delorme et al. |
| 2004/0147569 A1 | 7/2004 | Suzuki et al. |
| 2005/0215601 A1 | 9/2005 | Aono et al. |
| 2005/0245518 A1 | 11/2005 | Delorme et al. |
| 2006/0166990 A1 | 7/2006 | Ottosen et al. |
| 2007/0049603 A1 | 3/2007 | Miknis et al. |
| 2007/0276011 A1 | 11/2007 | Muto et al. |
| 2009/0306077 A1 | 12/2009 | Mogi et al. |
| 2010/0056522 A1 | 3/2010 | Yoneda et al. |
| 2010/0063045 A1 | 3/2010 | Mogi et al. |
| 2010/0196502 A1 | 8/2010 | Kozikowski et al. |
| 2010/0298358 A1 | 11/2010 | Lu et al. |
| 2012/0094971 A1 | 4/2012 | Rusche et al. |
| 2013/0210899 A1 | 8/2013 | Wood |
| 2013/0317003 A1 | 11/2013 | Jacques et al. |
| 2014/0051680 A1 | 2/2014 | Jacques et al. |

FOREIGN PATENT DOCUMENTS

| CN | 1632700 A | 6/2005 |
| CN | 101648922 A | 2/2010 |
| EP | 1390491 A1 | 2/2004 |
| JP | 11269140 | 10/1999 |
| JP | 11269146 | 10/1999 |
| JP | 11302173 | 11/1999 |
| JP | 2000256194 A | 9/2000 |
| JP | 2003137866 A | 5/2003 |
| JP | 2004035485 A | 2/2004 |
| JP | 2007001885 A | 1/2007 |
| KR | 2010117391 | 7/2012 |
| WO | WO-00/035877 A1 | 6/2000 |
| WO | WO-01/038322 A1 | 5/2001 |
| WO | WO-02/18335 A1 | 3/2002 |
| WO | WO-02/090534 A1 | 11/2002 |
| WO | WO-03/011851 A2 | 2/2003 |
| WO | WO-03/013484 A2 | 2/2003 |

(Continued)

OTHER PUBLICATIONS

Alberini, Transcription Factors in Long-Term Memory and Synaptic Plasticity, Physiol. Rev., 89:121-45 (2009).

(Continued)

*Primary Examiner* — Taofiq A Solola

(74) *Attorney, Agent, or Firm* — Marshall, Gerstein & Borun LLP

(57) ABSTRACT

This invention relates to generally inhibiting histone deacetylase ("HDAC") enzymes (e.g., HDAC1, HDAC2, and HDAC3).

26 Claims, 1 Drawing Sheet

(56) References Cited

FOREIGN PATENT DOCUMENTS

| | | |
|---|---|---|
| WO | WO-03/024448 A2 | 3/2003 |
| WO | WO-03/29017 A1 | 4/2003 |
| WO | WO-03/076422 A1 | 9/2003 |
| WO | WO-03/087057 A1 | 10/2003 |
| WO | WO-03/092686 A1 | 11/2003 |
| WO | WO-2004/005513 A2 | 1/2004 |
| WO | WO-2004/035525 A1 | 4/2004 |
| WO | WO-2004/039318 A2 | 5/2004 |
| WO | WO-2004/041273 A1 | 5/2004 |
| WO | WO-2004/052838 A1 | 6/2004 |
| WO | WO-2004/058234 A2 | 7/2004 |
| WO | WO-2004/069133 A2 | 8/2004 |
| WO | WO-2004/069823 A1 | 8/2004 |
| WO | WO-2004/071400 A2 | 8/2004 |
| WO | WO-2004/072068 A1 | 8/2004 |
| WO | WO-2004/087693 A1 | 10/2004 |
| WO | WO-2005/002552 A2 | 1/2005 |
| WO | WO-2005/003127 A1 | 1/2005 |
| WO | WO-2005/030144 A2 | 4/2005 |
| WO | WO-2005/030704 A1 | 4/2005 |
| WO | WO-2005/030705 A1 | 4/2005 |
| WO | WO-2005/035551 A2 | 4/2005 |
| WO | WO-2005/055928 A2 | 6/2005 |
| WO | WO-2005/058803 A1 | 6/2005 |
| WO | WO-2005/087724 A2 | 9/2005 |
| WO | WO-2005/092889 A1 | 10/2005 |
| WO | WO-2005/092899 A1 | 10/2005 |
| WO | WO-2005/121073 A1 | 12/2005 |
| WO | WO-2006/001958 A2 | 1/2006 |
| WO | WO-2006/005955 A1 | 1/2006 |
| WO | WO-2006/014618 A2 | 2/2006 |
| WO | WO-2006/033943 A2 | 3/2006 |
| WO | WO-2006/062580 A1 | 6/2006 |
| WO | WO-2006/065703 A1 | 6/2006 |
| WO | WO-2006/066133 A2 | 6/2006 |
| WO | WO-2006/070192 A1 | 7/2006 |
| WO | WO-2006/097474 A1 | 9/2006 |
| WO | WO-2006/102760 A1 | 10/2006 |
| WO | WO-2006/104983 A1 | 10/2006 |
| WO | WO-2006/105979 A1 | 10/2006 |
| WO | WO-2006/115845 A1 | 11/2006 |
| WO | WO-2006/122319 A2 | 11/2006 |
| WO | WO-2007/002248 A2 | 1/2007 |
| WO | WO-2007/011626 A2 | 1/2007 |
| WO | WO-2007/022638 A1 | 3/2007 |
| WO | WO-2007/039403 A1 | 4/2007 |
| WO | WO-2007/039404 A1 | 4/2007 |
| WO | WO-2007/044565 A2 | 4/2007 |
| WO | WO-2007/045844 A1 | 4/2007 |
| WO | WO-2007/055942 A2 | 5/2007 |
| WO | WO-2007/058927 A1 | 5/2007 |
| WO | WO-2007/061880 A1 | 5/2007 |
| WO | WO-2007/082873 A1 | 7/2007 |
| WO | WO-2007/082874 A1 | 7/2007 |
| WO | WO-2007/082876 A1 | 7/2007 |
| WO | WO-2007/082878 A1 | 7/2007 |
| WO | WO-2007/082882 A1 | 7/2007 |
| WO | WO-2007/084390 A2 | 7/2007 |
| WO | WO-2007/087129 A2 | 8/2007 |
| WO | WO-2007/087130 A2 | 8/2007 |
| WO | WO-2007/100657 A2 | 9/2007 |
| WO | WO-2007/113289 A1 | 10/2007 |
| WO | WO-2007/118137 A1 | 10/2007 |
| WO | WO-2007/136605 A2 | 11/2007 |
| WO | WO-2008/006793 A1 | 1/2008 |
| WO | WO-2008/010985 A2 | 1/2008 |
| WO | WO-2008/033743 A1 | 3/2008 |
| WO | WO-2008/033747 A2 | 3/2008 |
| WO | WO-2008/074132 A1 | 6/2008 |
| WO | WO-2008/084218 A1 | 7/2008 |
| WO | WO-2008/089436 A2 | 7/2008 |
| WO | WO-2008/109994 A1 | 9/2008 |
| WO | WO-2008/112913 A1 | 9/2008 |
| WO | WO-2008/113255 A1 | 9/2008 |
| WO | WO-2008122115 A1 | 10/2008 |
| WO | WO-2009/002495 A1 | 12/2008 |
| WO | WO-2009/002534 A1 | 12/2008 |
| WO | WO-2009/004427 A2 | 1/2009 |
| WO | WO-2009/015237 A1 | 1/2009 |
| WO | WO-2009/020589 A1 | 2/2009 |
| WO | WO-2009/024825 A1 | 2/2009 |
| WO | WO-2009/025785 A2 | 2/2009 |
| WO | WO-2009/027746 A1 | 3/2009 |
| WO | WO-2009/033281 A1 | 3/2009 |
| WO | WO-2009/036057 A1 | 3/2009 |
| WO | WO-2009/037001 A2 | 3/2009 |
| WO | WO-2009/045440 A1 | 4/2009 |
| WO | WO-2009/053808 A2 | 4/2009 |
| WO | WO-2009/063054 A1 | 5/2009 |
| WO | WO-2009/079391 A1 | 6/2009 |
| WO | WO-2009/086012 A1 | 7/2009 |
| WO | WO-2009/112522 A1 | 9/2009 |
| WO | WO-2009/156484 A2 | 12/2009 |
| WO | WO-2010/009139 A2 | 1/2010 |
| WO | WO-2010/009155 A2 | 1/2010 |
| WO | WO-2010/009166 A1 | 1/2010 |
| WO | WO-2010/014611 A1 | 2/2010 |
| WO | WO-2010/028192 A1 | 3/2010 |
| WO | WO-2010/028213 A2 | 3/2010 |
| WO | WO-2010/031708 A2 | 3/2010 |
| WO | WO-2010/038081 A2 | 4/2010 |
| WO | WO-2010/043953 A2 | 4/2010 |
| WO | WO-2010/049182 A2 | 5/2010 |
| WO | WO-2010/094678 A1 | 8/2010 |
| WO | WO-2010/126811 A1 | 11/2010 |
| WO | WO-2010/126851 A1 | 11/2010 |
| WO | WO-2010/127152 A2 | 11/2010 |
| WO | WO-2010/131922 A2 | 11/2010 |
| WO | WO-2010/144371 A1 | 12/2010 |
| WO | WO-2010/144378 A2 | 12/2010 |
| WO | WO-2012/016081 A2 | 2/2012 |
| WO | WO-2012/118782 A1 | 9/2012 |
| WO | WO-2013/011384 A1 | 1/2013 |
| WO | WO-2013/113841 A1 | 8/2013 |

OTHER PUBLICATIONS

Andrews et al., Design and campaign synthesis of piperidine- and thiazole-based histone deacetylase inhibitors, Bioorg. Med. Chem. Lett., 18(8):2580-4 (2008).

Archin et al., Administration of vorinostat disrupts HIV-1 latency in patients on antiretroviral therapy, Nature, 487(7408):482-5 (2012).

Ashton et al., New Low-Density Lipoprotein Receptor Upregulators Acting via a Novel Mechanism, J. Med. Chem., 39(17):3343-56 (1996).

Bayomi, Synthesis and ring transformation of pyrrolo[2,3-d][1,3]oxazine to pyrrolo[2,3-d]pyrimidines, Arch. Pharm Res., 13(1):97-100 (1990).

Bayomi, Synthesis and ring transformation of pyrrolo[2,3-d][1,3]oxazine to pyrrolo[2,3-d]pyrimidines, J. Chin. Chem. Soc., 39(1):101-4 (1992).

Blackwell et al., Decoding products of diversity pathways from stock solutions derived from single polymeric macrobeads, Angew. Chem. Int. Ed., 40(18):3421-5 (2001).

Blazkovaj et al., Effect of histone deacetylase inhibitors on Hiv production in latently infected, resting CD4(+) T cells from infected individuals receiving effective antiretroviral therapy, J. Infect. Dis., 206(5):765-9 (2012).

Boev et al., Synthesis of new polydentate tweezers ligands of amido-amine type, Russ. J. Org. Chem., 43(2):297-304 (2007).

Campuzano et al., Friedreich's ataxia: autosomal recessive disease caused by an intronic GAA triplet repeat expansion, Science, 271:1423-7 (1996).

CAS Science IP, Search Report dated Dec. 17, 2010, 125 pages.
CAS Science IP, Search Report dated Dec. 17, 2010, 97 pages.
CAS Science IP, Search Report dated Dec. 20, 2010, 284 pages.
CAS Science IP, Search Report dated Dec. 22, 2010, 860 pages.
Charles et al., Synthesis of substituted benzamides and benzimidazoles as anthelmintic and antimicrobial agents, Pharmazie, 37(6):413-15 (1982).

(56) References Cited

OTHER PUBLICATIONS

Charrier et al., Antiproliferative activities of a library of hybrids between indanones and HDAC inhibitor SAHA and MS-275 analogues, Bioorg. Med. Chem. Lett., 17(22):6142-6 (2007).
Charton et al., Synthesis and biological evaluation of benzimidazole derivatives as potent AMP-activated protein kinase activators, Bioorg. Med. Chem., 14(13):4490-518 (2006).
Chen et al., Discovering benzamide derivatives as glycogen phosphorylase inhibitors and their binding site at the enzyme, Bioorg. Med. Chem., 15(21):6763-74 (2007).
Chen et al., Pyrrolopyridazine MEK inhibitors, Bioorg. Med. Chem. Lett., 16(3):628-32 (2006).
Chou et al., Pimelic Diphenylamide 106 is a Slow, Tight-binding Inhibitor of Class I Histone Deacetylases, J. Biol. Chem., 283(51):35402-9 (2008).
Coxon et al., Structure of the reaction product of 4-hydroxy-2,3-dioxo-4-phenylbutanoic acid 1,4-lactone with o-phenylenediamine, Carbohydrate Res., 142(1):1-10 (1985).
Dahn et al., Reductones and tricarbonyl compds. XXI. Reactions of dehydroascorbic acid and of other 2,3-dioxobutyrolactones with o-phenylenediamine, Helvetica. Chimica. Acta., 47(7):1860-70 (1964). (English Summary).
Dessalew, QSAR study on aminophenylbenzamides and acrylamides as histone deacetylase inhibitors: an insight into the structural basis of antiproliferative activity, Med Chem Res., 16(719):449-60 (2007).
Dokmanovic et al., Histone Deacetylase Inhibitors: Overview and Perspectives, Mol. Cancer Res., 5:981-9 (2007).
El Ashry et al., Reaction of dehydro-L-ascorbic acid analogs with o-phenylenediamine, Carbohydrate Res., 153(1):146-9 (1986).
Frechette et al., 4-(Heteroarylaminomethyl)-N-(2-aminophenyl)-benzamides and their analogs as a novel class of histone deacetylase inhibitors, Bioorg. Med. Chem. Lett., 18(4):1502-6 9 (2008).
Gilley et al., 2-Nitrophenyl Isocyanide as a Versatile Convertible Isocyanide: Rapid Access to a Fused y-Lactam13-Lactone Bicycle, J. Org. Chem., 73(11):4198-204 (2008).
Goebel et al., Characterization of new PPARy agonists: analysis of telmisartan's structural components, Chem. Med. Chem., 4(3):445-56 (2009).
Guan et al., HDAC2 negatively regulates memory formation and synaptic plasticity, Nature, 459(7243):55-60 (2009).
Habib et al., Synthetic approaches and biological evaluation of some new sulfonate ester-containing quinazoline derivatives as potentially active antimicrobial agents, Bollettino Chimico Farmaceutico, 134(4):209-15 (1995).
Hamblett et al., The discovery of 6-amino nicotinamides as potent and selective histone deacetylase inhibitors, Bioorg. Med. Chem. Lett., 17(19):5300-5309 (2007).
Hasegawa et al., Novel Naphthalene Derivatives as Inhibitors of Human Immunoglobulin E Antibody Production, J. Med. Chem., 40(4):395-407 (1997).
Hassan et al., Condensed pyrroles: N1-benzyl-2,5,6-trimethylpyrrolo[2,3-41,3-oxazin-4-ones and N1-benzy1-2,5,6-trimethy1-3-substituted-pyrrolo[2,3-d]pyrimidin-4-ones, Indian J. Chem. Section B: Org. Chem. Incl. Med. Chem., 39B(10):764-8 (2000).
Heidebrecht et al., Exploring the pharmacokinetic properties of phosphorus-containing selective HDAC 1 and 2 inhibitors (SHI-1:2), Bioorg. Med. Chem. Lett., 19(7):2053-8 (2009).
Herman et al., Histone Deacetylase Inhibitors Reverse Gene Silencing in Friedreich's Ataxia, Nature Chem. Biol., 2(10):551-8 (2006).
Huang et al., N-(2-Aminophenyl)-2-anilinobenzamide, Acta Crystallographica, Section E: Struct. Rept. Online, 65(5):o1108, (2009).
Hubbs et al., Amino acid derivatives as histone deacetylase inhibitors, Bioorg. Med. Chem. Lett., 18(1):34-8 (2008).
Ismail et al., Behavior of 2-substituted 6,8-dibromo-3,1-benzoxazin-4-ones towards o-phenylenediamine and anthranilic acid; a case of unusual cleavage of 6,8-dibromo-2-methy1-3,1-benzoxazin-4-one, Tetrahedron, 44(12):3757-60 (1988).

Jazouli et al., A short and efficient synthesis of 2'-deoxybenzo- and pyridoimidazole C-nucleosides, Tetrahedron Lett., 44(31):5807-10 (2003).
Katayev et al., Anion binding by pyrrole-pyridine-based macrocyclic polyamides, Supramolecular Chem., 20(7):619-24 (2008).
Katayev et al., Bipyrrole- and Dipyrromethane-Based Amido-imine Hybrid Macrocycles. New Receptors for Oxoanions, J. Org. Chem., 72(8):2886-96 (2007).
Katayev et al., Expanding sapphyrin: towards selective phosphate binding, Chem. Eur. J., 14(29):9065-73 (2008).
Katritzky et al., Azlactones as Polymer Components and Intermediates, J Polymer Sci.: Part A: Polymer Chem. 27:1781-90 (1989).
Kattar et al., Parallel medicinal chemistry approaches to selective HDAC1/HDAC2 inhibitor (SHI-1:2) optimization, Bioorg. Med. Chem. Lett., 19(4), 1168-72 (2009).
Khan et al., Determination of the class and isoform selectivity of small-molecule histone deacetylas, Biochem. J., 409(2):581-9 (2008).
Kitagawa et al., Effects of a novel histone deacetylase inhibitor, N-(2-aminophenyl) benzamide, on a reversible hypertrophy induced by isoproterenol in in situ rat hearts, J. Pharmacological Sci., 104(2)1 67-175 (2007).
Kiyokawa et al., New orally bioavailable 2-aminobenzamide-type histone deacetylase inhibitor possessing a (2-hydroxyethyl)(4-(thiophen-2-yl)benzyl)amino group, Bioorg. Med. Chem., 18(11):3925-33 (2010).
Korshak et al., The Effect of Chemical Defects in Macromolecules on the Thermal Stability of Pyrrones, Acad. Sci. USSR, 200:865-8 (1971).
Kuroda et al., Further Development of a Robust Workup Process for Solution-Phase High-Throughput Library Synthesis to Address Environmental and Sample Tracking Issues, Bioorg. Med. Chem., 8(4):505-12 (2006).
Li et al., Design, synthesis and bioevaluation of novel benzamides derivatives as HDAC inhibitors, Bioorg. Med. Chem. Lett., 23(1):179-82 (2013).
Lu et al., Zn2+-Chelating, Motif-Tethered, Short-Chain Fatty Acids as a Novel Class of Histone Deacetylase Inhibitors, J. Med. Chem., 47(2):467-74 (2004).
Mahboobi et al., Design of Chimeric Histone Deacetylase- and Tyrosine Kinase-Inhibitors: A Series of Imatinib Hybrides as Potent Inhibitors of Wild-Type and Mutant BCR-ABL, PDGF-Rb, and Histone Deacetylases, J. Med. Chem., 52(8):2265-79 (2009).
Mai et al., Novel uracil-based 2-aminoanilide and 2-aminoanilide-like derivatives: Histone deacetylase inhibition and in-cell activities, Bioorg. Med. Chem. Lett., 18(8):2530-5 (2008).
Malvaez et al., HDAC3-selective inhibitor enhances extinction of cocaine-seeking behavior in a persistent manner, 110(7):2647-52 Prot. Natl. Acad. Sci. USA, (2013).
McQuown et al., HDAC3 Is a Critical Negative Regulator of Long-Term Memory Formation, J. Neurosci., 31(2):764-74 (2011).
Methot et al., Exploration of the internal cavity of histone deacetylase (HDAC) with selective HDAC1/HDAC2 inhibitors (SHI-1:2), Bioorg. Med. Chem. Lett., 18(3):973-8 (2008).
Methot et al., SAR profiles of spirocyclic nicotinamide derived selective HDAC1/HDAC2 inhibitors (SHI-1:2), Bioorg. Med. Chem. Lett., 18(23):6104-9 (2008).
Moradei et al., Novel Aminophenyl Benzamide-Type Histone Deacetylase Inhibitors with Enhanced Potency and Selectivity, J Med Chem., 50(23):5543-6 (2007).
Moradei et al., Substituted N-(2-aminophenyl)-benzamides, (E)-N-(2-aminophenyl)-acrylamides and their analogues: Novel classes of histone deacetylase inhibitors, Bioorg. Med. Chem. Lett., 16(15):4048-52 (2006).
Nagaoka et al., Synthesis and cancer antiproliferative activity of new histone deacetylase inhibitors: hydrophilic hydroxamates and 2-aminobenzamide-containing derivatives, European J. Med. Chem., 41(6):697-708 (2006).
Oliva et al., Chromogenic Charge Transfer Cleft-Type Tetrahydrobenzoxanthene Enantioselective Receptors for Dinitrobenzoylamino Acids, J. Org. Chem., 69(20):6883-5 (2004).

(56) References Cited

OTHER PUBLICATIONS

Paquin et al., Design and synthesis of 4-[(s-triazin-2-ylamino)methyl]-N-(2-aminophenyl)benzamides and their analogs as a novel class of histone deacetylase inhibitors, Bioorg. Med. Chem Lett., 18(3):1067-71 (2008).
Pigro et al., Readily available carbohydrate-derived imines and amides as chiral ligands for asymmetric catalysis, Tetrahedron, 58(27):5459-5466 (2002).
Rabilloud et al., Condensation reactions between o-phenylenediamine and 2-substituted 1,3-benzoxazin-4-ones, Bulletin de la Societe Chimique de France, (11-12, Pt. 2):2682-6 (1975). (English Summary).
Raeppel et al., SAR and biological evaluation of analogues of a small molecule histone deacetylase inhibitor N-(2-aminophenyl)-44(4-(pyridin-3-yl)pyrimidin-2-ylamino)methyl)benzamide (MGCD0103), Bioorg. Med. Chem. Lett., 19(3):644-9 (2009).
Rai et al., HDAC Inhibitors Correct Frataxin Deficiency in a Friedreich Ataxia Mouse Mode, Plos ONE, Apr. 9, 3(4):1-8 (2008).
Reddy et al., Synthesis of chiral benzimidazole-pyrrolidine derivatives and their application in organocatalytic aldol and Michael addition reactions, Synth. Comm., 37(24):4289-99 (2007).
Sagara et al., Identification of a Novel 4-Aminomethylpiperidine Class of M3 Muscarinic Receptor Antagonists and Structural Insight into Their M3 Selectivity, J Med Chem., 49(19):5653-63 (2006).
Salisbury et al., Optimization of Activity-Based Probes for Proteomic Profiling of Histone Deacetylase Complexes, J Am Chem Soc., 130(7):2184-2194 (2008).
Savarino et al., Shock and kill' effects of class I-selective histone deacetylase inhibitors in combination with the glutathione synthesis inhibitor buthionine sulfoximine in cell line models for HIV-1 quiescence, Retrovirology, 6:52, (2009).
Siliphaivanh et al., Design of novel histone deacetylase inhibitors, Bioorg. Med. Chem. Lett., 17(16):4619-24 (2007).
Stefanko et al., Modulation of long-term memory for object recognition via HDAC inhibition, Proc. Natl. Acad. Sci. USA, 106(23):9447-52 (2009).
Supplementary European Search Report, Appl. No. 09812248.4 dated Aug. 20, 2012.
Thomas et al., The HDAC inhibitor 4b ameliorates the disease phenotype and transcriptional abnormalities in Huntington's disease transgenic mice, Proc. Natl. Acad. Sci. USA, 105(40):15564-9 (2008).
Tsujimoto et al., Condensation of o-phenylenediamine with dehydro-L-ascorbic acid derivatives and analogs, Carbohydrate Res., 138(1):148-52 (1985).
Turitsyna et al., Azomethine dyes. II. Indoaniline dyes, derivatives of 1-hydroxy-2-naphthanilide, Zhurnal Obshchei Khimii, 26:2546-54 (1956). (English Summary).
Vaisburg et al., N-(2-Amino-phenyl)-4-(heteroarylmethyl)-benzamides as new histone deacetylase inhibitors, Bioorg. Med. Chem. Lett., 17(24):6729-33 (2007).
Valente et al., Pyrrole-Based Hydroxamates and 2-Aminoanilides: Histone Deacetylase Inhibition and Cellular Activities, Chem. Med. Chem., 4(9):1411-5 (2009).
Vannini et al., Substrate binding to histone deacetylases as shown by the crystal structure of the HDAC8-substrate complex, EMBO Reports, 8:879-84 (2007).
Vattipalli et al., Synthesis and13-adrenergic blocking activity of naphthyloxypropylamines, Indian J. Chem. Sect. B: Org. Chem. Incl. Med. Chem., 47B(10):1587-90 (2008).
Wagner, 3-Alkyl-3-ally1-2,4-diketo-1,2,4,5-tetrahydro-3H-benzo-1,5-diazepines and their hydration products, Roczniki Chemii, 48(7-8):1289-96 (1974).
Wang et al., Immunomodulatory effects of deacetylase inhibitors: therapeutic targeting of FOXP3+ regulatory T cells, Nat. Rev. Drug Disc., 8:969-81 (2009).
Wang et al., Monoacylation of unprotected symmetrical diamines with resin-bound benzoic acids, Tetrahedron Lett., 45(35):6645-8 (2004).
Wang et al., N-Hydroxy-1,2-disubstituted-1H-benzimidazol-5-yl acrylamides as novel histone deacetylase inhibitors: Design, synthesis, SAR studies, and in vivo antitumor activity, Bioorg. Med. Chem. Lett., 19(5)1 403-8 (2009).
Wang et al., Screening on in vitro anti-tumor activities of novel synthetic compounds targeting histone deacetylase, Jiefangjun Yaoxue Xuebao, 25(6):482-5 (2009). (English Abstract).
Witter et al., Optimization of biaryl Selective HDAC1&2 Inhibitors (SHI-1:2), Bioorg. Med. Chem. Lett., 18(2):726-731 (2008).
Zhu et al., Investigation on the isoform selectivity of histone deacetylase inhibitors using chemical feature based pharmacophore and docking approaches, European J. Med. Chem., 45(5):1777-91 (2010).
Farag et al. Studies with polyfunctionally substituted heterocycles. Novel synthesis of pyrazolyl-1,2,4-triazoles and pyrazolo[5,1-c][1,2,4]triazines, J Chemical Res. Synopses, 1994, (1), 10-11.

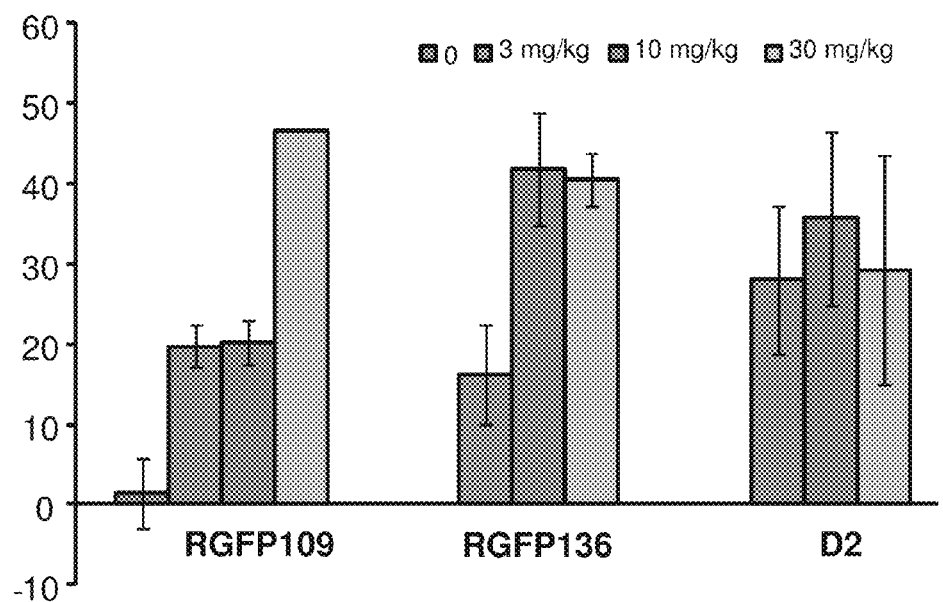

HISTONE DEACETYLASE INHIBITORS

CROSS REFERENCE TO RELATED APPLICATIONS

This application claims the benefit of U.S. Provisional Application No. 61/447,416, filed on Feb. 28, 2011, which is incorporated herein by reference in its entirety.

TECHNICAL FIELD

This invention relates to generally inhibiting histone deacetylase ("HDAC") enzymes (e.g., HDAC1, HDAC2, and HDAC3).

BACKGROUND

To date, 18 HDACs have been identified in humans and there is increasing evidence that the 18 histone deacetylases (HDAC) in humans are not redundant in function. HDACs are classified into three main groups based on their homology to yeast proteins. Class I includes HDAC1, HDAC2, HDAC3, and HDAC8 and have homology to yeast RPD3. HDAC4, HDAC5, HDAC7, and HDAC9 belong to class IIa and have homology to yeast HDAC1. HDAC6 and HDAC10 contain two catalytic sites and are classified as class IIb, whereas HDAC11 has conserved residues in its catalytic center that are shared by both class I and class II deacetylases and is placed in class IV. These HDACs contain zinc in their catalytic site and are inhibited by compounds like trichostatin A (TSA) and vorinostat [suberoylanilide hydroxamic acid (SAHA)]. Class III HDACs are known as sirtuins. They have homology to yeast Sir2, require $NAD^+$ as cofactor, and do not contain zinc in the catalytic site. In general, HDAC inhibitors of zinc-dependent HDACs include a Zn-binding group, as well as a surface recognition domain.

HDACs are involved in the regulation of a number of cellular processes. Histone acetyltransferases (HATs) and HDACs acetylate and deacetylate lysine residues on the N termini of histone proteins thereby affecting transcriptional activity. They have also been shown to regulate post-translational acetylation of at least 50 non-histone proteins such as $\alpha$-tubulin (see for example Kahn, N et al Biochem J 409 (2008) 581, Dokmanovic, M et al Mol Cancer Res 5 (2007) 981).

Altering gene expression through chromatin modification can be accomplished by inhibiting histone deacetylase (HDAC) enzymes. There is evidence that histone acetylation and deacetylation are mechanisms by which transcriptional regulation in a cell—a major event in cell differentiation, proliferation, and apoptosis—is achieved. It has been hypothesized that these effects occur through changes in the structure of chromatin by altering the affinity of histone proteins for coiled DNA in the nucleosome. Hypoacetylation of histone proteins is believed to increase the interaction of the histone with the DNA phosphate backbone. Tighter binding between the histone protein and DNA can render the DNA inaccessible to transcriptional regulatory elements and machinery. HDACs have been shown to catalyze the removal of acetyl groups from the $\epsilon$-amino groups of lysine residues present within the N-terminal extension of core histones, thereby leading to hypoacetylation of the histones and blocking of the transcriptional machinery and regulatory elements.

Inhibition of HDAC, therefore can lead to histone deacetylase-mediated transcriptional derepression of tumor suppressor genes. For example, cells treated in culture with HDAC inhibitors have shown a consistent induction of the kinase inhibitor p21, which plays an important role in cell cycle arrest. HDAC inhibitors are thought to increase the rate of transcription of p21 by propagating the hyperacetylated state of histones in the region of the p21 gene, thereby making the gene accessible to transcriptional machinery. Further, non-histone proteins involved in the regulation of cell death and cell-cycle also undergo lysine acetylation and deacetylation by HDACs and histone acetyl transferase (HATs).

This evidence supports the use of HDAC inhibitors in treating various types of cancers. For example, vorinostat (suberoylanilide hydroxamic acid (SAHA)) has been approved by the FDA to treat cutaneous T-cell lymphoma and is being investigated for the treatment of solid and hematological tumors. Further, other HDAC inhibitors are in development for the treatment of acute myelogenous leukemia, Hodgkin's disease, myelodysplastic syndromes and solid tumor cancers.

HDAC inhibitors have also been shown to inhibit pro-inflammatory cytokines, such as those involved in autoimmune and inflammatory disorders (e.g. TNF-$\alpha$). For example, the HDAC inhibitor MS275 was shown to slow disease progression and joint destruction in collagen-induced arthritis in rat and mouse models. Other HDAC inhibitors have been shown to have efficacy in treating or ameliorating inflammatory disorders or conditions in in vivo models or tests for disorders such as Crohn's disease, colitis, and airway inflammation and hyper-responsiveness. HDAC inhibitors have also been shown to ameliorate spinal cord inflammation, demyelination, and neuronal and axonal loss in experimental autoimmune encephalomyelitis (see for example Wanf L et al, Nat Rev Drug Disc 8 (2009) 969).

Triplet repeat expansion in genomic DNA is associated with many neurological conditions (e.g., neurodegenerative and neuromuscular diseases) including myotonic dystrophy, spinal muscular atrophy, fragile X syndrome, Huntington's disease, spinocerebellar ataxias, amyotrophic lateral sclerosis, Kennedy's disease, spinal and bulbar muscular atrophy, Friedreich's ataxia and Alzheimer's disease. Triplet repeat expansion may cause disease by altering gene expression. For example, in Huntington's disease, spinocerebellar ataxias, fragile X syndrome, and myotonic dystrophy, expanded repeats lead to gene silencing. In Friedreich's ataxia, the DNA abnormality found in 98% of FRDA patients is an unstable hyper-expansion of a GAA triplet repeat in the first intron of the frataxin gene (see Campuzano et al., Science 271:1423 (1996)), which leads to frataxin insufficiency resulting in a progressive spinocerebellar neurodegeneration. Since they can affect transcription and potentially correct transcriptional dysregulation, HDAC inhibitors have been tested and have been shown to positively affect neurodegenerative diseases (see Herman D et al, Nat Chem Bio 2 551 (2006) for Friedreich's ataxia, Thomas E A et al, Proc Natl Acad Sci USA 105 15564 (2008) for Huntington's disease).

HDAC inhibitors may also play a role in cognition-related conditions and diseases. It has indeed become increasingly evident that transcription is likely a key element for long-term memory processes (Alberini C M, Physiol Rev 89 121 (2009)) thus highlighting another role for CNS-penetrant HDAC inhibitors. Although studies have shown that treatment with non-specific HDAC inhibitors such as sodium butyrate can lead to long-term memory formation (Stefanko D P et al, Proc Natl Acad Sci USA 106 9447 (2009)), little is known about the role of specific isoforms. A limited number of studies have shown that, within class I HDACs, main target of sodium butyrate, the prototypical inhibitor used in cognition studies, HDAC2 (Guan J-S et al, Nature 459 55 (2009)) and HDAC3 (McQuown S C et al, J Neurosci 31 764 (2011)) have been shown to regulate memory processes and as such are interesting targets for memory enhancement or extinction in memory-affecting conditions such as, but not limited to, Alzheimer's disease, post-traumatic stress disorder or drug addiction.

SUMMARY

In one aspect, a compound of the formula (I) is featured:

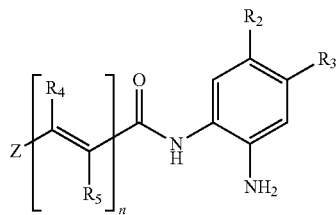

(I)

wherein n=0 or 1;
I. when n=1, Z is $R_1$—X—Ar/Het wherein:
Ar/Het is:
(i) a 5 membered heteroaryl selected from the group consisting of pyrazolyl, thiazolyl, oxazolyl, imidazolyl, thienyl, furanyl, isoxazolyl, isothiazolyl, thiadiazolyl, oxadiazolyl, and 1,2,4-triazolyl (in some embodiments, the definition of Ar/Het can further include 3,5-dimethylpyrazolyl); or
(ii) a bicyclic 8-, 9-, or 10-membered heteroaryl selected from the group consisting of benzofuranyl, benzothienyl, benzothiazolyl, indolyl, indazolyl, quinolonyl, naphtyridinyl, indolizinyl, pyrrolopyrimidinyl, pyrazolopyridinyl, imidazopyridinyl, imidazopyridazinyl, triazolopyridinyl, imidazothiazolyl, imidazooxazolyl, triazolothiazolyl, and triazolooxazolyl;
X is:
(i) —Y—[C($R^a$)$_2$]$_a$-A-[C($R^b$)$_2$]$_b$—B—;
wherein:
Y is bond, $CR^c$=$CR^d$, O, $NR^e$, or $S(O)_m$;
each of A and B is, independently, a bond, O, $NR^f$, or $S(O)_m$;
a is 1-3 (e.g., 1 or 2, e.g., 1);
b is 0-3 (e.g., 0, or other than 0, e.g., 1; or 2 or 3);
m is 0-2;
  each occurrence of $R^a$ and $R^b$ is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy, C1-C6 fluoroalkoxy, and cyano; or
  one or more of the following can apply with respect to $R^a$ and $R^b$:
  any two $R^a$, together with the carbons to which each is attached, together form C3-C6 cycloalkyl or heterocyclyl including 3-6 ring atoms, in which one of the heterocyclyl ring atoms is selected from O; S(O)m and $NR^g$; in these embodiments, any remaining occurrences of $R^a$ and any occurrence of $R^b$ are each independently defined according to any one or more of the preceding or following definitions pertaining to $R^a$ and $R^b$; or
  one $R^a$ and one $R^b$, together with the carbons to which each is attached, form C3-C6 cycloalkyl or heterocyclyl including 3-6 ring atoms, in which one of the heterocyclyl ring atoms is selected from O; S(O)m and $NR^g$; in these embodiments, the other $R^a$, the other $R^b$, and any other remaining occurrences of $R^a$ and $R^b$ are each independently defined according to any one or more of the preceding or following definitions pertaining to $R^a$ and $R^b$; or
  any two $R^b$, together with the carbons to which each is attached, form C3-C6 cycloalkyl or heterocyclyl including 3-6 ring atoms, in which one of the ring atoms is selected from O; S(O)m and $NR^g$; in these embodiments, each occurrence of $R^a$ and any other remaining occurrences of $R^b$ are each independently defined according to any one or more of the preceding or following definitions pertaining to $R^a$ and $R^b$;
  each of $R^c$ and $R^d$ is, independently, selected from H, F, OH, C1-C6 alkyl, C3-C5 cycloalkyl, $NH_2$, OCO—(C1-C6 alkyl), OCO—(C3-C5 cycloalkyl), C1-C6 alkoxy, C1-C6 fluoroalkoxy, and cyano;
  or $R^c$ and $R^d$, together with the carbons to which each is attached form a C5-C7 cycloalkyl or heterocyclyl including 3-6 ring atoms, in which from 1-2 of the heterocyclyl ring atoms is/are independently selected from O; $S(O)_m$ and $NR^{g'}$;
  each occurrence of $R^e$, $R^f$, $R^g$ and $R^{g'}$ is independently selected from H, C1-C6 alkyl, —C(=O)H, —C(=O)$R^h$, C(=O)O(C1-C6 alkyl), C(=O)N($R^i$)$_2$, $SO_2$—$R^h$, wherein $R^h$ is selected from C1-C6 alkyl, $CH_2$-(heteroaryl including 5-10 ring atoms), $CH_2$—(C6-C10 aryl), and C6-C10 aryl; and each occurrence of $R^i$ is independently selected from H, C1-C6 alkyl, $CH_2$-(heteroaryl including 5-10 ring atoms), $CH_2$—(C6-C10 aryl), and C6-C10 aryl (in embodiments, the aryl and heteroaryl portion in $R^h$ and $R^i$ can be optionally substituted, e.g., with one or more independently selected substituents such as F, C1-C6 alkyl, fluoro C1-C6 alkyl, C3-C6 cycloalkyl, C1-C6 alkoxy, C1-C6 fluoroalkoxy, or cyano);
further wherein:
(a) when each of A and B is a bond, and b is 0, then X has the following formula: —Y—[C($R^a$)$_2$]$_a$—;
(b) when b is 0 or 1 (e.g., 0), then A and B cannot both be heteroatoms (i.e., as defined in O, $NR^e$, or $S(O)_m$); and
(c) when A or B serves as the point of connection of X to Ar/Het, and the Ar/Het is linked to X via a nitrogen ring atom in Ar/Het, then the A or B connector cannot be a heteroatom (i.e., as defined in O, $NR^e$, or $S(O)_m$);
or X is:
(ii) direct bond; or
(iii) C=O, C($R^j$)$_2$—C(=O), or C(=O)—C($R^j$)$_2$, $SO_2$—$NR^k$, $NR^k$—$SO_2$, C(=O)$NR^k$ and $NR^k$—C(=O); wherein:
each occurrence of $R^j$ is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy, C1-C6 fluoroalkoxy, and cyano;
or $R^j$—C—$R^j$ together form C3-C6 cycloalkyl or heterocyclyl including 3-6 ring atoms, in which one of the heterocyclyl ring atoms is selected from O; S(O)m and $NR^{j'}$;
each occurrence of $R^{j'}$ and $R^k$ is independently selected from H, C1-C6 alkyl, —C(=O)H, —C(=O)$R^m$, C(=O)O(C1-C6 alkyl), C(=O)N($R^n$)$_2$, and $SO_2$—$R^m$, wherein $R^m$ is selected from C1-C6 alkyl, $CH_2$-heteroaryl, $CH_2$-aryl, and aryl; and each occurrence of $R^n$ is independently selected from H, C1-C6 alkyl, $CH_2$-

(heteroaryl including 5-10 ring atoms), $CH_2$—(C6-C10 aryl), and C6-C10 aryl (in embodiments, the aryl and heteroaryl portion in $R'''$ and $R''$ can be optionally substituted, e.g., with one or more independently selected substituents such as F, C1-C6 alkyl, fluoro C1-C6 alkyl, C3-C6 cycloalkyl, C1-C6 alkoxy, C1-C6 fluoroalkoxy, or cyano);

each of R4 and R5 is, independently, selected from H, C1-C6 alkyl and F;

R1 is:

(i) hydrogen; or (ii) C6-C10 aryl, which is optionally substituted with from 1-3 $R°$; or (iii) monocyclic or bicyclic heteroaryl including from 5-10 ring atoms, which is optionally substituted with from 1-3 $R°$; wherein from 1-4 of the ring atoms is/are a heteroatom independently selected from O, N, N—H, N—$R°$, and S; or (iv) heterocyclyl including from 4-10 ring atoms, which is optionally substituted with from 1-3 $R°$; wherein from 1-4 of the ring atoms is/are a heteroatom independently selected from O, N, N—H, N—$R°$, and S;

(in some embodiments, R1 is other than H); and each occurrence of $R°$ is independently selected from the group consisting of (beginning with halogen and through and including nitro below):

halogen;

C1-C6 alkyl; fluoro(C1-C6)alkyl;

hydroxyl;

hydroxy($C_1$-$C_4$)alkyl;

C1-C6 alkoxy; fluoro(C1-C6)alkoxy;

(C1-C6 alkyl)C(O)—;

(C1-C6 alkyl)NH—; (C1-C6 alkyl)$_2$N— (which includes, e.g., —$NMe_2$, —NMe(iPr));

—N*($R°'$)$_2$, wherein $R°'$—N*—$R°'$ together form a saturated ring having 5 or 6 ring atoms, in which 1 or 2 ring atoms (i.e., 1 or 2 ring atoms in addition to the N* ring atom) is/are optionally a heteroatom independently selected from NH, N(alkyl), O, or S (—N*($R°'$)$_2$ includes cyclic amino such as, e.g., pyrrolidinyl and morpholinyl);

formyl; formyl($C_1$-$C_4$) alkyl; cyano; cyano($C_1$-$C_4$) alkyl;

benzyl; benzyloxy;

heterocyclyl)-(C0-C6, e.g., C1-C6) alkyl, wherein the heterocyclyl portion includes 5 or 6 ring atoms, in which 1 or 2 of the ring atoms is/are a heteroatom independently selected from NH, N(alkyl), O, or S, and when said alkyl portion is present (i.e., C1-C6), said alkyl portion serves as the point of attachment to R1 (i.e., the (heterocyclyl)-(C1-C6) alkyl is connected to R1 via the alkyl portion); otherwise in the case of C0 alkyl (i.e., no alkyl portion is present), a heterocyclyl carbon ring atom serves as the point of attachment of the heterocyclyl to R1;

phenyl or heteroaryl including from 5-6 ring atoms, wherein from 1-4 of the ring atoms is/are a heteroatom independently selected from O, N, N—H, N—$R°''$, and S, each of which is optionally substituted with from 1-3 $R°''$;

$SO_2$—(C1-C6)alkyl; SO—(C1-C6)alkyl; and nitro;

in embodiments, $R°$ can be any one (or more) of the substituents listed above and/or $R°$ can be any one or more of the subsets of substituents listed above (such as those bulleted above); e.g., $R°$ can be any one (or more) of the substituents that are present, and/or any one (or more) of the substituents that encompass those that are present, in the compounds described herein;

each occurrence of $R°''$ is independently selected from the group consisting of (beginning with halogen and through and including nitro below):

halogen;

C1-C6 alkyl; fluoro(C1-C6)alkyl;

hydroxyl;

hydroxy($C_1$-$C_4$)alkyl;

C1-C6 alkoxy; fluoro(C1-C6)alkoxy;

(C1-C6 alkyl)C(O)—;

(C1-C6 alkyl)NH—; (C1-C6 alkyl)$_2$N— (which includes, e.g., —NMe2, —NMe(iPr));

formyl; formyl($C_1$-$C_4$) alkyl; cyano; cyano($C_1$-$C_4$) alkyl;

benzyl; benzyloxy;

heterocyclyl)-(C0-C6, e.g., C1-C6) alkyl, wherein the heterocyclyl portion includes 5 or 6 ring atoms, in which 1 or 2 of the ring atoms is/are a heteroatom independently selected from NH, N(alkyl), O, or S, and when said alkyl portion is present (i.e., C1-C6), said alkyl portion serves as the point of attachment to R1 (i.e., the (heterocyclyl)-(C1-C6) alkyl is connected to R1 via the alkyl portion); otherwise in the case of C0 alkyl (i.e., no alkyl portion is present), a heterocyclyl carbon ring atom serves as the point of attachment of the heterocyclyl to R1;

phenyl or heteroaryl including from 5-6 ring atoms, wherein from 1-4 of the ring atoms is/are a heteroatom independently selected from O, N, N—H, N—(C1-C6 alkyl), and S;

$SO_2$—(C1-C6)alkyl; SO—(C1-C6)alkyl; and nitro;

in embodiments, $R°''$ can be any one (or more) of the substituents listed above and/or $R°''$ can be any one or more of the subsets of substituents listed above (such as those bulleted above); e.g., $R°''$ can be any one (or more) of the substituents that are present, and/or any one (or more) of the substituents that encompass those that are present, in the compounds described herein;

II. when n=0, Z is $R_1$—V-Cy-U—Ar'/Het' wherein:

Ar'/Het' is:

(i) phenyl, pyridyl, or pyrimidinyl, each of which is optionally substituted with from 1-3 $R^p$; provided that the point of connection on said phenyl, pyridyl, or pyrimidinyl to U (i.e., the connection U—Ar'/Het' in formula I) and the point of connection on said phenyl, pyridyl, or pyrimidinyl to the amide carbonyl (i.e., the connection Ar'/Het' —C(=O) in formula I) do not result in 1,2-relation to one another on said phenyl, pyridyl, or pyrimidinyl (i.e., the points of connection to U and C(O) on said phenyl, pyridyl, or pyrimidinyl are not ortho with respect to one another); wherein $R^p$ at each occurrence is, independently, selected from H, F, chloro, $CH_3$, $CF_3$, $OCH_3$, $OCF_3$, and $OCHF_2$; or (ii) a 5-membered heteroaryl selected from pyrazolyl, pyrrolyl, thiazolyl, thienyl, furanyl, imidazolyl, oxazolyl, oxadiazolyl, thiadiazolyl, isoxazolyl, isothiazolyl, each of which is optionally substituted with from 1-3 $R^p$; provided that the point of connection on said 5-membered heteroaryls to U (i.e., the connection U—Ar'/Het' in formula I) and the point of connection on said 5-membered heteroaryls to the amide carbonyl (i.e., the connection Ar'/Het' —C(=O) in formula I) do not result in 1,2-relation to one another on said 5-membered heteroaryls (i.e., the points of connection to U and C(O) on said 5-membered heteroaryl are not adjacent to one another); or (iii) a 8-, 9- or 10-membered bicyclic heteroaryl selected from benzothienyl, benzofuranyl, benzothioazolyl, benzoxazolyl, indolyl, isoindolonyl, indolizinyl, pyrrolopyrimidinyl, pyrazolopyridinyl, imidazopyridinyl, imidazopyridazinyl, triazolopyridinyl, imidazothiazolyl, imidazooxazolyl, quinolinyl, and naphthyridinyl; each of which is optionally substituted with from 1-3 $R^p$;

(in some embodiments, Ar'/Het' is other than a 8-, 9- or 10-membered bicyclic heteroaryl selected from benzothienyl, benzofuranyl, benzothioazolyl, benzoxazolyl, indolyl, isoindolonyl, indolizinyl, pyrrolopyrimidinyl, pyrazolopyridinyl, imidazopyridinyl, imidazopyridazinyl, triazolopyridinyl, imidazothiazolyl, imidazooxazolyl, quinolinyl, and naphthyridinyl; each of which is optionally substituted with from 1-3 $R^p$;);

R1 is:
(i) hydrogen; or
(ii) C6-C10 aryl, which is optionally substituted with from 1-3 $R^q$; or
(iii) monocyclic or bicyclic heteroaryl including from 5-10 ring atoms, which is optionally substituted with from 1-3 $R^q$; wherein from 1-4 of the ring atoms is/are a heteroatom independently selected from O, N, N—H, N—$R^q$, and S; or
(iv) heterocyclyl including from 4-10 ring atoms, which is optionally substituted with from 1-3 $R^q$; wherein from 1-4 of the ring atoms is/are a heteroatom independently selected from O, N, N—H, N—$R^q$, and S; and each occurrence of $R^q$ is independently selected from the group consisting of (beginning with halogen and through and including nitro below):

halogen;
C1-C6 alkyl; fluoro(C1-C6)alkyl;
hydroxyl;
hydroxy($C_1$-$C_4$)alkyl;
C1-C6 alkoxy; fluoro(C1-C6)alkoxy;
(C1-C6 alkyl)C(O)—;
(C1-C6 alkyl)NH—; (C1-C6 alkyl)$_2$N— (which includes, e.g., —NMe$_2$, —NMe(iPr));
—N*($R^{q'}$)$_2$, wherein $R^{q'}$—N*—$R^{q'}$ together form a saturated ring having 5 or 6 ring atoms, in which 1 or 2 ring atoms (i.e., 1 or 2 ring atoms in addition to the N* ring atom) is/are optionally a heteroatom independently selected from NH, N(alkyl), O, or S (—N*($R^{q'}$)$_2$ includes cyclic amino such as, e.g., pyrrolidinyl and morpholinyl);
formyl; formyl($C_1$-$C_4$) alkyl; cyano; cyano($C_1$-$C_4$) alkyl;
benzyl; benzyloxy;
heterocyclyl)-(C0-C6, e.g., C1-C6) alkyl, wherein the heterocyclyl portion includes 5 or 6 ring atoms, in which 1 or 2 of the ring atoms is/are a heteroatom independently selected from NH, N(alkyl), O, or S, and when said alkyl portion is present (i.e., C1-C6), said alkyl portion serves as the point of attachment to R1 (i.e., the (heterocyclyl)-(C1-C6) alkyl is connected to R1 via the alkyl portion); otherwise in the case of C0 alkyl (i.e., no alkyl portion is present), a heterocyclyl carbon ring atom serves as the point of attachment of the heterocyclyl to R1;
phenyl or heteroaryl including from 5-6 ring atoms, wherein from 1-4 of the ring atoms is/are a heteroatom independently selected from O, N, N—H, N—$R^{q''}$, and S, each of which is optionally substituted with from 1-3 $R^{q''}$;
SO$_2$—(C1-C6)alkyl; SO—(C1-C6)alkyl; and
nitro;
in embodiments, $R^q$ can be any one (or more) of the substituents listed above and/or $R^q$ can be any one or more of the subsets of substituents listed above; e.g., $R^q$ can be any one (or more) of the substituents that are present, and/or any one (or more) of the substituents that encompass those that are present, in the compounds described herein;
each occurrence of $R^{q''}$ is independently selected from the group consisting of (beginning with halogen and through and including nitro below):
halogen;
C1-C6 alkyl; fluoro(C1-C6)alkyl;
hydroxyl;
hydroxy($C_1$-$C_4$)alkyl;
C1-C6 alkoxy; fluoro(C1-C6)alkoxy;
(C1-C6 alkyl)C(O)—;
(C1-C6 alkyl)NH—; (C1-C6 alkyl)$_2$N— (which includes, e.g., —NMe$_2$, —NMe(iPr));
formyl; formyl($C_1$-$C_4$) alkyl; cyano; cyano($C_1$-$C_4$) alkyl;
benzyl; benzyloxy;
heterocyclyl)-(C0-C6, e.g., C1-C6) alkyl, wherein the heterocyclyl portion includes 5 or 6 ring atoms, in which 1 or 2 of the ring atoms is/are a heteroatom independently selected from NH, N(alkyl), O, or S, and when said alkyl portion is present (i.e., C1-C6), said alkyl portion serves as the point of attachment to R1 (i.e., the (heterocyclyl)-(C1-C6) alkyl is connected to R1 via the alkyl portion); otherwise in the case of C0 alkyl (i.e., no alkyl portion is present), a heterocyclyl carbon ring atom serves as the point of attachment of the heterocyclyl to R1;
phenyl or heteroaryl including from 5-6 ring atoms, wherein from 1-4 of the ring atoms is/are a heteroatom independently selected from O, N, N—H, N—(C1-C6 alkyl), and S;
SO$_2$—(C1-C6)alkyl; SO—(C1-C6)alkyl; and
nitro;
in embodiments, $R^{q''}$ can be any one (or more) of the substituents listed above and/or $R^{q''}$ can be any one or more of the subsets of substituents listed above; e.g., $R^{q''}$ can be any one (or more) of the substituents that are present, and/or any one (or more) of the substituents that encompass those that are present, in the compounds described herein;
U is selected from:
(i) =$CR^r$ (for purposes of clarification, in these embodiments, the carbon atom in =$CR^r$ is doubly bonded to a ring atom (e.g., ring carbon atom) of Cy, thereby forming an exocyclic double bond, see, e.g., compounds F1-F7); or
(ii) —U'—C($R^s$)$_2$— or —C($R^s$)$_2$—U'—; wherein:
$R^r$ hydrogen, F, C1-C6 alkyl, fluoro C1-C6 alkyl, C3-C6 cycloalkyl, C1-C6 alkoxy C1-C6 fluoroalkoxy, and cyano;
each occurrence of $R^s$ is independently selected from H, F, OH, C1-C6 alkyl, C3-C6 cycloalkyl, NH$_2$, OCO—(C1-C6 alkyl), OCO—(C3-C6 cycloalkyl), C1-C6 alkoxy C1-C6 fluoroalkoxy, and cyano; or $R^s$—C—$R^s$ together form C3-C6 cycloalkyl or heterocyclyl including 3-6 ring atoms, in which one of the heterocyclyl ring atoms is selected from O; S(O)m and $NR^u$;

each occurrence of $R^u$ is independently selected from H, C1-C6 alkyl, —C(=O)H, —C(=O)$R^v$, C(=O)O(C1-C6 alkyl), C(=O)N($R^w$)$_2$, SO$_2$—$R^v$, wherein $R^v$ is selected from C1-C6 alkyl, CH$_2$-(heteroaryl including 5-10 ring atoms), CH$_2$—(C6-C10 aryl), and C6-C10 aryl; and each occurrence of $R^w$ is independently selected from H, C1-C6 alkyl, CH$_2$-(heteroaryl including 5-10 ring atoms), CH$_2$—(C6-C10 aryl), and C6-C10 aryl (e.g., in embodiments, the aryl and heteroaryl portion in $R^v$ and $R^w$ can be optionally substituted, e.g., with one or more independently selected substituents such as F, C1-C6 alkyl, fluoro C1-C6 alkyl, C3-C6 cycloalkyl, C1-C6 alkoxy, C1-C6 fluoroalkoxy, or cyano);

U' is a bond; O; $NR^u$; S(O)$_m$ (m=0-2); CH$_2$; and U"—CH$_2$—; wherein U''' is O; $NR^u$; S(O)$_m$ (m=0-2);

Cy is C4-C10 (e.g., C4-C8, C4-C6) cycloalkyl or saturated heterocyclyl including 4-10 (e.g., 4-8, 4-6) ring atoms, each of which is optionally substituted with from 1-3 $R^x$ (wherein each occurrence of $R^x$ is independently selected from F, OH, C1-C6 alkyl, fluoro C1-C6 alkyl, C3-C6 cycloalkyl, C1-C6 alkoxy C1-C6 fluoroalkoxy, and cyano), in which from 1-3 heteroatoms are independently selected from O, N—H, $NR^{x'}$ (wherein $R^{x'}$ is defined as $R^{q''}$), and S(O)m (m=0-2); wherein when the heterocyclyl contains a secondary amine as part of its structure, then:

(i) V is linked through the nitrogen of the secondary amine portion of the heterocyclyl; and (ii) U is linked to Cy via a Cy ring carbon atom; wherein the bond between U and the Cy ring carbon is a single or double bond; and (iii) V-Cy and Cy-U do no lead to 1,2 relationship (i.e. the Cy ring carbon atom that is attached to U is not adjacent to Cy ring nitrogen atom that is attached to V);

for purposes of clarification, the phrases "heterocyclyl contains a secondary amine as part of its structure" and "heterocyclyl that contains a secondary amine as part of its structure" as used herein, mean that the parent heterocycle includes as part of its structure a ring nitrogen atom of the following formula:

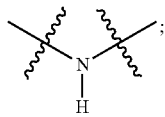 [SMILES: *N*]

in which the bonds intersected by the wavy lines indicate bonds between the nitrogen atom and other ring atoms in the parent heterocycle (the above-shown portion of the parent heterocycle is sometimes referred to herein as the "secondary amine" portion); other additional heteroatoms (including nitrogens, including other secondary amine nitrogens) can also be present in such a parent heterocycle, however, when one (or more) secondary amine(s) is(are) present in the parent heterocycle, it is the (or one of the) secondary amine nitrogen atom(s) that serves as the point of attachment of that heterocycle to variable V (i.e., V replaces the H of the N—H in the parent heterocycle; see, e.g., compounds F1-F7); examples of such parent heterocycles include, without limitation, azetidine, pyrrolidine, piperidine, azepane, diazepane, isoxazolidine, thiazolidinone, imidazolidinone, pyrrolidinone, azabicyclooctane (aka. tropane), azabicycloheptane, azabicyclohexane; accordingly, examples of heterocyclyl that contains a secondary amine as part of its structure include, without limitation, azetidinyl, pyrrolidinyl, piperidinyl, azepanyl, diazepanyl, isoxazolidinyl, thiazolidinonyl, imidazolidinonyl, pyrrolidinonyl, azabicyclooctanyl (aka. tropanyl), azabicycloheptanyl, azabicyclohexanyl;

V is selected from:
(i) —V'—C($R^y$)$_2$— or —C($R^y$)$_2$—V'—; or
(ii) O, $NR^z$, or S(O)m (m=0-2); or
(iii) —CH=CH—, C=O, C($R^y$)$_2$—C(=O), —C(=O)—C($R^y$)$_2$—, —SO$_2$NRz', $NR^z$SO$_2$, —C(=O)$NR^z$, and $NR^z$C(=O); wherein:

each occurrence of $R^y$ is independently selected from H, F, OH, C1-C6 alkyl, C3-C6 cycloalkyl, NH$_2$, OCO—(C1-C6 alkyl), OCO—(C3-C6 cycloalkyl), C1-C6 alkoxy C1-C6 fluoroalkoxy, and cyano; or $R^y$—C—$R^y$ together form C3-C6 cycloalkyl or heterocyclyl including 3-6 ring atoms, in which one of the heterocyclyl ring atoms is selected from O; S(O)m and $NR^{aa}$;

each occurrence of $R^z$ and $R^{aa}$ is independently selected from H, C1-C6 alkyl, —C(=O)H, —C(=O)$R^v$, C(=O)O (C1-C6 alkyl), C(=O)N($R^w$)$_2$, SO$_2$—$R^v$, wherein $R^v$ is selected from C1-C6 alkyl, CH$_2$-(heteroaryl including 5-10 ring atoms), CH$_2$—(C6-C10 aryl), and C6-C10 aryl; and each occurrence of $R^w$ is independently selected from H, C1-C6 alkyl, CH$_2$-(heteroaryl including 5-10 ring atoms), CH$_2$—(C6-C10 aryl), and C6-C10 aryl;

V' is a bond; O; $NR^u$; S(O)$_m$ (m=0-2); —C(O)O—(C$R^y_2$)$_{0-2}$—, —(C$R^y_2$)$_{0-2}$—O—C(O)—, C($R^y$)$_2$, C($R^y$)$_2$—C($R^y$)$_2$; —($R^y$)$_2$—V'''; and V'''—C($R^y$)$_2$—; wherein V''' is O; $NR^z$; S(O)$_m$ (m=0-2); wherein each occurrence of $R^y$ is independently defined as above;

(in some embodiments, V' is a bond; O; $NR^u$; S(O)m (m=0-2); —C(O)—O—(CH$_2$)$_{0-2}$—, —(CH$_2$)$_{0-2}$—O—C(O)—, CH$_2$; —CH$_2$—V'''; and V'''—CH$_2$—; wherein V''' is O; $NR^z$; S(O)m (m=0-2));

R2 is selected from H, F, Cl, CF$_3$, CF$_2$CF$_3$, CH$_2$CF$_3$, OCF$_3$, OCHF$_2$, phenyl; substituted phenyl (e.g., phenyl substituted with from 1-3 substituents independently selected from F, OH, C1-C6 alkyl, fluoro(C1-C6) alkyl C3-C6 cycloalkyl, NH$_2$, C1-C6 alkoxy, C1-C6 fluoroalkoxy, and cyano); thienyl; thiazolyl; and pyrazol-1-yl; and R3 is H, F, or Cl; or a salt (e.g., a pharmaceutically acceptable salt) thereof.

In another aspect, a compound of the formula (I) is featured, in which n=1, and each of the attendant definitions associated with n=1 (as well as R2 and R3) can be as defined anywhere herein (in some embodiments, the definition of Ar/Het can further include 3,5-dimethylpyrazolyl).

In another aspect, a compound of the formula (I) is featured, in which n=0, and each of the attendant definitions associated with n=0 (as well as R2 and R3) can be as defined anywhere herein.

In a further aspect, the formula (I) compounds specifically described herein (or a salt, e.g., a pharmaceutically acceptable salt thereof) are featured (e.g., compounds A1-A12, B1-B6, C1-C3, D1-D16, E1, E2, F1-F7, G1 and G2).

In one aspect, a composition (e.g., a pharmaceutical composition) is featured, which includes a compound of formula (I) or a salt (e.g., a pharmaceutically acceptable salt) thereof as defined anywhere herein and a pharmaceutically acceptable carrier. In some embodiments, the composition can include an effective amount of the compound or salt. In some embodiments, the composition can further include an additional therapeutic agent.

In another aspect, a dosage form is featured, which includes from about 0.05 milligrams to about 2,000 milligrams (e.g., from about 0.1 milligrams to about 1,000 milligrams, from about 0.1 milligrams to about 500 milligrams, from about 0.1 milligrams to about 250 milligrams, from about 0.1 milligrams to about 100 milligrams, from about 0.1 milligrams to about 50 milligrams, or from about 0.1 milligrams to about 25 milligrams) of a compound of formula (I) or a salt (e.g., a pharmaceutically acceptable salt) thereof as defined anywhere herein. The dosage form can further include a pharmaceutically acceptable carrier and/or an additional therapeutic agent.

The invention relates generally to inhibiting an HDAC (e.g., HDAC1 or HDAC2; e.g., HDAC3) with a compound of formula (I) or a salt (e.g., a pharmaceutically acceptable salt) thereof as defined anywhere herein. In some embodiments, the methods can include, e.g., contacting an HDAC (e.g., HDAC1 or HDAC2; e.g., HDAC3) in a sample (e.g., a cell or tissue) with a compound of formula (I) or a salt (e.g., a pharmaceutically acceptable salt) thereof as defined anywhere herein. In other embodiments, the methods can include administering a compound of formula (I) or a salt (e.g., a pharmaceutically acceptable salt) thereof as defined anywhere herein to a subject (e.g., a mammal, such as a human). Accordingly, in yet another aspect, this invention includes methods of screening for compounds that inhibit (e.g., selectively inhibit) one or more HDACs (e.g., HDAC1 or HDAC2; e.g., HDAC3).

In one aspect, a method of selectively inhibiting HDAC3 is featured, which includes contacting an HDAC3 in a sample (e.g., a cell or tissue) with a compound of formula (I) or a salt (e.g., a pharmaceutically acceptable salt) thereof as defined anywhere herein; or administering a compound of formula (I) or a salt (e.g., a pharmaceutically acceptable salt) thereof as defined anywhere herein to a subject (e.g., a mammal, such as a human).

In one aspect, a method of selectively inhibiting HDAC1 or HDAC2 (e.g., HDAC1) is featured, which includes contacting HDAC1 or HDAC2 (e.g., HDAC1) in a sample (e.g., a cell or tissue) with a compound of formula (I) or a salt (e.g., a pharmaceutically acceptable salt) thereof as defined anywhere herein; or administering a compound of formula (I) or a salt (e.g., a pharmaceutically acceptable salt) thereof as defined anywhere herein to a subject (e.g., a mammal, such as a human).

In one aspect, methods of treating (e.g., controlling, relieving, ameliorating, alleviating, or slowing the progression of) or methods for preventing (e.g., delaying the onset of or reducing the risk of developing) a disease or disorder mediated by HDAC1 or HDAC2 in a subject (e.g., a mammal, such as a human) in need thereof are featured, which include administering a compound of formula (I) or a salt (e.g., a pharmaceutically acceptable salt) thereof as defined anywhere herein to the subject.

In one aspect, methods of treating (e.g., controlling, relieving, ameliorating, alleviating, or slowing the progression of) or methods for preventing (e.g., delaying the onset of or reducing the risk of developing) a disease or disorder mediated by HDAC3 in a subject (e.g., a mammal, such as a human) in need thereof are featured, which include administering a compound of formula (I) or a salt (e.g., a pharmaceutically acceptable salt) thereof as defined anywhere herein to the subject.

In one aspect, featured are methods of treating (e.g., controlling, relieving, ameliorating, alleviating, or slowing the progression of) or methods for preventing (e.g., delaying the onset of or reducing the risk of developing) a neurological disorder such as Friedreich's ataxia, myotonic dystrophy, spinal muscular atrophy, fragile X syndrome, Huntington's disease, spinocerebellar ataxia, Kennedy's disease, amyotrophic lateral sclerosis, spinal and bulbar muscular atrophy, and Alzheimer's disease; a cancer (e.g. cutaneous T cell lymphoma, B cell lymphomas, and colorectal cancer); an inflammatory disease (e.g., psoriasis, rheumatoid arthritis, and osteoarthritis); a memory impairment condition; post-traumatic stress disorder; a drug addiction; a *Plasmodium falciparum* infection (e.g., malaria) as well as other parasite infections in a subject (e.g., a mammal, such as a human) in need thereof, which include administering a compound of formula (I) or a salt (e.g., a pharmaceutically acceptable salt) thereof as defined anywhere herein to the subject.

In one aspect, a compound of formula (I) or a salt (e.g., a pharmaceutically acceptable salt) thereof as defined anywhere herein for use in medicine is featured.

In one aspect, featured is a compound of formula (I) or a salt (e.g., a pharmaceutically acceptable salt) thereof as defined anywhere herein for the treatment of:
a disease or disorder mediated by HDAC1 or HDAC2;
a disease or disorder mediated by HDAC3;
a neurological disorder such as Friedreich's ataxia, myotonic dystrophy, spinal muscular atrophy, fragile X syndrome, Huntington's disease, spinocerebellar ataxia, Kennedy's disease, amyotrophic lateral sclerosis, spinal and bulbar muscular atrophy, and Alzheimer's disease; a cancer (e.g. cutaneous T cell lymphoma, B cell lymphomas, and colorectal cancer); an inflammatory disease (e.g., psoriasis, rheumatoid arthritis, and osteoarthritis); a memory impairment condition; post-traumatic stress disorder; a drug addiction; a *Plasmodium falciparum* infection (e.g., malaria) as well as other parasite infections.

In one aspect, featured is a use of a compound of formula (I) or a salt (e.g., a pharmaceutically acceptable salt) thereof as defined anywhere herein, in the preparation of a medicament for the treatment of:
a disease or disorder mediated by HDAC1 or HDAC2;
a disease or disorder mediated by HDAC3;
a neurological disorder such as Friedreich's ataxia, myotonic dystrophy, spinal muscular atrophy, fragile X syndrome, Huntington's disease, spinocerebellar ataxia, Kennedy's disease, amyotrophic lateral sclerosis, spinal and bulbar muscular atrophy, and Alzheimer's disease; a cancer (e.g. cutaneous T cell lymphoma, B cell lymphomas, and colorectal cancer); an inflammatory disease (e.g., psoriasis, rheumatoid arthritis, and osteoarthritis); a memory impairment condition; post-traumatic stress disorder; a drug addiction; a *Plasmodium falciparum* infection (e.g., malaria) as well as other parasite infections.

In some embodiments, the subject can be a subject in need thereof (e.g., a subject identified as being in need of such treatment, such as a subject having, or at risk of having, one or more of the diseases or conditions described herein). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject can be a human.

In one aspect, methods of making compounds described herein are featured. In embodiments, the methods include taking any one of the intermediate compounds described herein and reacting it with one or more chemical reagents in one or more steps to produce a compound of formula (I) or a salt (e.g., a pharmaceutically acceptable salt) thereof as defined anywhere herein.

Some of the formula (I) compounds described herein have enhanced (e.g., increased, e.g., increased by a factor of about 2 or more) stabilities in acid. In some embodiments, the formula (I) compounds have enhanced resistances to degradation, e.g., less than about 25% degradation (e.g., less than about 20% degradation, less than about 15% degradation, or less than about 10% degradation) when exposed to acidic pH, e.g., acidic conditions intended to mimic those in the stomach, e.g., incubation (e.g., as a 10 μM solution) at 50° C. and at a pH of about 2.0 for about four hours. The resistance of compounds to degradation or metabolism at acidic pH can be a useful feature for a pharmaceutical agent (e.g., a drug). Increased stability at low pH can allow, for example, process preparation steps, such as salt formation, to occur without significant degradation of the desired salt. In addition, it is preferable that orally administered pharmaceuticals are stable to the acidic pH of the stomach. In some embodiments, compounds display enhanced stability when exposed to acidic pH with stability half-lives greater than e.g. 12 h or e.g. 18 h or e.g 24 h at pH 2 and 50° C.

In some embodiments, the formula (I) compounds described herein selectively inhibit HDAC3, e.g., selectively inhibit HDAC3 over HDAC1 and HDAC2 (e.g exhibiting 5-fold or greater selectivity, e.g. exhibiting 25-fold or greater selectivity). While not wishing to be bound by theory, it is believed that HDAC3-selective inhibitors can increase expression of frataxin, and could therefore be useful in the treatment of neurological conditions (e.g., neurological conditions associated with reduced frataxin expression, such as Friedreich's ataxia). It is also believed that HDAC3 inhibition plays an important role in memory consolidation (McQuown S C et al, J Neurosci 31 764 (2011)). Selective inhibitors of HDAC3 could provide advantages for treatment of neurological conditions over the use of broad-spectrum HDAC inhibitors by reducing toxicities associated with inhibition of other HDACs. Such specific HDAC3 inhibitors would provide a higher therapeutic index, resulting in better tolerance by patients during chronic or long-term treatment.

In some further embodiments, compounds selectively inhibit HDAC1 and/or HDAC2 (e.g exhibiting 5-fold or greater selectivity, e.g. exhibiting 25-fold or greater selectivity).

In some embodiments, the formula (I) compounds described herein have been shown to inhibit class I histone deacetylases and this inhibition has resulted in an in vitro increased frataxin mRNA expression in Friedreich's ataxia patient peripheral blood mononuclear cells (PBMCs). In other embodiments compounds of the invention have been shown to inhibit in vitro proliferation of colorectal cancer cells in a dose-dependent fashion. In further embodiments compounds of the invention have been demonstrated to increase long term memory in vivo using the novel object recognition paradigm.

In some embodiments, the formula (I) compounds described herein exhibit enhanced brain penetration. For example, brain/plasma ratios of greater than about 0.25 (e.g., greater than about 0.50, greater than about 1.0, greater than about 1.5, or greater than about 2.0) are observed when mice are dosed with some of the formula (I) compounds described herein. Such compounds are therefore expected to be particularly suitable for therapies targeting the brain (e.g., neurological conditions such as Friedreich's ataxia, myotonic dystrophy, spinal muscular atrophy, fragile X syndrome, Huntington's disease, spinocerebellar ataxia, Kennedy's disease, amyotrophic lateral sclerosis, spinal and bulbar muscular atrophy, and Alzheimer's disease; a memory impairment condition; post-traumatic stress disorder; a drug addiction).

In some embodiments, the formula (I) compounds described herein selectively inhibit HDAC3, e.g., selectively inhibit HDAC3 over HDAC1 and HDAC2 (e.g exhibiting 5-fold or greater selectivity, e.g. exhibiting 25-fold or greater selectivity) and exhibit enhanced brain penetration (e.g., as described above).

In some embodiments, the formula (I) compounds described herein selectively inhibit HDAC1 and/or HDAC2, e.g., selectively inhibit HDAC1 and/or HDAC2 over HDAC3 (e.g exhibiting 5-fold or greater selectivity, e.g. exhibiting 25-fold or greater selectivity) and exhibit enhanced brain penetration (e.g., as described above).

Embodiments can include one or more of the following features.

[I] n is 1 (i.e., in which Z is $R_1$—X—Ar/Het). Embodiments in which n is 1 can include one or more of the following features described throughout sections [A] through [F] below.

[A] Variable X

[1] In some embodiments, X is —Y—[C($R^a$)$_2$]$_a$-A-[C($R^b$)$_2$]$_b$—B—. Embodiments can also include one or more of the features described in [a][d] below.

[a]

A is a bond and/or B is a bond (in some embodiments, each of A and B is a bond; or one of A and B (e.g., B) is a bond, and the other of A and B (e.g., A) is other than a bond, e.g., O or $NR^f$, e.g., O; in embodiments, each of A and B is other than $S(O)_m$).

Each occurrence of $R^a$ and $R^b$ (when present) is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy C1-C6 fluoroalkoxy, and cyano.

Each occurrence of $R^a$ and $R^b$ (when present) is independently selected from H, F, C1-C6 alkyl, and C3-C6 cycloalkyl.

Each occurrence of $R^a$ and $R^b$ (when present) is H.

One or more (e.g., one) of the following apply:

any two $R^a$, together with the carbons to which each is attached, together form C3-C6 cycloalkyl or heterocyclyl including 3-6 ring atoms, in which one of the heterocyclyl ring atoms is selected from O; $S(O)_m$ and $NR^g$; in these embodiments, any remaining occurrences of $R^a$ and any occurrence of $R^b$ are each independently defined according to any one or more of the preceding or following definitions pertaining to $R^a$ and $R^b$; or one $R^a$ and one $R^b$, together with the carbons to which each is attached, form C3-C6 cycloalkyl or heterocyclyl including 3-6 ring atoms, in which one of the heterocyclyl ring atoms is selected from O; $S(O)_m$ and $NR^g$; in these embodiments, the other $R^a$, the other $R^b$, and any other remaining occurrences of $R^a$ and $R^b$ are each independently defined according to any one or more of the preceding or following definitions pertaining to $R^a$ and $R^b$; or any two $R^b$, together with the carbons to which each is attached, form C3-C6 cycloalkyl or heterocyclyl including 3-6 ring atoms, in which one of the ring atoms is selected from O; $S(O)_m$ and $NR^g$; in these embodiments, each occurrence of $R^a$ and any other remaining occurrences of $R^b$ are each independently defined according to any one or more of the preceding definitions pertaining to $R^a$ and $R^b$.

[b]

In some embodiments, Y is $CR^c$=$CR^d$ (in some embodiments, the double bond between $CR^c$ and $CR^d$ has the trans configuration; in other embodiments, the double bond between $CR^c$ and $CR^d$ has the cis configuration). Embodiments can include one or more of the following features.

The double bond between $CR^c$ and $CR^d$ has the trans configuration. Each of $R^c$ and $R^d$ is, independently, selected from H, F, OH, C1-C6 alkyl, C3-C5 cycloalkyl, $NH_2$, OCO—(C1-C6 alkyl), OCO—(C3-C5 cycloalkyl), C1-C6 alkoxy, C1-C6 fluoroalkoxy, and cyano. In certain embodiments, each of $R^c$ and $R^d$ is H.

A is a bond and/or B is a bond (in some embodiments, each of A and B is a bond).

Each of $R^a$ and $R^b$ can be as defined anywhere herein (see, for example, the $R^a$ and $R^b$ features described above in section [I][A][1][a]).

a is 1 or 2 (e.g., 1). b is 0 or 1 (e.g., 0).

a is 1 or 2, e.g., 1; and b is 0 or 1, e.g., 0 (in further embodiments, each of A and B is also a bond).

b is 0 (in embodiments, a is 1 or 2, e.g., 1; in further embodiments, each of A and B is also a bond).

X is —CH=CH—C($R^a$)$_2$—. In certain embodiments, each $R^a$ is hydrogen. In other embodiments, each $R^a$ is a substituent other than hydrogen (e.g., C1-C6 alkyl), and each $R^a$ can be the same or different, e.g., the same. For example, each $R^a$ can be the same C1-C6 alkyl, such as $CH_3$.

X is —CH=CH—CH($R^a$)—. In certain embodiments, $R^a$ is hydrogen; in other embodiments, $R^a$ is a substituent other than hydrogen (e.g., as described above).

X is —CH=CH—C($R^a$)$_2$—C($R^a$)$_2$. In certain embodiments, each $R^a$ is hydrogen. In other embodiments, each $R^a$ is a substituent other than hydrogen (e.g., C1-C6 alkyl), and each $R^a$ can be the same or different, e.g., the same. For example, each $R^a$ can be the same C1-C6 alkyl, such as $CH_3$. In still other embodiments, in one germinal pair of $R^a$'s, each $R^a$ is hydrogen; and in the other germinal pair of $R^a$'s, each $R^a$ is a substituent other than hydrogen (e.g., as described above).

X is —CH=CHCH($R^a$)CH($R^a$). In certain embodiments, each $R^a$ is hydrogen; in other embodiments, each $R^a$ is a substituent other than hydrogen; in still other embodiments, one $R^a$ is hydrogen, and the other is a substituent other than hydrogen.

For example, X is —CH=CH—$CH_2$— or —CH=CH—$CH_2$—$CH_2$— (e.g., in the foregoing embodiments, the double bond can have the trans configuration; and further each of A and B can be a bond). In certain embodiments, X is —CH=CH—$CH_2$— (e.g., trans).

[c]

In some embodiments, Y is O, $NR^e$, or $S(O)_m$; e.g., Y is O or $NR^e$. Embodiments can include one or more of the following features.

Y is O.

Y is $NR^e$ (e.g., $R^e$ is C1-C6 alkyl).

A is a bond and/or B is a bond (in some embodiments, each of A and B is a bond).

Each of $R^a$ and $R^b$ can be as defined anywhere herein (see, for example, the $R^a$ and $R^b$ features described above in section [I][A][1][a]).

a is 2 or 3 (e.g., 2) and b is optionally other than 0 (e.g., 1 or 2); in embodiments, A is a bond; or A is other than a bond, e.g., O or $NR^f$, e.g., O; and B is a bond. Some examples are provided below:

a is 2 or 3 (e.g., 2), b is 0; and each of A and B is a bond.

a is 2 or 3 (e.g., 2), b is other than 0 (e.g., 1 or 2), and each of A and B is a bond.

a is 2 or 3 (e.g., 2), b is other than 0 (e.g., 2 or 3), A is other than a bond, e.g., O or $NR^f$, e.g., O, and B is a bond.

For example, X is —O—$(CH_2)_{2-3(e.g., 2)}$ or —N($CH_3$)—$(CH_2)_{2-3(e.g., 2)}$.

[d]

In some embodiments, Y is a bond. Embodiments can include one or more of the following features.

A is a bond, O, or $NR^e$ (e.g., A is a bond or O, e.g., A is a bond) and/or B is a bond. In certain embodiments, A is a bond and B is a bond.

Each of $R^a$ and $R^b$ can be as defined anywhere herein (see, for example, the $R^a$ and $R^b$ features described above in section [I][A][1][a]).

b is 0 (in embodiments, a can be 1, 2, or 3 (e.g., 1) and one or more of the following can apply: A is a bond, A is other than a bond, such as O; B is a bond, each of $R^a$ is H; e.g., A is a bond, a is 1, B is a bond; e.g., X is $CH_2$).

b is 1, 2, or 3 (in embodiments, a can be 1, 2, or 3 and one or more of the following can apply: A is a bond, A is other than a bond, such as O; B is a bond, each of $R^a$ is H, each of $R^b$ is H). In certain of these embodiments, X has a span of not more than 4 atoms.

[2] In some embodiments, X is a bond.

[B] Variables R4 and R5

In some embodiments, each of R4 and R5 is H.

[C] Variable Ar/Het

[1]

In some embodiments, Ar/Het is 5 membered heteroaromatic chosen from pyrazolyl, thiazolyl, oxazolyl, imidazolyl, thienyl, furanyl, isoxazolyl, isothiazolyl, thiadiazolyl, oxadiazolyl, and 1,2,4-triazolyl (in some embodiments, the definition of Ar/Het can further include 3,5-dimethylpyrazolyl); or a bicyclic 8-, 9-, or 10-membered heteroaromatic chosen from benzofuranyl, benzothienyl, benzothiazolyl, indolyl, indazolyl, quinolonyl, and naphtyridinyl (in some embodiments, Ar/Het is other than furanyl and 1,2,4-triazolyl. In certain embodiments, Ar/Het is other than furanyl; in certain embodiments, Ar/Het is other than 1,2,4-triazolyl).

In some embodiments, Ar/Het is 5 membered heteroaromatic selected from pyrazolyl, thiazolyl, oxazolyl, imidazolyl, isoxazolyl, isothiazolyl, thiadiazolyl, oxadiazolyl, and 1,2,4-triazolyl (in some embodiments, Ar/Het is other than furanyl and 1,2,4-triazolyl. In certain embodiments, Ar/Het is other than furanyl; in certain embodiments, Ar/Het is other than 1,2,4-triazolyl). In certain embodiments, Ar/Het is pyrazolyl. In some embodiments, the definition of Ar/Het can further include 3,5-dimethylpyrazolyl.

In some embodiments, Ar/Het is other than furanyl and 1,2,4-triazolyl. In certain embodiments, Ar/Het is other than furanyl. In certain embodiments, Ar/Het is other than 1,2,4-triazolyl.

[2]

In some embodiments, Ar/Het is a bicyclic 8-, 9-, or 10-membered heteroaryl selected from the group consisting of benzofuranyl, benzothienyl, benzothiazolyl, indolyl, indazolyl, quinolonyl, naphtyridinyl, indolizinyl, pyrrolopyrimidinyl, pyrazolopyridinyl, imidazopyridinyl, imidazopyridazinyl, triazolopyridinyl, imidazothiazolyl, imidazooxazolyl, triazolothiazolyl, and triazolooxazolyl.

In some embodiments, Ar/Het is a bicyclic 8-, 9-, or 10-membered azabridged hetero aromatic such as indolizinyl, pyrrolopyrimidinyl, pyrazolopyridinyl, imidazopyridinyl, imidazopyridazinyl, triazolopyridinyl, imidazothiazolyl, imidazooxazolyl, 1,2,4-triazolothiazolyl, and 1,2,4-triazolooxazolyl.

[D] Variable R1

[1]

In some embodiments, R1 is C6-C10 aryl, which is optionally substituted with from 1-3 R°. In certain embodiments, R1 is phenyl or naphthyl (e.g., phenyl), which is optionally substituted with from 1-3 R° (in embodiments, each R° is independently selected from F, OH, C1-C6 alkyl, fluoro(C1-C6) alkyl C3-C6 cycloalkyl, $NH_2$, C1-C6 alkoxy, C1-C6 fluoroalkoxy, and cyano).

In other embodiments, R1 is C8-C10 aryl, which contains a phenyl ring fused to a non-aromatic ring and which is optionally substituted with from 1-3 R° (e.g., optionally substituted indanyl or tetralinyl).

[2]

In some embodiments, R1 is monocyclic or bicyclic heteroaryl including from 5-10 ring atoms, which is optionally substituted with from 1-3 R°; wherein from 1-4 of the ring atoms is/are a heteroatom independently selected from O, N, N—H, N—R°, and S.

In certain embodiments, R1 is monocyclic heteroaryl, such as pyridyl.

In other embodiments, R1 is bicyclic heteroaryl, such as those that are fully aromatic such as indolyl and the like.

In still other embodiments, R1 is bicyclic heteroaryl that contains a bridgehead nitrogen ring atom and optionally other heteroatom ring atoms, such as indolizinyl, pyrrolopyrimidinyl, pyrazolopyridinyl, imidazopyridinyl, imidazopyriazinyl, triazolopyridinyl, imidazothiazolyl, imidazooxazolyl.

Other examples of R1 heteroaryl groups include, without limitation, pyrazolyl, pyrrolyl, 2-oxo-indolyl, quinolinyl, isoquinolinyl, tetrahydro-isoquinolinyl, benzofuranyl, benzodioxanyl, benzodioxolyl (aka. methylenedioxyphenyl) and corresponding difluoro ($CF_2$) analog, thiazolyl, 2-oxopyridinyl, pyridinyl N-oxide, pyrimidinyl, thienyl, furanyl, oxazolyl, isoxazolyl, pyridazinyl, imidazolyl, pyrazinyl, isothiazolyl, 1,2-thiazinyl-1,1-dioxide, benzimidazolyl, thiadiazolyl, benzopyranyl, benzothiazolyl, benzotriazolyl, benzoxazolyl, benzothienyl, oxadiazolyl, triazolyl, tetrazolyl, dioxoindolyl (isatin), phthalimido and the dihydro and tetrahydro congeners of the fully unsaturated ring systems.

[3]

In some embodiments, R1 is heterocyclyl including from 4-10 ring atoms, which is optionally substituted with from 1-3 R°; wherein from 1-4 of the ring atoms is/are a heteroatom independently selected from O, N, N—H, N—R°, and S (e.g., bicyclic heterocyclyl containing a bridgehead nitrogen ring atom and optionally other heteroatom ring atoms).

Examples of R1 heterocyclyl groups include, without limitation, piperidinyl, morpholinyl, pyrrolidinyl, azetidinyl, azepanyl, isoxazolidinyl, oxazolidinyl, thiazolidinyl, imidazolinyl, quinuclidinyl, isothiazolidinyl, tetrahydrofuranyl, tetrahydropyranyl, thiamorpholinyl, thiamorpholinyl sulfoxide, thiamorpholinyl sulfone, dioxanyl, tropanyl and other bridged bicyclic amines, quiniclidinyl.

[4]

In some embodiments, R1 is H.

[E] Variables R2 and R3

[1]

In some embodiments, R2 is a substituent other than hydrogen (e.g., phenyl, substituted phenyl, thienyl, thiazolyl, and pyrazol-1-yl), and R3 is hydrogen. In certain embodiments, the compounds can exhibit selectivity for HDAC 1 and/or 2.

[2]

In some embodiments, R2 is hydrogen, and R3 is a substituent other than hydrogen (e.g., fluoro). In certain embodiments, the compounds can exhibit selectivity for HDAC 3.

[3]

In some embodiments, each of R2 and R3 is hydrogen.

[F] Non-Limiting Combinations of [I][A] through [I][E] (i.e., n=1)

In some embodiments, one or more of the features described in one or more of [A][1][a], [A][1][b], [A][1][c], and [A][1][d] can be combined with: the features described in [B], and/or one or more of the features described in one or both of [C][1] and [C][2], and/or one or more of the features described in one or more of [D][1], [D][2], [D][3], and [D][4], and/or one or more of the features described in one or more of [E][1], [E][2], and [E][3].

In some embodiments, one or more of the features described in one or more of [A][1][a], [A][1][b], [A][1][c], and [A][1][d] can be combined with: the features described in [B], and one or more of the features described in one or both of [C][1] and [C][2], and one or more of the features described in one or more of [D][1], [D][2], [D][3], and [D][4], and one or more of the features described in one or more of [E][1], [E][2], and [E][3].

In some embodiments, one or more of the features described in one or more of [A][1][a], [A][1][b], [A][1][c], and [A][1][d] can be combined with: the features described in [B], and one or more of the features described in [C][1], and one or more of the features described in one or more of [D][1], [D][2], [D][3], and [D][4], and one or more of the features described in one or more of [E][1], [E][2], and [E][3].

In some embodiments, one or more of the features described in one or more of [A][1][a], [A][1][b], [A][1][c], and [A][1][d] can be combined with: the features described in [B], and one or more of the features described in one or both of [C][1] and [C][2], and one or more of the features described in one or both of [D][1] and [D][4] (e.g., [D][1]), and one or more of the features described in one or more of [E][1], [E][2], and [E][3].

In some embodiments, one or more of the features described in one or more of [A][1][a], [A][1][b], [A][1][c], and [A][1][d] can be combined with: the features described in [B], and one or more of the features described in [C][1], and one or more of the features described in one or both of [D][1] and [D][4] (e.g., [D][1]), and one or more of the features described in one or more of [E][1], [E][2], and [E][3].

In some embodiments, one or more of the features described in [A][1][b] can be combined with: the features described in [B], and one or more of the features described in one or both of [C][1] and [C][2], and one or more of the features described in one or more of [D][1], [D][2], [D][3], and [D][4], and one or more of the features described in one or more of [E][1], [E][2], and [E][3].

In some embodiments, one or more of the features described in [A][1][b] can be combined with: the features described in [B], and one or more of the features described in [C][1], and one or more of the features described in one or more of [D][1], [D][2], [D][3], and [D][4], and one or more of the features described in one or more of [E][1], [E][2], and [E][3].

In some embodiments, one or more of the features described in [A][1][b] can be combined with: the features described in [B], and one or more of the features described in one or both of [C][1] and [C][2], and one or more of the features described in [D][1], and one or more of the features described in one or more of [E][1], [E][2], and [E][3].

In some embodiments, one or more of the features described in [A][1][b] can be combined with: the features described in [B], and one or more of the features described in [C][1], and one or more of the features described in [D][1], and one or more of the features described in one or more of [E][1], [E][2], and [E][3].

In some embodiments, one or more of the features described in [A][1][d] can be combined with: the features described in [B], and one or more of the features described in one or both of [C][1] and [C][2], and one or more of the features described in one or more of [D][1], [D][2], [D][3], and [D][4], and one or more of the features described in one or more of [E][1], [E][2], and [E][3].

In some embodiments, one or more of the features described in [A][1][d] can be combined with: the features described in [B], and one or more of the features described in [C][1], and one or more of the features described in one or more of [D][1], [D][2], [D][3], and [D][4], and one or more of the features described in one or more of [E][1], [E][2], and [E][3].

In some embodiments, one or more of the features described in [A][1][d] can be combined with: the features described in [B], and one or more of the features described in one or both of [C][1] and [C][2], and one or more of the features described in one or both of [D][1] and [D][4], and one or more of the features described in one or more of [E][1], [E][2], and [E][3].

In some embodiments, one or more of the features described in [A][1][d] can be combined with: the features described in [B], and one or more of the features described in [C][1], and one or more of the features described in one or both of [D][1] and [D][4], and one or more of the features described in one or more of [E][1], [E][2], and [E][3].

In some embodiments, one or more of the features described in one or more of [A][2] can be combined with: the features described in [B], and/or one or more of the features described in one or both of [C][1] and [C][2] (e.g., [C][2]) and/or one or more of the features described in one or more of [D][1], [D][2], [D][3], and [D][4] (e.g., [D][4]) and/or one or more of the features described in one or more of [E][1], [E][2], and [E][3].

[II] n is 0 (i.e., in which A is Z is $R_1$—V-Cy-U—Ar'/Het'). Embodiments in which n is 0 can include one or more of the following features described throughout sections [AA] through [GG] below.

[AA] Variable Ar'/Het'

[1]

In some embodiments, Ar'/Het' is phenyl, pyridyl, or pyrimidinyl, each of which is optionally substituted with from 1-3 $R^p$; provided that the point of connection on said phenyl, pyridyl, or pyrimidinyl to U (i.e., the connection U—Ar'/Het' in formula I) and the point of connection on said phenyl, pyridyl, or pyrimidinyl to the amide carbonyl (i.e., the connection Ar'/Het'-C(=O) in formula I) do not result in 1,2-relation to one another on said phenyl, pyridyl, or pyrimidinyl (i.e., the points of connection to U and C(O) on said phenyl, pyridyl, or pyrimidinyl are not ortho with respect to one another).

In some embodiments, Ar'/Het' is phenyl, pyridyl, or pyrimidinyl, each of which is optionally substituted with from 1-3 $R^p$; wherein the point of connection on said phenyl, pyridyl, or pyrimidinyl to U (i.e., the connection U—Ar'/Het' in formula I) and the point of connection on said phenyl, pyridyl, or pyrimidinyl to the amide carbonyl (i.e., the connection Ar'/Het'-C(=O) in formula I) results in a 1,4-relation to one another on said phenyl, pyridyl, or pyrimidinyl (i.e., the points of connection to U and C(O) on said phenyl, pyridyl, or pyrimidinyl are para with respect to one another).

In some embodiments, Ar'/Het' is phenyl, which is optionally substituted with from 1-3 $R^p$; provided that the point of connection on said phenyl to U (i.e., the connection U—Ar'/Het' in formula I) and the point of connection on said phenyl to the amide carbonyl (i.e., the connection Ar'/Het'-C(=O) in formula I) does not result in a 1,2-relation to one another on said phenyl (i.e., the points of connection to U and C(O) on said phenyl are not ortho with respect to one another).

In some embodiments, Ar'/Het' is phenyl, which is optionally substituted with from 1-3 $R^p$; wherein the point of connection on said phenyl to U (i.e., the connection U—Ar'/Het' in formula I) and the point of connection on said phenyl to the amide carbonyl (i.e., the connection Ar'/Het'-C(=O) in formula I) results in a 1,4-relation to one another on said phenyl (i.e., the points of connection to U and C(O) on said phenyl are para with respect to one another).

[2]

In some embodiments, Ar'/Het' is a 5-membered heteroaryl selected from pyrazolyl, pyrrolyl, thiazolyl, thienyl, furanyl, imidazolyl, oxazolyl, oxadiazolyl, thiadiazolyl, isoxazolyl, isothiazolyl, each of which is optionally substituted with from 1-3 $R^p$; provided that the point of connection on said 5-membered heteroaryls to U (i.e., the connection U—Ar'/Het' in formula I) and the point of connection on said 5-membered heteroaryls to the amide carbonyl (i.e., the connection Ar'/Het'-C(=O) in formula I) do not result in 1,2-relation to one another on said 5-membered heteroaryls (i.e., the points of connection to U and C(O) on said 5-membered heteroaryl are not adjacent to one another).

[3]

In some embodiments, Ar'/Het' is a 8-, 9- or 10-membered bicyclic heteroaryl selected from benzothienyl, benzofuranyl, benzothioazolyl, benzoxazolyl, indolyl, isoindolonyl, indolizinyl, pyrrolopyrimidinyl, pyrazolopyridinyl, imidazopyridinyl, imidazopyridazinyl, triazolopyridinyl, imidazothiazolyl, imidazooxazolyl, quinolinyl, and naphthyridinyl; each of which is optionally substituted with from 1-3 $R^p$.

In certain embodiments, Ar'/Het' is a 8-, 9- or 10-membered bicyclic heteroaryl selected from indolizinyl, pyrrolopyrimidinyl, pyrazolopyridinyl, imidazopyridinyl, imidazopyridazinyl, triazolopyridinyl, imidazothiazolyl, and imidazooxazolyl; each of which is optionally substituted with from 1-3 $R^p$.

[BB] Variable Cy

[1]

In some embodiments, Cy is a saturated heterocyclyl including 4-10 (e.g., 4-8, 4-6) ring atoms, each of which is optionally substituted with from 1-3 $R^x$ (wherein each occurrence of $R^x$ is independently selected from F, OH, C1-C6 alkyl, fluoro C1-C6 alkyl, C3-C6 cycloalkyl, C1-C6 alkoxy C1-C6 fluoroalkoxy, and cyano), in which from 1-3 heteroatoms are independently selected from O, N—H, $NR^{x'}$ (wherein $R^{x'}$ is defined as $R^{q''}$), and $S(O)_m$ (m=0-2); wherein when the heterocyclyl contains a secondary amine as part of its structure, then:
   (i) V is linked through the nitrogen of the secondary amine portion of the heterocyclyl; and
   (ii) U is linked to Cy via a Cy ring carbon atom; wherein the bond between U and the Cy ring carbon is a single or double bond; and (iii) V-Cy and Cy-U do not lead to 1,2 relationship (i.e. the Cy ring carbon atom that is attached to U is not adjacent to Cy ring nitrogen atom that is attached to V).

In certain embodiments, Cy is a heterocyclyl that contains a secondary amine as part of its structure.

In certain embodiments, Cy is azetidinyl, pyrrolidinyl, piperidinyl, azepanyl, diazepanyl, isoxazolidinyl, thiazolidinonyl, imidazolidinonyl, pyrrolidinonyl, azabicyclooctyl (aka. tropanyl), azabicycloheptanyl, or azabicyclohexanyl.

In certain embodiments, Cy is azetidinyl, pyrrolidinyl or piperidinyl (e.g., azetidinyl or piperidinyl).

[2]

In some embodiments, Cy is cycloalkyl (e.g., cyclobutyl, cyclopentyl, cyclohexyl).

[CC] Variable V

In some embodiments, V is —V'—C($R^y$)$_2$— or —C($R^y$)$_2$—V'—.

In some embodiments, each occurrence of $R^y$ is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy C1-C6 fluoroalkoxy, and cyano.

In certain embodiments, each occurrence of $R^y$ is independently selected from H, F, C1-C6 alkyl, and C3-C6 cycloalkyl.

In certain embodiments, each occurrence of $R^y$ is H.

In some embodiments, V' is a bond.

[DD] Variable U

In some embodiments, U is =C$R^r$. $R^r$ is hydrogen.

In certain embodiments, U is —U'—C($R^s$)$_2$— or —C($R^s$)$_2$—U'—.

In certain embodiments, each occurrence of $R^s$ is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy C1-C6 fluoroalkoxy, and cyano.

In certain embodiments, each occurrence of $R^s$ is independently selected from H, F, C1-C6 alkyl, and C3-C6 cycloalkyl.

In certain embodiments, each occurrence of $R^s$ is H.

In some embodiments, U' is a bond.

[EE] Variable R1

[1]

In some embodiments, R1 is C6-C10 aryl, which is optionally substituted with from 1-3 $R^q$. In certain embodiments, R1 is phenyl or naphthyl (e.g., phenyl), which is optionally substituted with from 1-3 $R^q$ (in embodiments, each $R^q$ is independently selected from F, OH, C1-C6 alkyl, fluoro(C1-C6) alkyl C3-C6 cycloalkyl, $NH_2$, C1-C6 alkoxy, C1-C6 fluoroalkoxy, and cyano).

[2]

In some embodiments, R1 is monocyclic or bicyclic heteroaryl including from 5-10 ring atoms, which is optionally substituted with from 1-3 $R^q$; wherein from 1-4 of the ring atoms is/are a heteroatom independently selected from O, N, N—H, N—$R^q$, and S.

In certain embodiments, R1 is monocyclic heteroaryl, such as pyridyl.

In other embodiments, R1 is bicyclic heteroaryl, such as those that are fully aromatic such as indolyl and the like.

In still other embodiments, R1 is bicyclic heteroaryl that contains a bridgehead nitrogen ring atom and optionally other heteroatom ring atoms, such as indolizinyl, pyrrolopyrimidinyl, pyrazolopyridinyl, imidazopyridinyl, imidazopyriazinyl, triazolopyridinyl, imidazothiazolyl, imidazooxazolyl.

Other examples of R1 heteroaryl groups include, without limitation, pyrazolyl, pyrrolyl, 2-oxo-indolyl, quinolinyl, isoquinolinyl, tetrahydro-isoquinolinyl, benzofuranyl, benzodioxanyl, benzodioxolyl (aka. methylenedioxyphenyl) and corresponding difluoro ($CF_2$) analog, thiazolyl, 2-oxopyridinyl, pyridinyl N-oxide, pyrimidinyl, thienyl, furanyl, oxazolyl, isoxazolyl, pyridazinyl, imidazolyl, pyrazinyl, isothiazolyl, 1,2-thiazinyl-1,1-dioxide, benzimidazolyl, thiadiazolyl, benzopyranyl, benzothiazolyl, benzotriazolyl, benzoxazolyl, benzothienyl, oxadiazolyl, triazolyl, tetrazolyl, dioxoindolyl (isatin), phthalimido and the dihydro and tetrahydro congeners of the fully unsaturated ring systems.

[3]

In some embodiments, R1 is heterocyclyl including from 4-10 ring atoms, which is optionally substituted with from 1-3 $R^q$; wherein from 1-4 of the ring atoms is/are a heteroatom independently selected from O, N, N—H, N—$R^q$, and S (e.g., bicyclic heterocyclyl containing a bridgehead nitrogen ring atom and optionally other heteroatom ring atoms).

Examples of R1 heterocyclyl groups include, without limitation, piperidinyl, morpholinyl, pyrrolidinyl, azetidinyl, azepanyl, isoxazolidinyl, oxazolidinyl, thiazolidinyl, imidazolinyl, quinuclidinyl, isothiazolidinyl, tetrahydrofuranyl, tetrahydropyranyl, thiamorpholinyl, thiamorpholinyl sulfoxide, thiamorpholinyl sulfone, dioxanyl, tropanyl and other bridged bicyclic amines, quiniclidinyl.

[4]

In some embodiments, R1 is H.

[FF] Variables R2 and R3

[1]

In some embodiments, R2 is a substituent other than hydrogen (e.g., phenyl, substituted phenyl, thienyl, thiazolyl, and pyrazol-1-yl), and R3 is hydrogen. In certain embodiments, the compounds can exhibit selectivity for HDAC 1 and/or 2.

[2]

In some embodiments, R2 is hydrogen, and R3 is a substituent other than hydrogen (e.g., fluoro). In certain embodiments, the compounds can exhibit selectivity for HDAC 3.

[3]

In some embodiments, each of R2 and R3 is hydrogen.

[GG] Non-limiting Combinations of [II][AA] through [II][FF] (i.e., n=0)

In some embodiments, one or more of the features described in one or more of [AA][1], [AA][2], and [AA][3] can be combined with: one or more of the features described in [DD], and/or one or more of the features described in [CC], and/or one or more of the features described in one or both of [BB][1] and [BB][2], and/or one or more of the features described in one or more of [EE][1], [EE][2], [EE][3], and [EE][4], and/or one or more of the features described in one or more of [FF][1], [FF][2], and [FF][3].

In some embodiments, one or more of the features described in one or more of [AA][1], [AA][2], and [AA][3] can be combined with: one or more of the features described in [DD], and one or more of the features described in [CC], and one or more of the features described in one or both of [BB][1] and [BB][2], and one or more of the features described in one or more of [EE][1], [EE][2], [EE][3], and [EE][4], and one or more of the features described in one or more of [FF][1], [FF][2], and [FF][3].

In some embodiments, one or more of the features described in [AA][1], can be combined with: one or more of the features described in [DD], and one or more of the features described in [CC], and one or more of the features described in one or both of [BB][1] and [BB][2], and one or more of the features described in one or more of [EE][1],

[EE][2], [EE][3], and [EE][4], and one or more of the features described in one or more of [FF][1], [FF][2], and [FF][3].

In some embodiments, one or more of the features described in one or more of [AA][1], [AA][2], and [AA][3] can be combined with: one or more of the features described in [DD], and one or more of the features described in [CC], and one or more of the features described in [BB][1], and one or more of the features described in one or more of [EE][1], [EE][2], [EE][3], and [EE][4], and one or more of the features described in one or more of [FF][1], [FF][2], and [FF][3].

In some embodiments, one or more of the features described in one or more of [AA][1], [AA][2], and [AA][3] can be combined with: one or more of the features described in [DD], and one or more of the features described in [CC], and one or more of the features described in one or both of [BB][1] and [BB][2], and one or more of the features described in [EE][2], and one or more of the features described in one or more of [FF][1], [FF][2], and [FF][3].

In some embodiments, one or more of the features described in [AA][1] can be combined with: one or more of the features described in [DD], and one or more of the features described in [CC], and one or more of the features described in [BB][1], and one or more of the features described in [EE][2], and one or more of the features described in one or more of [FF][1], [FF][2], and [FF][3].

In certain embodiments, n is 1, and X is —Y—[C(R$^a$)$_2$]$_a$-A-[C(R$^b$)$_2$]$_b$—B—.

In certain embodiments, n is 1, and X is —Y—[C(R$^a$)$_2$]$_a$-A-[C(R$^b$)$_2$]$_b$—B—, and Y is CR$^c$=CR$^d$. Embodiments can include any one or more of the features described herein. For example, one or both of the following: R1 is C6-C10 aryl (e.g., phenyl), which is optionally substituted with from 1-3 R$^o$; and Ar/Het is 5 membered heteroaromatic selected from pyrazolyl, thiazolyl, oxazolyl, imidazolyl, isoxazolyl, isothiazolyl, thiadiazolyl, oxadiazolyl, and 1,2,4-triazolyl (in some embodiments, Ar/Het is other than 1,2,4-triazolyl and/or furanyl), e.g., Ar/Het is pyrazolyl. In embodiments, each of R4 and R5 is hydrogen; and/or one or more of the following: (i) R2 is a substituent other than hydrogen (e.g., phenyl, substituted phenyl, thienyl, thiazolyl, and pyrazol-1-yl), and R3 is hydrogen, in certain embodiments, the compounds can exhibit selectivity for HDAC 1 and/or 2; (ii) R2 is hydrogen, and R3 is a substituent other than hydrogen (e.g., fluoro), in certain embodiments, the compounds can exhibit selectivity for HDAC 3; and (iii) each of R2 and R3 is hydrogen.

In certain embodiments, n is 1, and X is —Y—[C(R$^a$)$_2$]$_a$-A-[C(R$^b$)$_2$]$_b$—B—, and Y is O or NR$^e$ (e.g., Y is O). Embodiments can include any one or more of the features described herein. For example, one or both of the following: R1 is C6-C10 aryl (e.g., phenyl), which is optionally substituted with from 1-3 R$^o$; and Ar/Het is 5 membered heteroaromatic selected from pyrazolyl, thiazolyl, oxazolyl, imidazolyl, isoxazolyl, isothiazolyl, thiadiazolyl, oxadiazolyl, and 1,2,4-triazolyl (in some embodiments, Ar/Het is other than 1,2,4-triazolyl and/or furanyl), e.g., Ar/Het is pyrazolyl. In embodiments, each of R4 and R5 is hydrogen; and/or one or more of the following: (i) R2 is a substituent other than hydrogen (e.g., phenyl, substituted phenyl, thienyl, thiazolyl, and pyrazol-1-yl), and R3 is hydrogen, in certain embodiments, the compounds can exhibit selectivity for HDAC 1 and/or 2; (ii) R2 is hydrogen, and R3 is a substituent other than hydrogen (e.g., fluoro), in certain embodiments, the compounds can exhibit selectivity for HDAC 3; and (iii) each of R2 and R3 is hydrogen.

In certain embodiments, n is 1, and Ar/Het is a bicyclic 8-, 9-, or 10-membered azabridged heteroaromatic such as indolizinyl, pyrrolopyrimidinyl, pyrazolopyridinyl, imidazopyridinyl, imidazopyridazinyl, triazolopyridinyl, imidazothiazolyl, imidazooxazolyl, 1,2,4-triazolothiazolyl, and 1,2,4-triazolooxazolyl. Embodiments can include any one or more of the features described herein. For example, X is a bond and R1 is H. In embodiments, each of R4 and R5 is hydrogen; and/or one or more of the following: (i) R2 is a substituent other than hydrogen (e.g., phenyl, substituted phenyl, thienyl, thiazolyl, and pyrazol-1-yl), and R3 is hydrogen, in certain embodiments, the compounds can exhibit selectivity for HDAC 1 and/or 2; (ii) R2 is hydrogen, and R3 is a substituent other than hydrogen (e.g., fluoro), in certain embodiments, the compounds can exhibit selectivity for HDAC 3; and (iii) each of R2 and R3 is hydrogen.

In certain embodiments, n is 0, and U is =CR$^r$ (e.g., R$^r$ is hydrogen). Embodiments can include any one or more of the features described herein. For example, one or both of the following: Ar'/Het' is phenyl, which is optionally substituted with from 1-3 R$^p$; and having the provisions described elsewhere; Cy is a heterocyclyl (e.g., a heterocyclyl that contains a secondary amine as part of its structure). In embodiments, one or more of the following apply: (i) R2 is a substituent other than hydrogen (e.g., phenyl, substituted phenyl, thienyl, thiazolyl, and pyrazol-1-yl), and R3 is hydrogen, in certain embodiments, the compounds can exhibit selectivity for HDAC 1 and/or 2; (ii) R2 is hydrogen, and R3 is a substituent other than hydrogen (e.g., fluoro), in certain embodiments, the compounds can exhibit selectivity for HDAC 3; and (iii) each of R2 and R3 is hydrogen.

Definitions

The term "mammal" includes organisms, which include mice, rats, cows, sheep, pigs, rabbits, goats, horses, monkeys, dogs, cats, and humans.

"An effective amount" refers to an amount of a compound that confers a therapeutic effect (e.g., treats, e.g., controls, relieves, ameliorates, alleviates, or slows the progression of; or prevents, e.g., delays the onset of or reduces the risk of developing, a disease, disorder, or condition or symptoms thereof) on the treated subject. The therapeutic effect may be objective (i.e., measurable by some test or marker) or subjective (i.e., subject gives an indication of or feels an effect). An effective amount of the compound described above may range from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

The term "halo" or "halogen" refers to any radical of fluorine, chlorine, bromine or iodine.

In general, and unless otherwise indicated, substituent (radical) prefix names are derived from the parent hydride by either (i) replacing the "ane" in the parent hydride with the suffix "yl;" or (ii) replacing the "e" in the parent hydride with the suffix "yl;" (here the atom(s) with the free valence, when specified, is (are) given numbers as low as is consistent with any established numbering of the parent hydride). Accepted contracted names, e.g., furyl, pyridyl, and piperidyl, and trivial names, e.g., phenyl and thienyl are also used herein throughout. Conventional numbering/lettering systems are also adhered to for substituent numbering.

The following definitions are used, unless otherwise described. Specific and general values listed below for radicals, substituents, and ranges, are for illustration only;

they do not exclude other defined values or other values within defined ranges for the radicals and substituents. Alkyl, alkoxy, and the like denote both straight and branched groups.

As used herein, the term "alkyl," employed alone or in combination with other terms, refers to a saturated hydrocarbon group that may be straight-chain or branched. In some embodiments, the alkyl group contains 1 to 12, 1 to 8, or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like. In some embodiments, the alkyl moiety is methyl, ethyl, n-propyl, isopropyl, n-butyl, isobutyl, tert-butyl, n-pentyl, isopentyl, neopentyl, n-hexyl, or 2,4,4-trimethylpentyl.

Throughout the definitions, the term "Cy-Cz" (e.g., C1-C6 and the like) is used, wherein y and z are integers and indicate the number of carbons, wherein y-z indicates a range which includes the endpoints.

As referred to herein, the term "alkoxy group" refers to a group of formula —O(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy.

As used herein, the term "aryl," employed alone or in combination with other terms, refers to a monocyclic aromatic hydrocarbon moiety or a polycyclic hydrocarbon moiety (e.g., having 2, 3 or 4 fused linked rings) that includes at least one aromatic ring. Examples include, but are not limited to, phenyl, 1-naphthyl, 2-naphthyl, indanyl and tetralinyl. In some embodiments, aryl groups have from 6 to 10 carbon atoms.

As referred to herein, "heteroaryl" refers to an aromatic monocyclic or fused bicyclic ring that includes at least one aromatic ring, each of which containing at least one (typically one to about three) nitrogen, oxygen, or sulfur ring atoms (independently selected when more than one is present). Examples of heteroaryl groups include, but are not limited to pyridyl, pyrazolyl, pyrrolyl, 2-oxo-indolyl, quinolinyl, isoquinolinyl, tetrahydro-isoquinolinyl, benzofuranyl, indolyl, benzodioxanyl, benzodioxolyl (aka. methylenedioxyphenyl) and corresponding difluoro ($CF_2$) analog, thiazolyl, 2-oxopyridinyl, pyridinyl N-oxide, pyrimidinyl, thienyl, furanyl, oxazolyl, isoxazolyl, pyridazinyl, imidazolyl, pyrazinyl, isothiazolyl, 1,2-thiazinyl-1,1-dioxide, benzimidazolyl, thiadiazolyl, benzopyranyl, benzothiazolyl, benzotriazolyl, benzoxazolyl, benzothienyl, oxadiazolyl, triazolyl, tetrazolyl, dioxoindolyl (isatin), phthalimido; heteroaryls that contain a bridgehead nitrogen ring atom and optionally other heteroatom ring atoms, such as indolizinyl, pyrrolopyrimidinyl, pyrazolopyridinyl, imidazopyridinyl, imidazopyriazinyl, triazolopyridinyl, imidazothiazolyl, imidazooxazolyl); and the dihydro and tetrahydro congeners of the fully unsaturated ring systems.

As used herein, the phrase "optionally substituted" means unsubstituted (e.g., substituted with a H) or substituted. As used herein, the term "substituted" means that a hydrogen atom is removed and replaced by a substitutent. It is understood that substitution at a given atom is limited by valency. The use of a substituent (radical) prefix name such as alkyl without the modifier "optionally substituted" or "substituted" is understood to mean that the particular substituent is unsubstituted. However, the use of "fluoro Cy-Cz alkyl" without the modifier "optionally substituted" or "substituted" is still understood to mean an alkyl group, in which at least one hydrogen atom is replaced by fluoro.

Unless indicated otherwise, the nomenclature of substituents that are not explicitly defined herein are arrived at by naming the terminal portion of the functionality followed by the adjacent functionality toward the point of attachment. In generally, the point of attachment for a substituent is indicated by the last term in the group. For example, (heterocyclyl)-(C1-C6) alkyl refers to a moiety of heteroarylalkylene-, wherein the alkylene linker has 1 to 6 carbons, and the substituent is attached through the alkylene linker.

As used herein, the term "cycloalkyl," employed alone or in combination with other terms, refers to a saturated, cyclic hydrocarbon moiety. Exemplary cycloalkyl groups include, without limitation, cyclopropyl, cyclobutyl, cyclopentyl, cyclohexyl, and cycloheptyl.

As used herein, the term "cyano," employed alone or in combination with other terms, refers to a group of formula —CN, wherein the carbon and nitrogen atoms are bound together by a triple bond.

As used herein, the term "halo Cy-Cz alkyl" and the like employed alone or in combination with other terms, refers to an alkyl group having from one halogen atom to 2n+1 halogen atoms which may be the same or different, where "n" is the number of carbon atoms in the alkyl group. In some embodiments, the halogen atoms are fluoro atoms.

As used herein, "haloalkoxy," employed alone or in combination with other terms, refers to a group of formula —O-haloalkyl. An example haloalkoxy group is $OCF_3$. In some embodiments, the halogen atoms are fluoro atoms.

As used herein, the term "heterocyclyl" employed alone or in combination with other terms, refers to a saturated ring system, which has carbon ring atoms and at least one heteroatom ring atom selected from nitrogen, sulfur, and oxygen (independently selected when more than one is present). When the heterocyclyl group contains more than one heteroatom, the heteroatoms may be the same or different. Heterocyclyl groups can include mono- or bicyclic (e.g., having 2 fused rings) ring systems. Heterocyclyl groups can also include bridgehead heterocycloalkyl groups. As used herein, "bridgehead heterocyclyl group" refers to a heterocyclyl moiety containing at least one bridgehead heteroatom (e.g., nitrogen). In some embodiments, the carbon atoms or hetereoatoms in the ring(s) of the heterocycloalkyl group can be oxidized to form a carbonyl, or sulfonyl group (or other oxidized linkage) or a nitrogen atom can be quaternized.

As to any of the above groups that contain one or more substituents, it is understood, of course, that such groups do not contain any substitution or substitution patterns that are sterically impractical and/or synthetically unfeasible. In addition, the compounds of this invention include all stereochemical isomers arising from the substitution of these compounds.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

Thus, for ease of exposition, it is also understood that where in this specification, a group is defined by "as defined anywhere herein" (or the like), the definitions for that particular group include the first occurring and broadest generic definition as well as any sub-generic and specific definitions delineated anywhere in this specification. Also, for ease of exposition, the definition "substituent other than hydrogen" refers collectively to the non-hydrogen possibilities for that particular variable.

BRIEF DESCRIPTION OF THE DRAWINGS

FIG. 1 is a bar graph shows the effect of compounds on long-term memory for object recognition. The data is presented as discrimination index between known and novel object as a function of compound and dose. In the leftmost cluster of bars, the dosages represented from left to right are (0, 3, 10, 30 mg/kg); in the center and rightmost cluster of bars, the dosages represented from left to right are (3, 10, 30 mg/kg).

DETAILED DESCRIPTION

Compounds of formula (I) described herein may contain one or more asymmetric centers and thus occur as racemates and racemic mixtures, single enantiomers, individual diastereomers and diastereomeric mixtures. While shown without respect to the stereochemistry in formula (I), the present invention includes such optical isomers (enantiomers) and diastereomers; as well as the racemic and resolved, enantiomerically pure R and S stereoisomers; as well as other mixtures of the R and S stereoisomers and pharmaceutically acceptable salts thereof. The use of these compounds is intended to cover the racemic mixture or either of the chiral enantiomers.

Compounds of formula (I) described herein may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the present invention.

One skilled in the art will also recognize that it is possible for tautomers to exist for the compounds described herein. The invention includes all such tautomers even though not shown in the formulas herein. All such isomeric forms of such compounds are expressly included in the present invention.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds described herein also include the various hydrate and solvate forms of the compounds.

Compounds described herein can also include all isotopes of atoms occurring in the intermediates or final compounds. Isotopes include those atoms having the same atomic number but different mass numbers. For example, isotopes of hydrogen include tritium and deuterium.

The compounds described herein also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

In some embodiments, the compounds are prodrugs. As used herein, "prodrug" refers to a moiety that releases a compound described herein when administered to a patient. Prodrugs can be prepared by modifying functional groups present in the compounds in such a way that the modifications are cleaved, either in routine manipulation or in vivo, to the parent compounds. Examples of prodrugs include compounds as described herein that contain one or more molecular moieties appended to a hydroxyl, amino, sulfhydryl, or carboxyl group of the compound, and that when administered to a patient, cleave in vivo to form the free hydroxyl, amino, sulfhydryl, or carboxyl group, respectively. Examples of prodrugs include, but are not limited to, acetate, formate and benzoate derivatives of alcohol and amine functional groups in the compounds described herein. Preparation and use of prodrugs is discussed in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

Synthesis of Compounds of Formula (I)

The compounds described herein can be prepared in a variety of ways known to one skilled in the art of organic synthesis. The compounds described herein can be synthesized using the methods as hereinafter described below, together with synthetic methods known in the art of synthetic organic chemistry or variations thereon as appreciated by those skilled in the art.

Compounds of the present invention can be conveniently prepared in accordance with the procedures outlined in the Examples section, from commercially available starting materials, compounds known in the literature, or readily prepared intermediates, by employing conventional synthetic methods and procedures known to those skilled in the art. Conventional synthetic methods and procedures for the preparation of organic molecules and functional group transformations and manipulations can be readily obtained from the relevant scientific literature or from standard textbooks in the field. It will be appreciated that, where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations useful in synthesizing the compounds described herein are known in the art and include, for example, those such as described in R. C. Larock, *Comprehensive Organic Transformations*, 2d. ed., Wiley-VCH Publishers (1999); P. G. M. Wuts and T. W. Greene, *Protective Groups in Organic Synthesis*, 4th Ed., John Wiley and Sons (2007); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof. Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts P G M and Greene T W, 2006, Greene's Protective Groups in Organic Synthesis, Fourth Edition, John Wiley & Sons, Inc., Hoboken, N.J., USA, which is incorporated herein by reference in its entirety. Adjustments to the protecting groups and formation and cleavage methods described herein may be adjusted as necessary in light of the various substituents.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent freezing temperature to the solvent boiling temperature. A given reaction can be carried out in one solvent or a mixture of more than one solvent. Depending on the particular reaction step, suitable solvents for a particular reaction step can be selected.

The processes described herein can be monitored according to any suitable method known in the art. For example, product formation can be monitored by spectroscopic means, such as nuclear magnetic resonance spectroscopy (e.g., $^1$H and/or $^{13}$C NMR) infrared spectroscopy, spectrophotometry (e.g., UV-visible), or mass spectrometry, or by chromatography such as high performance liquid chromatography (HPLC) or thin layer chromatography.

The compounds described herein can be separated from a reaction mixture and further purified by a method such as column chromatography, high-performance liquid chromatography (HPLC), or recrystallization.

One of skill in the art will recognize that there are additional methods of producing the compounds of formula (I) in addition to those described in the Examples section.

Use

A histone deacetylase (HDAC), as described herein, can be any polypeptide having features characteristic of polypeptides that catalyze the removal of the acetyl group (deacetylation) from acetylated target proteins. Features characteristic of HDACs are known in the art (see, for example, Finnin et al., 1999, Nature, 401:188). Thus, an HDAC can be a polypeptide that represses gene transcription by deacetylating the ϵ-amino groups of conserved lysine residues located at the N-termini of histones, e.g., H3, H4, H2A, and H2B, which form the nucleosome. HDACs also deacetylate other proteins such as p53, E2F, α-tubulin, and MyoD (see, for example, Annemieke et al., 2003, Biochem. J., 370:737). HDACs can also be localized to the nucleus and certain HDACs can be found in both the nucleus and also the cytoplasm.

Compounds of formula (I) described herein may interact with any HDAC. In some embodiments, the compounds of formula (I) described herein will have at least about 2-fold (e.g., at least about 5-fold, 10-fold, 15-fold, or 20-fold) greater activity to inhibit one or more class I HDACS (e.g., HDAC1, HDAC2, or HDAC3) as compared to one or more other HDACs (e.g., one or more HDACs of class IIa, IIb, or IV).

The invention features a method of treating a cancer in patient in need thereof, comprising administering a therapeutically effective amount of an HDAC inhibitor as described herein, or pharmaceutically, acceptable salt thereof. In some embodiments, the cancer is a solid tumor, neoplasm, carcinoma, sarcoma, leukemia, or lymphoma. In some embodiments, leukemias include acute leukemias and chronic leukemias such as acute lymphocytic leukemia (ALL), acute myeloid leukemia, chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (fITLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genitorurinary cancers (e.g., prostate, bladder, renal, uterine, ovarian, testicular, rectal and colon), lung cancer, breast cancer.

In some embodiments, the cancer is (a) Cardiac: sarcoma (angiosarcoma, fibrosarcoma, rhabdomyosarcoma, liposarcoma), myxoma, rhabdomyoma, fibroma, lipoma and teratoma; (b) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; (c) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (d) Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (e) Liver: hepatoma (hepatocellular carcinoma), cholangiocarcinoma, hepatoblastoma, angiosarcoma, hepatocellular adenoma, hemangioma; (f) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; (g) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord (neurofibroma, meningioma, glioma, sarcoma); (h) Gynecological: uterus (endometrial carcinoma), cervix (cervical carcinoma, pre-tumor cervical dysplasia), ovaries (ovarian carcinoma, serous cystadenocarcinoma, mucinous cystadenocarcinoma), unclassified carcinoma (granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma), embryonal rhabdomyosarcoma, fallopian tubes (carcinoma); (i) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, .non-Hodgkin's lymphoma (malignant lymphoma); (j) Skin: malignant melanoma, basal cell carcinoma, squamous cell carcinoma, Karposi's sarcoma, moles dysplastic nevi, lipoma, angioma, dermatofibroma, keloids, psoriasis; and (k) Adrenal glands: neuroblastoma conditions.

In another aspect, the present invention provides a method of treating a inflammatory disorder in patient in need thereof, comprising administering a therapeutically effective amount of a compound of formula (I) as described herein, or pharmaceutically, acceptable salt thereof. In some embodiments, the inflammatory disorder is an acute and chronic inflammatory disease, autoimmune disease, allergic disease, disease associated with oxidative stress, and diseases characterized by cellular hyperproliferation. Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemorrhagic shock; hyperalgesia: inflammatory bowel disease; multiple sclerosis; myopathies (e.g., muscle protein metabolism, esp. in sepsis); osteoarthritis; osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes.

Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

In another aspect, the present invention provides a method of preventing or treating a memory-related disorder in patient in need thereof, comprising administering a therapeutically effective amount of a compound of formula (I) as described herein, or pharmaceutically, acceptable salt thereof. Compounds of formula (I) can be used to treat patients with memory impairments associated with direct cognitive disorders such as amnesia, dementia and delirium; anxiety disorders such as phobias, panic disorders, psychosocial stress (e.g. as seen in disaster, catastrophe or violence victims), obsessive-compulsive disorder, generalized anxiety disorder and post-traumatic stress disorder; mood disorders such as depression and bipolar disorder; and psychotic disorders such as schizophrenia and delusional disorder. Memory impairment, a hallmark of neurodegenerative diseases such as, but not limited to, Parkinson's, Alzheimer's, Huntington's, amyotrophic lateral sclerosis (ALS), spinocerebellar ataxia, as well as aging, can also be treated by using compounds of formula (I). In addition, compounds of the invention can be used to treat drug addiction through extinction of drug-seeking behavior.

In a further aspect, this application features methods of treating a neurological condition (e.g., Friedreich's ataxia (FRDA), myotonic dystrophy, spinal muscular atrophy, fragile X syndrome, Huntington's disease, a spinocerebellar ataxia, Kennedy's disease, amyotrophic lateral sclerosis, spinal and bulbar muscular atrophy, Alzheimer's disease or schizophrenia, bipolar disorder, and related diseases) that include administering a compound of formula (I) described herein to a patient having a neurological condition.

In another aspect, this application features the use of a compound of formula (I) described herein in the preparation of a medicament for the treatment or prevention of a neurological condition (e.g., Friedreich's ataxia, myotonic dystrophy, spinal muscular atrophy, fragile X syndrome, Huntington's disease, a spinocerebellar ataxia, Kennedy's disease, amyotrophic lateral sclerosis, spinal and bulbar muscular atrophy, or Alzheimer's disease); a memory-affecting condition or disease, a cancer; or an inflammatory disorder, or a *Plasmodium falciparum* infection (e.g., malaria).

In a further aspect, the application provides a kit for the treatment or prevention of a disorder selected from a neurological disorder (e.g., Friedreich's ataxia, myotonic dystrophy, spinal muscular atrophy, fragile X syndrome, Huntington's disease, a spinocerebellar ataxia, Kennedy's disease, amyotrophic lateral sclerosis, spinal and bulbar muscular atrophy, or Alzheimer's disease), a memory-affecting condition or disease, a cancer, an inflammatory disorder, or a *Plasmodium falciparum* infection (e.g., malaria) in a patient in need thereof, comprising (i) a compound of formula (I) described herein or a pharmaceutically acceptable salt thereof; and (ii) instructions comprising a direction to administer said compound to said patient.

In some embodiments of the above methods, the methods further include assaying the activity of the candidate compound to increase expression of one or more genes whose expression is decreased in the neurological condition (e.g., frataxin, huntingtin, brain derived neurotrophic factor (BDNF), peroxisome proliferator-activated receptor-gamma, coactivator 1, alpha (PGC1A), ataxin, fragile X mental retardation (FMR1), dystrophia myotonica protein kinase (DMPK), or androgen receptor). In some embodiments, the activity of the candidate compound to increase expression of one or more genes whose expression is decreased in the neurological condition is measured in an animal, e.g., an animal model of the neurological condition.

In some embodiments of the above methods, the method is repeated for a plurality of test compounds (e.g., at least 10, 20, 50, 100, 200, 500, or 1000 test compounds).

In another aspect, this application features methods of treating a neurological condition (e.g., Friedreich's ataxia, myotonic dystrophy, spinal muscular atrophy, fragile X syndrome, Huntington's disease, spinocerebellar ataxias, Kennedy's disease, amyotrophic lateral sclerosis, spinal and bulbar muscular atrophy, or Alzheimer's disease) that include performing any of the above methods, formulating the candidate compound in a pharmaceutical composition, and administering the pharmaceutical composition to a patient having a neurological condition.

HDAC inhibitors have been shown to have antimalarial activity (Andrews et al., 2000, Int. J. Parasitol., 30:761-768; Andrews et al., Antimicrob. Agents Chemother., 52:1454-61). The present invention provides methods of treating a *Plasmodium falciparum* infection (e.g., malaria) in a patient in need thereof.

Pharmaceutical Compositions

HDAC inhibitors can be administered neat or formulated as pharmaceutical compositions. Pharmaceutical compositions include an appropriate amount of the HDAC inhibitor in combination with an appropriate carrier and optionally other useful ingredients.

Acceptable salts of the formula (I) compounds described herein include, but are not limited to, those prepared from the following acids: alkyl, alkenyl, aryl, alkylaryl and alkenylaryl mono-, di- and tricarboxylic acids of 1 to 20 carbon atoms, optionally substituted by 1 to 4 hydroxyls; alkyl, alkenyl, aryl, alkylaryl and alkenylaryl mono-, di- and trisulfonic acids of 1 to 20 carbon atoms, optionally substituted by 1 to 4 hydroxyls; dibasic acids and mineral acids. Examples include hydrochloric; hydrobromic; sulfuric; nitric; phosphoric; lactic (including (+)-L-lactic, (+/−)-DL-lactic); fumaric; glutaric; maleic; acetic; salicyclic; p-toluenesulfonic; tartaric (including (+)-L-tartaric); citric; methanesulfonic; formic; malonic; succinic; naphthalene-2-sulfonic; and benzenesulfonic acids. Also, pharmaceutically-acceptable salts can be prepared as amine salts, ammonium salts, or alkaline metal or alkaline earth salts, such as sodium, potassium or calcium salts of the carboxylic acid group. These are formed from alkaline metal or alkaline earth metal bases or from amine compounds.

Pharmaceutical compositions of formula (I) compounds described herein suitable for oral administration can be in the form of (1) discrete units such as capsules, sachets, tablets, or lozenges each containing a predetermined amount of the HDAC inhibitor; (2) a powder or granules; (3) a bolus, electuary, or paste; (4) a solution or a suspension in an aqueous liquid or a non-aqueous liquid; or (5) an oil-in-water liquid emulsion or a water-in-oil liquid emulsion. Compositions suitable for topical administration in the mouth, for example buccally or sublingually, include lozenges. Compositions suitable for parenteral administration include aqueous and non-aqueous sterile suspensions or injection solutions. Compositions suitable for rectal administration can be presented as a suppository.

Pharmaceutical compositions of formula (I) compounds described herein can be formulated using a solid or liquid carrier. The solid or liquid carrier should be compatible with the other ingredients of the formulation and not deleterious to the recipient. If the pharmaceutical composition is in tablet form, then the HDAC inhibitor is mixed with a carrier having the necessary compression properties in suitable proportions and compacted in the shape and size desired. If the composition is in powder form, the carrier is a finely divided solid in admixture with the finely divided active ingredient. The powders and tablets can contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. A solid carrier can include one or more substances that can act as flavoring agents, lubricants, solubilizers, suspending agents, fillers, glidants, compression aids, binders or tablet-disintegrating agents. A suitable carrier can also be an encapsulating material.

If the composition is a solution, suspension, emulsion, syrup, elixir, or pressurized composition, then liquid carriers can be used. In this case, the HDAC inhibitor is dissolved or suspended in a pharmaceutically acceptable liquid carrier. Suitable examples of liquid carriers for oral and parenteral administration include (1) water; (2) alcohols, e.g. monohydric alcohols and polyhydric alcohols such as glycols, and their derivatives; and (3) oils, e.g. fractionated coconut oil and arachis oil. For parenteral administration, the carrier can also be an oily ester such as ethyl oleate and isopropyl myristate. Liquid carriers for pressurized compositions include halogenated hydrocarbon or other pharmaceutically acceptable propellants. The liquid carrier can contain other suitable pharmaceutical additives such as solubilizers; emulsifiers; buffers; preservatives; sweeteners; flavoring agents; suspending agents; thickening agents; colors; viscosity regulators; stabilizers; osmo-regulators; cellulose derivatives such as sodium carboxymethyl cellulose; antioxidants; and bacteriostatics. Other carriers include those used for formulating lozenges such as sucrose, acacia, tragacanth, gelatin and glycerin as well as those used in formulating suppositories such as cocoa butter or polyethylene glycol.

If the composition is to be administered intravenously or intraperitoneally by infusion or injection, solutions of the HDAC inhibitor can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The composition suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium as described above. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin. Sterile injectable solutions are prepared by incorporating the HDAC inhibitor in the required amount in the appropriate solvent with some of the other ingredients enumerated above, as required, followed by filter sterilization. In the case of sterile powders for the preparation of sterile injectable solutions, the preferred methods of preparation are vacuum drying and the freeze-drying techniques, which yield a powder of the HDAC inhibitor, plus any additional desired ingredient present in the previously sterile-filtered solutions.

Pharmaceutical compositions can be in unit-dose or multi-dose form or in a form that allows for slow or controlled release of the HDAC inhibitor. Each unit-dose can be in the form of a tablet, capsule or packaged composition such as, for example, a packeted powder, vial, ampoule, prefilled syringe or sachet containing liquids. The unit-dose form also can be the appropriate number of any such compositions in package form. Pharmaceutical compositions in multi-dose form can be packaged in containers such as sealed ampoules and vials. In this case, the HDAC inhibitor can be stored in a freeze-dried (lyophilized) condition requiring only the addition of a sterile liquid carrier immediately prior to use. In addition, extemporaneous injection solutions and suspensions can be prepared from sterile powders, granules and tablets of the kind previously described.

EXAMPLES

Method A

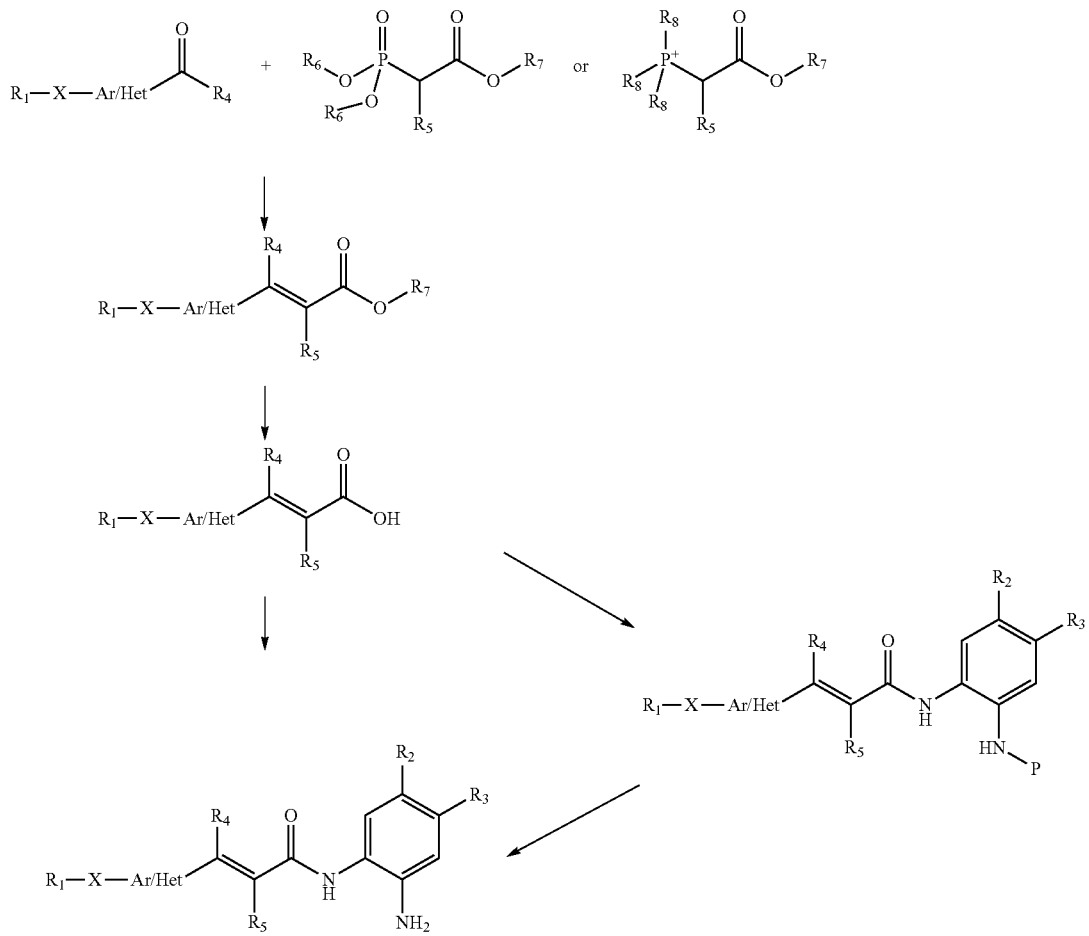

Compounds described herein, where n=1, and where R1, X, Ar/Het, R2, R3, R4, R5 are defined as described anywhere herein, can be obtained by reaction of a mono- or bicyclic heterocycle aldehyde or ketone, synthesized using methods well known by those skilled in the art (see for example Joule J A and Mills K, Heterocyclic Chemistry, Fifth Edition, John Wiley & Sons, Inc., Hoboken, N.J., USA) with a Wittig or Homer-Wadsworth-Emmons reagent to form a γ-substituted acrylate ester. After saponification, a substituted or unsubstituted N-(o-aminophenyl)amide is prepared by an amide-forming reaction of the acrylic acid with a protected or unprotected substituted or unsubstituted o-phenylenediamine, where P is a protecting group as defined in Wuts P G M and Greene T W, 2006, Greene's Protective Groups in Organic Synthesis, Fourth Edition, John Wiley & Sons, Inc., Hoboken, N.J., USA. Compounds of the invention can be obtained after deprotection if required using methods well known to those skilled in the art and which are described for example in Wuts P G M and Greene T W, 2006, Greene's Protective Groups in Organic Synthesis, Fourth Edition, John Wiley & Sons, Inc., Hoboken, N.J., USA.

Example 1: Hydrochloride Salt of (E)-N-(2-aminophenyl)-3-(imidazo[1,2-a]pyridin-3-yl)acrylamide A6

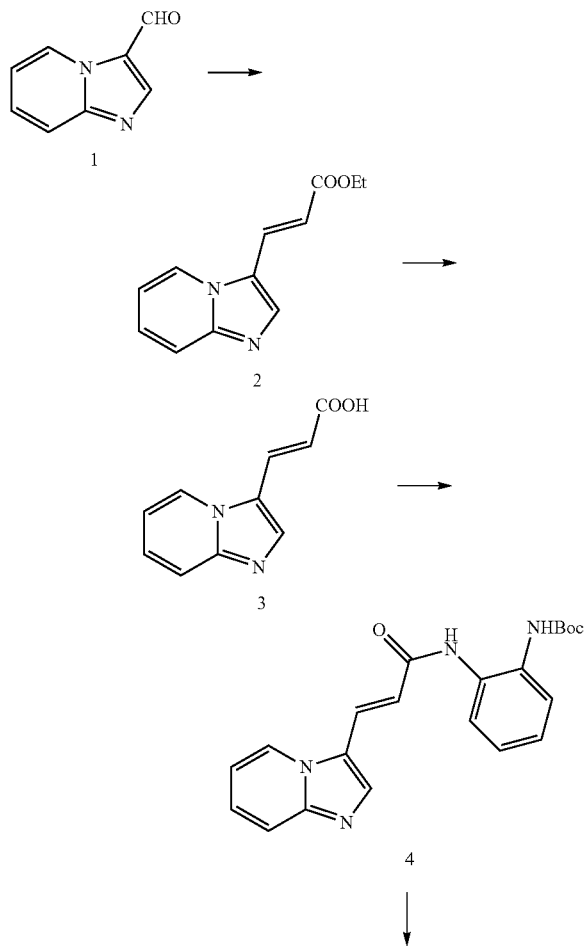

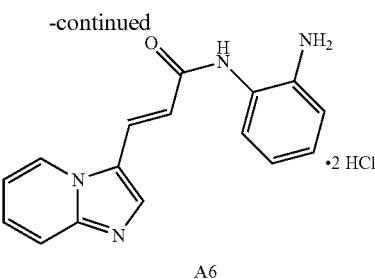

A6

(E)-ethyl 3-(imidazo[1,2-a]pyridin-3-yl)acrylate (Ethoxycarbonylmethylene)triphenylphosphorane (0.72 g, 2.05 mmol) was added to a solution of imidazo[1,2-a]pyridine-3-carbaldehyde (0.25 g, 1.71 mmol) in anhydrous tetrahydrofuran (THF) (20 mL) at room temperature. The reaction mixture was heated overnight at 65° C. After completion of the reaction as indicated by HPLC, the reaction mixture was diluted with ethyl acetate (EtOAc) (20 mL) and quenched with a saturated solution of ammonium chloride (10 mL). The organic layer was washed with water (3×20 mL) and brine (15 mL). It was dried over anhydrous $Na_2SO_4$, filtered and evaporated to get the crude product. This crude was purified by silica gel column chromatography using 50-80% EtOAc in Hexanes to provide pure (E)-ethyl 3-(imidazo[1,2-a]pyridin-3-yl)acrylate (0.19 g) as a white solid. $ES^+$ $(M+H)^+$ 217.

(E)-3-(imidazo[1,2-a]pyridin-3-yl)acrylic acid

A 1M aqueous solution of KOH (2.2 mL) was added to a solution of (E)-ethyl 3-(imidazo[1,2-a]pyridin-3-yl)acrylate (0.19 g, 0.88 mmol) in EtOH:THF (1:1 v/v) (10 mL). The resulting solution was heated at 50° C. for 3 h. After completion of the reaction the reaction mixture was evaporated and water (10 mL) was added to the residue. This solution was carefully acidified to pH 4 with a 3 M HCl aqueous solution. Since the product, (E)-3-(imidazo[1,2-a]pyridin-3-yl)acrylic acid, was soluble in water, the solution was concentrated under reduced pressure and the solid residue was used directly for the next step. $ES^+$ $(M+H)^+$ 189.

(E)-tert-butyl (2-(3-(imidazo[1,2-a]pyridin-3-yl)acrylamido)phenyl)carbamate

Diisopropylethylamine (DIPEA, 0.34 g, 2.63 mmol) was added to a solution of (E)-3-(imidazo[1,2-a]pyridin-3-yl)acrylic acid (0.17 g, 0.88 mmol) in 20 mL of dichloromethane (DCM). After addition of tert-butyl-2-aminophenylcarbamate (0.22 g, 1.65 mmol) and 2-(1H-7-azabenzotriazol-1-yl)-1,1,3,3-tetramethyluronium hexafluorophosphate (HATU, 0.43 g, 1.14 mmol) the reaction mixture was stirred overnight at room temperature under a nitrogen atmosphere. After completion of the reaction as indicated by HPLC, the reaction mixture was washed with saturated sodium bicarbonate ($NaHCO_3$) and brine. It was dried over $Na_2SO_4$, filtered and evaporated to give crude (E)-tert-butyl (2-(3-(imidazo[1,2-a]pyridin-3-yl)acrylamido)phenyl)carbamate. The solid was washed with ethyl acetate (50 mL) and saturated $NaHCO_3$ gave pure product as a light colored solid (0.11 g). $ES^+$ $(M+H)^+$ 379.

(E)-N-(2-aminophenyl)-3-(imidazo[1,2a]pyridin-3-yl)acrylamide

A 4 M solution of HCl in dioxane (2.5 mL) was added to a solution of (E)-tert-butyl (2-(3-(imidazo[1,2-a]pyridin-3-yl)acrylamido)phenyl)carbamate (0.11 g, 0.29 mmol) in dioxane (2.5 mL). The mixture was stirred at room temperature for 3 h. Precipitate formation was observed. After completion of the reaction as indicated by HPLC/MS, the reaction mixture was diluted with diethyl ether (20 mL) and the salt was filtered, washed with ether and dried overnight to get the HC1 salt of (E)-N-(2-aminophenyl)-3-(imidazo[1,2-a]pyridin-3-yl)acrylamide (80 mg) as an off-white solid. $^1$H NMR (CD3OD) δ: 9.04-9.13 (m, 1H), 8.67 (s, 1H), 8.17 (d, J=15.8 Hz, 1H), 8.00-8.13 (m, 2H), 7.66 (td, J=6.9, 1.4 Hz, 1H), 7.42-7.58 (m, 4H), 7.21 (d, J=15.8 Hz, 1H); ES$^+$ (M+H)$^+$ 279.2

| Compound | Structure | aldehyde |
|---|---|---|
| A1 | 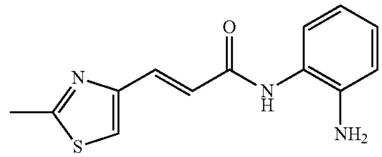 [SMILES: Cc1nc(/C=C/C(=O)Nc2ccccc2N)cs1] | |
| A2 | 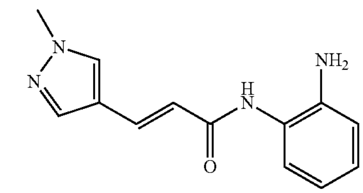 [SMILES: Cn1cc(/C=C/C(=O)Nc2ccccc2N)cn1] | |
| A3 | 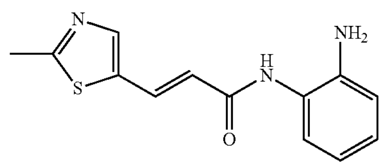 [SMILES: Cc1ncc(/C=C/C(=O)Nc2ccccc2N)s1] | |
| A4 | 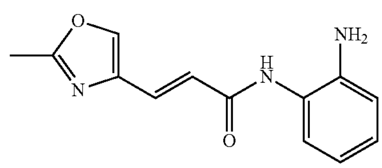 [SMILES: Cc1nc(/C=C/C(=O)Nc2ccccc2N)co1] | |
| A5 | 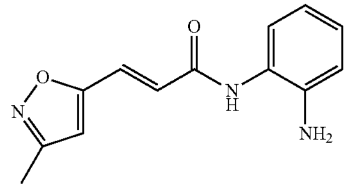 [SMILES: Cc1cc(/C=C/C(=O)Nc2ccccc2N)on1] | |
| A6 (salt) | 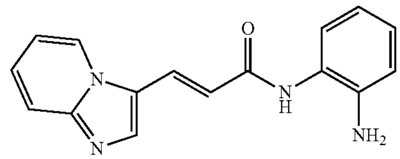 [SMILES: Nc1ccccc1NC(=O)/C=C/c1cnc2ccccn12] | |
| A7 | 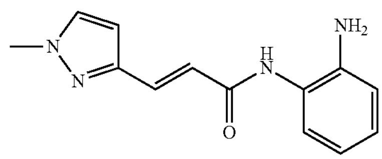 [SMILES: Cn1ccc(/C=C/C(=O)Nc2ccccc2N)n1] | |
| A8 | 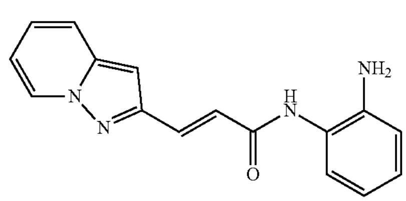 [SMILES: Nc1ccccc1NC(=O)/C=C/c1cc2ccccn2n1] | |

-continued

| | | | |
|---|---|---|---|
| A9 (salt) | 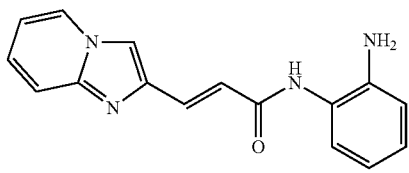 [SMILES: Nc1ccccc1NC(=O)/C=C/c1cn2ccccc2n1] | | 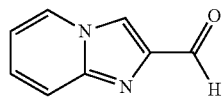 [SMILES: O=Cc1cn2ccccc2n1] |
| A10 | 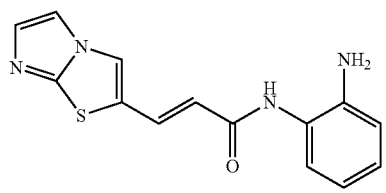 [SMILES: Nc1ccccc1NC(=O)/C=C/c1cn2ccnc2s1] | | 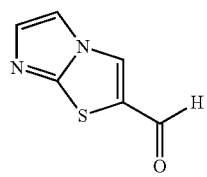 |
| A11 | 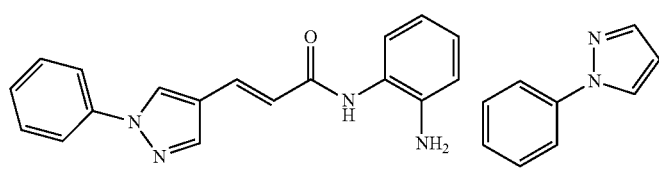 | | 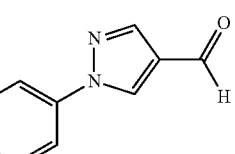 |
| A12 | 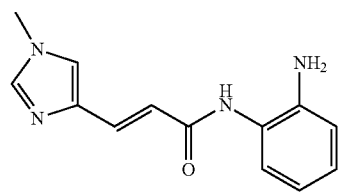 [SMILES: Cn1cnc(/C=C/C(=O)Nc2ccccc2N)c1] | | 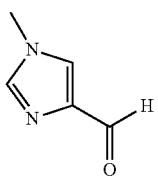 |

| Compound | diamine | MS | NMR |
|---|---|---|---|
| A1 | H₂N—C₆H₄—NH₂ (ortho) | ES⁺ (M + H)⁺ 260 | ¹H NMR (CD₃OD) δ: 7.57 (d, J = 15.1 Hz, 1H), 7.52-7.62 (m, 1H), 7.20 (dd, J = 8.0, 1.4 Hz, 1H), 6.99 (d, J = 15.1 Hz, 1H), 7.04 (ddd, J = 8.0, 7.6, 1.4 Hz, 1H), 6.87 (dd, J = 8.0, 1.4 Hz, 1H), 6.74 (td, J = 7.6, 1.4 Hz, 1H), 2.67-2.79 (m, 3H) |
| A2 | H₂N—C₆H₄—NH₂ (ortho) | ES⁺ (M + H)⁺ 243 | ¹H NMR (CD₃OD) δ: 7.88 (s, 1H), 7.77 (s, 1H), 7.54 (d, J = 15.7 Hz, 1H), 7.17 (dd, J = 7.6, 1.4 Hz, 1H), 7.04 (td, J = 7.8, 1.4 Hz, 1H), 6.87 (dd, J = 8.0, 1.5 Hz, 1H), 6.74 (td, J = 7.6, 1.4 Hz, 1H), 6.57 (d, J = 15.7 Hz, 1H), 3.90 (s, 3H) |
| A3 | H₂N—C₆H₄—NH₂ (ortho) | ES⁺ (M + H)⁺ 260 | ¹H NMR (CD₃OD) δ: 7.50 (d, J = 15.7 Hz, 1H), 7.21 (dd, J = 7.7, 1.4 Hz, 1H), 7.05 (td, J = 8.1, 1.5 Hz, 1H), 6.98 (d, J = 15.7 Hz, 2H), 6.87 (dd, J = 8.0, 1.4 Hz, 1H), 6.73 (td, J = 8.0, 1.4 Hz, 1H), 6.55 (s, 1H), 2.31 (s, 1H) |
| A4 | H₂N—C₆H₄—NH₂ (ortho) | ES⁺ (M + H)⁺ 244 | ¹H NMR (CD₃OD) δ: 8.01 (s, 1H), 7.48 (d, J = 15.4 Hz, 1H), 7.18 (dd, J = 7.7, 1.4 Hz, 1H), 7.04 (ddd, J = 8.0, 7.3, 1.4 Hz, 1H), 6.84 (d, J = 15.4 Hz, 1H), 6.86 (dd, J = 8.0, 1.4 Hz, 1H), 6.73 (td, J = 7.6, 1.4 Hz, 1H), 2.49 (s, 3H) |
| A5 | H₂N—C₆H₄—NH₂ (ortho) | ES⁺ (M + H)⁺ 244 | ¹H NMR (CD₃OD) δ: 7.49 (d, J = 15.7 Hz, 1H), 7.21 (dd, J = 8.0, 1.5 Hz, 1H), 7.04 (ddd, J = 8.0, 7.7, 1.5 Hz, 1H), 6.98 (d, J = 15.7 Hz, 1H), 6.86 (dd, J = 8.0, 1.5 Hz, 1H), 6.73 (td, J = 7.7, 1.4 Hz, 1H), 6.55 (s, 1H), 2.31 (s, 3H) |

-continued

| | | | |
|---|---|---|---|
| A6 (salt) | [structure: HN-Boc, H2N-phenyl] | ES+ (M + H)+ 279 | 1H NMR (CD3OD) δ: 9.09 (dt, J = 7.1, 0.8 Hz, 1H), 8.67 (s, 1H), 8.17 (d, J = 15.7 Hz, 1H), 8.10 (ddd, J = 9.1, 6.9, 1.1 Hz, 1H), 8.03 (dt, J = 9.1, 1.2 Hz, 1H), 7.66 (td, J = 6.9, 1.4 Hz, 1H), 7.43-7.60 (m, 4H), 7.21 (d, J = 15.7 Hz, 1H) |
| A7 | [structure: NH2, H2N-phenyl] | ES+ (M + H)+ 243 | 1H NMR (CD3OD) δ: 7.59 (d, J = 2.5 Hz, 1H), 7.57 (d, J = 15.8 Hz, 1H), 7.19 (dd, J = 7.7, 1.4 Hz, 1H), 7.04 (td, J = 7.6, 1.4 Hz, 1H), 6.86 (dd, J = 8.1, 1.2 Hz, 1H), 6.78 (d, J = 15.8 Hz, 1H), 6.74 (td, J = 7.7, 1.4 Hz, 1H), 6.59 (d, J = 2.5 Hz, 1H), 3.90 (s, 3H) |
| A8 | [structure: HN-Boc, H2N-phenyl] | | 1H NMR (CD3OD) δ: 8.50 (d, J = 6.6 Hz, 1H), 7.73 (d, J = 15.9 Hz, 1H), 7.64 (d, J = 8.8 Hz, 1H), 7.17-7.29 (m, 2H), 7.06 (d, J = 15.7 Hz, 2H), 7.05 (ddd, J = 8.0, 7.5, 1.5 Hz, 1H), 6.83-6.97 (m, 3H), 6.75 (td, J = 7.7, 1.4 Hz, 1H) |
| A9 (salt) | [structure: HN-Boc, H2N-phenyl] | ES+ (M + H)+ 279 | 1H NMR (CD3OD) δ: 8.82 (dt, J = 7.0, 1.1 Hz, 1H), 8.58 (s, 1H), 8.06 (ddd, J = 9.1, 7.0, 1.1 Hz, 1H), 7.96 (dt, J = 9.1, 0.8 Hz, 1H), 7.84 (d, J = 15.9 Hz, 1H), 7.45-7.57 (m, 5H), 7.22 (d, J = 15.9 Hz, 1H) |
| A10 | [structure: NH2, H2N-phenyl] | ES+ (M + H)+ 285 | 1H NMR (CD3OD) δ: 8.11 (s, 1H), 7.78 (d, J = 15.4 Hz, 1H), 7.70 (d, J = 1.4 Hz, 1H), 7.30 (d, J = 1.4 Hz, 1H), 7.20 (dd, J = 7.8, 1.5 Hz, 1H), 7.04 (ddd, J = 8.2, 7.7, 1.4 Hz, 1H), 6.87 (dd, J = 8.2, 1.4 Hz, 1H), 6.74 (ddd, J = 7.8, 7.7, 1.4 Hz, 1H), 6.56 (d, J = 15.4 Hz, 1H) |
| A11 | [structure: HN-Boc, H2N-phenyl] | ES+ (M + H)+ 305 | 1H NMR (CD3OD) δ: 8.53 (s, 1H), 8.03 (s, 1H), 7.78 (d, J = 8.5 Hz, 2H), 7.64 (d, J = 15.7 Hz, 1H), 7.51 (t, J = 7.8 Hz, 2H), 7.35 (t, J = 7.7 Hz, 1H), 7.19 (d, J = 7.7 Hz, 1H), 7.04 (t, J = 7.6 Hz, 1H), 6.88 (d, J = 8.0 Hz, 1H), 6.69 (d, J = 15.7 Hz, 1H), 6.74 (t, J = 7.7 Hz, 1H) |
| A12 | [structure: HN-Boc, H2N-phenyl] | ES+ (M + H)+ 243 | 1H NMR (CD3OD) δ: 7.69 (s, 1H), 7.51 (d, J = 15.4 Hz, 1H), 7.37 (s, 1H), 7.19 (dd, J = 7.8, 1.2 Hz, 1H), 7.03 (dt, J = 8.1, 1.4 Hz, 1H), 6.86 (dd, J = 8, 1.4 Hz, 1H), 6.74 (d, J = 15.4 Hz, 1H), 6.74 (dt, J = 8, 1.2 Hz, 1H), 3.73 (s, 3H) |

Method B

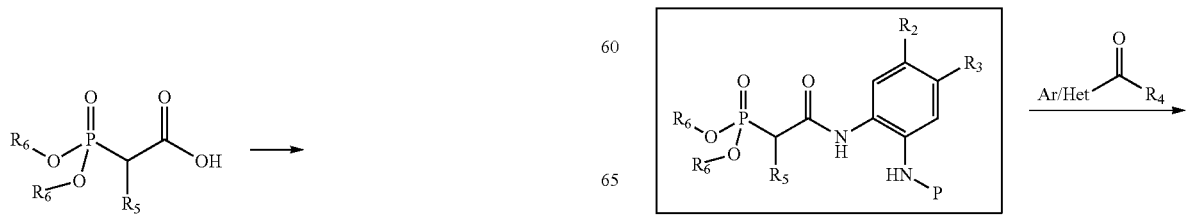

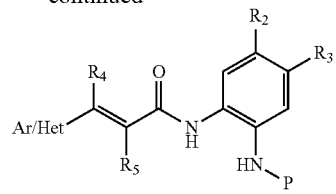

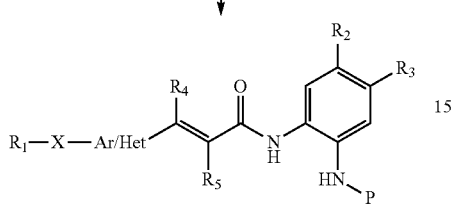

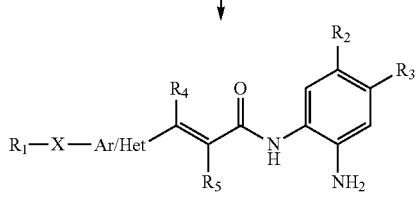

Compounds described herein, where n=1, and R1, X, R2, R3, R4, R5, Ar/Het are defined as defined anywhere herein, can be via preparation of the advanced intermediate Ar/Het-CR4=CR5-CO—NH—C$_6$H$_2$R2R3(NH—P) where P is a protecting group, as defined in, for example, Wuts P G M and Greene T W, 2006, Greene's Protective Groups in Organic Synthesis, Fourth Edition, John Wiley & Sons, Inc., Hoboken, N.J., USA, and NH—P is ortho to the CO—NH group, i.e. in positions 1 and 2 of the aromatic ring.

Thus a Wittig or Horner-Wadsworth-Emmons carboxylic acid reagent, prepared by methods well known to those skilled in the art such as the Arbuzov reaction, can be reacted with a suitably mono-protected substituted or unsubstituted o-phenylenediamine. This compound is then reacted with a monocyclic or bicyclic heterocyclic aldehyde or ketone to form the corresponding γ-substituted acrylamide. This advanced intermediate can be derivatized to generate compounds of the invention by reaction with different R1-X-containing reagents using coupling techniques well known to those skilled in the art such as, but not limited to, Suzuki coupling, Heck coupling, alkylation, acylation. The same intermediate can also be simply deprotected to form the compound where R1 is H and X is a single bond.

Example 2: Advanced Intermediate (E)-tert-butyl (2-(3-(1H-pyrazol-4-yl)acrylamido)phenyl)carbamate

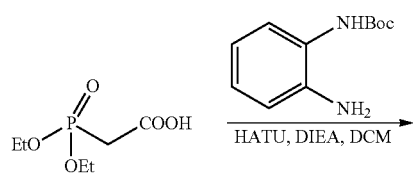

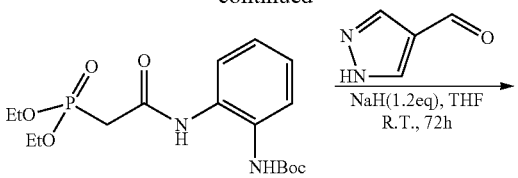

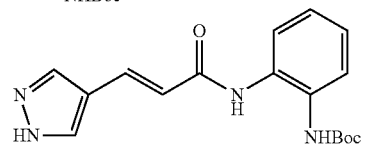

tert-butyl (2-(2-(diethoxyphosphoryl)acetamido)phenyl)carbamate

DIPEA (5.16 g, 6.90 mL, 40 mmol) and tert-butyl 2-aminophenylcarbamate (2.08 g, 10 mmol) were added to a solution of 2-(diethoxyphosphoryl)acetic acid (2.15 g, 11 mmol) in DCM (120 mL). After the mixture was stirred for ten minutes, HATU (4.56 g, 12 mmol) was added to the reaction and stirring was prolonged for 6 h at room temperature under a nitrogen atmosphere. After completion of the reaction as indicated by HPLC, the reaction mixture was washed with saturated NaHCO$_3$ and brine. It was dried over Na$_2$SO$_4$ and filtered. The filtrate was evaporated in vacuo to get the crude product, which was triturated with 30% v/v hexanes in EtOAc for 30 min. The solid was filtered, washed with 30% hexanes in EtOAc and dried to get 2.92 g of tert-butyl (2-(2-(diethoxyphosphoryl)acetamido)phenyl)carbamate as an off-white solid in 76% yield. $^1$HNMR (300 MHz, CD$_3$OD): δ 7.64 (d, 1H, J=8.4 Hz), 7.37 (dd, 1H, J=1.8 Hz, 8.1 Hz), 7.07-7.24 (m, 2H), 4.20 (m, 4H), 3.15 (d, 2H, J=21.9 Hz), 1.51 (s, 9H), 1.35 (t, 6H, J=6.9 Hz), MS: ES$^+$ (M+Na)$^+$: 410

(E)-tert-butyl (2-(3-(1H-pyrazol-4-yl)acrylamido)phenyl)carbamate

A 60% suspension of NaH in paraffin oil (192 mg, 5 mmol) was added portionwise to a solution of tert-butyl (2-(2-(diethoxyphosphoryl)acetamido)phenyl)carbamate (1.93 g, 5 mmol) in anhydrous THF (25 mL) at 0° C. The reaction mixture was stirred for 30 min before being warmed up to room temperature. 1H-pyrazole-4-carbaldehyde (400 mg, 4.16 mmol) dissolved in anhydrous THF (5 mL) was then added and the reaction mixture was stirred for 72 h under a nitrogen atmosphere. After completion of the reaction as indicated by HPLC, the mixture was diluted with EtOAc (80 mL) and quenched with a saturated NH$_4$Cl solution (10 mL). The organic layer was separated and washed with water (40 mL) and brine (20 mL). It was dried over anhydrous Na$_2$SO$_4$ and the solid was filtered. The filtrate was evaporated under vacuum. The isolated crude was purified by silica gel column chromatography using a gradient of 0-100% EtOAc in hexanes to provide 986 mg of (E)-tert-butyl (2-(3-(1H-pyrazol-4-yl)acrylamido)phenyl) carbamate as a white solid. $^1$HNMR (300 MHz, CD$_3$OD): δ 7.93 (broad s, 2H), 7.64 (d, 1H, J=15.6 Hz), 7.56 (d, 1H, J=7.2 Hz), 7.45 d, 1H, J=7.8 Hz), 7.11-7.24 (m, 2H), 6.59 (d, 1H, J=15.6 Hz), 1.50 (s, 9H), MS: ES$^+$ (M+Na)$^+$: 351

Example 3: Hydrochloride Salt of (E)-N-(2-aminophenyl)-3-(1-(2-(3-chloro-5-fluorophenoxy)ethyl)-1H-pyrazol-4-yl)acrylamide B5

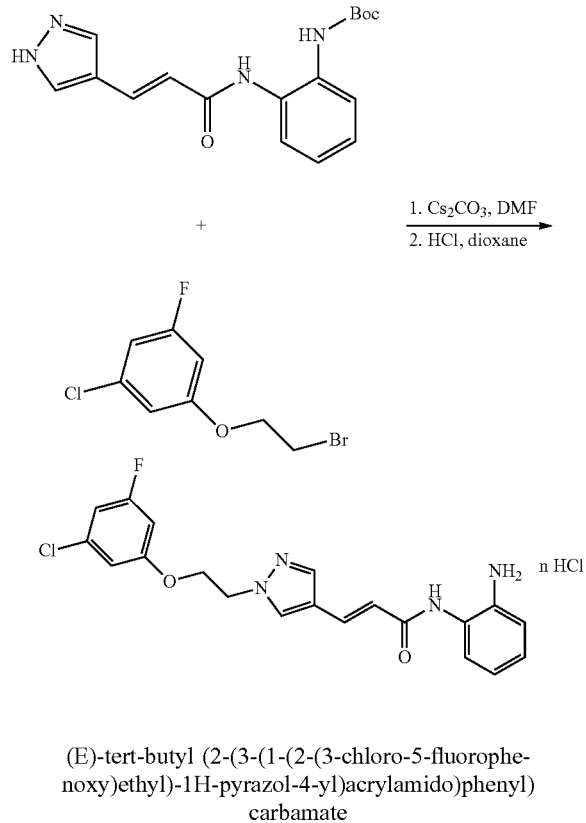

(E)-tert-butyl (2-(3-(1-(2-(3-chloro-5-fluorophenoxy)ethyl)-1H-pyrazol-4-yl)acrylamido)phenyl)carbamate Cesium carbonate (98 mg, 0.30 mmol) was added to a solution of (E)-tert-butyl (2-(3-(1H-pyrazol-4-yl)acrylamido)phenyl)carbamate (100 mg, 0.30 mmol) in anhydrous DMF (4 mL). A solution of 1-(2-bromoethoxy)-3-chloro-5-fluorobenzene (76 mg, 0.30 mmol) in DMF (1 mL) was then added and the reaction mixture was stirred overnight at room temperature under a nitrogen atmosphere. It was diluted with EtOAc (30 mL) and washed with water (2×40 mL) and brine (10 mL). The organic layer was dried over anhydrous Na$_2$SO$_4$ and filtered. The evaporated crude was purified by silica gel column chromatography using a gradient of 0-100% of EtOAc in hexanes to provide 144 mg of (E)-tert-butyl (2-(3-(1-(2-(3-chloro-5-fluorophenoxy)ethyl)-1H-pyrazol-4-yl)acrylamido)phenyl)carbamate as a white solid. MS: ES$^+$ (M+Na)$^+$: 523

(E)-N-(2-aminophenyl)-3-(1-(2-(3-chloro-5-fluorophenoxy)ethyl)-1H-pyrazol-4-yl)acrylamide A 4 M solution of HCl in dioxane (2 mL) was added to a solution of (E)-tert-butyl (2-(3-(1-(2-(3-chloro-5-fluorophenoxy)ethyl)-1H-pyrazol-4-yl)acrylamido)phenyl)carbamate (118 mg, 0.23 mmol) in dioxane (3 mL) and the mixture was stirred for 6 h at room temperature under a nitrogen atmosphere. The reaction mixture was then diluted with EtOAc (15 mL). The salt was filtered, washed with EtOAc and dried overnight to give 99 mg of the hydrochloric acid salt of (E)-N-(2-aminophenyl)-3-(1-(2-(3-chloro-5-fluorophenoxy)ethyl)-1H-pyrazol-4-yl)acrylamide as an off-white solid. MS: ES$^+$ (M+Na)$^+$: 423

Example 4: Hydrochloride Salt of (E)-N-(2-aminophenyl)-3-(1-(2-(3,5-difluorophenoxy)ethyl)-1H-pyrazol-4-yl)acrylamide B3

(E)-tert-butyl (2-(3-(1-(2-(3, 5-difluorophenoxy)ethyl)-1H-pyrazol-4-yl)acrylamido)phenyl)carbamate As described for the synthesis of B5 above, cesium carbonate (64 mg, 0.27 mmol) followed by a solution of 1-(2-bromoethoxy)-3,5-difluorobenzene (76 mg, 0.30 mmol) in DMF (1 mL) were added to a solution of (E)-tert-butyl (2-(3-(1H-pyrazol-4-yl)acrylamido)phenyl)carbamate (90 mg, 0.27 mmol) in anhydrous DMF (4 mL). The reaction mixture was stirred overnight at room temperature under a nitrogen atmosphere. It was then diluted with 30 mL EtOAc and washed with water (2×40 mL) and brine (10 mL). The organic layer was dried over anhydrous Na$_2$SO$_4$ and filtered. The concentrated filtrate was purified by silica gel column chromatography using a gradient of 0-100% of EtOAc in hexanes to provide, after evaporation under reduced pressure of pooled fractions, 123 mg of (E)-tert-butyl (2-(3-(1-(2-(3,5-difluorophenoxy)ethyl)-1H-pyrazol-4-yl)acrylamido)phenyl)carbamate as a white solid. MS: ES$^+$ (M+Na)$^+$: 507

(E)-N-(2-aminophenyl)-3-(1-(2-(3,5-difluorophenoxy)ethyl)-1H-pyrazol-4-yl)acrylamide A solution of (E)-tert-butyl (2-(3-(1-(2-(3,5-difluorophenoxy)ethyl)-1H-pyrazol-4-yl)acrylamido)phenyl)carbamate (113 mg, 0.23 mmol) in dioxane (3 mL) was mixed with a 4 M solution of HCl in dioxane (2 mL). The mixture was stirred for 6 h at room temperature under a nitrogen atmosphere. The reaction mixture was then diluted with ethylaceate (15 mL). The salt was filtered, washed with EtOAc and dried overnight to 92 mg of the hydrochloric acid salt of (E)-N-(2-aminophenyl)-3-(1-(2-(3,5-difluorophenoxy)ethyl)-1H-pyrazol-4-yl)acrylamide as an off-white solid. MS: $^1$H NMR (CD$_3$OD) δ: 8.07 (s, 1H), 7.86 (s, 1H), 7.70 (d, J=15.4 Hz, 1H), 7.28-7.54 (m, 4H), 6.62 (d, J=15.7 Hz, 1H), 6.45-6.57 (m, 3H), 4.55 (t, J=5.2 Hz, 2H), 4.37 (t, J=5.2 Hz, 2H) ES$^+$ (M+Na)$^+$: 407

Table: Method B

| Compound | Structure | R1—X— coupling reagent |
|---|---|---|
| B1 (salt) | 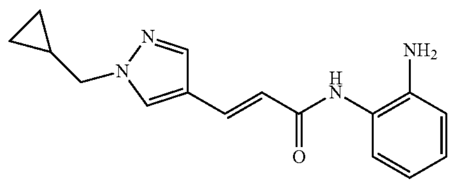 [SMILES: Nc1ccccc1NC(=O)/C=C/c1cnn(CC2CC2)c1] | cyclopropylmethyl chloride |
| B2 (salt) | 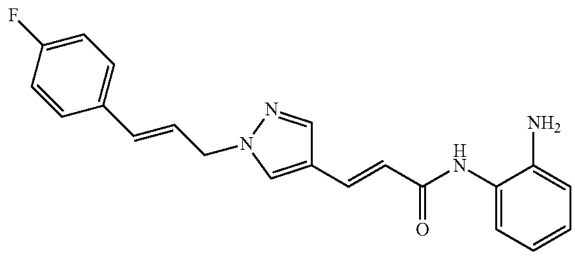 [SMILES: Nc1ccccc1NC(=O)/C=C/c1cnn(C/C=C/c2ccc(F)cc2)c1] | (E)-1-(3-bromoprop-1-en-1-yl)-4-fluorobenzene |
| B3 (salt) | 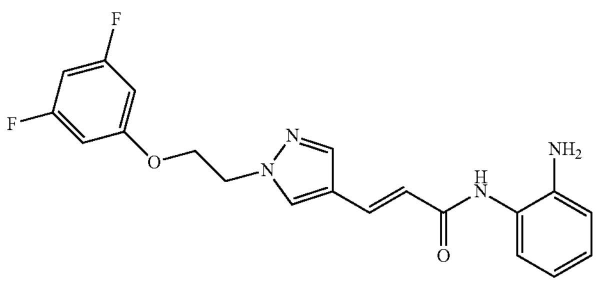 [SMILES: Nc1ccccc1NC(=O)/C=C/c1cnn(CCOc2cc(F)cc(F)c2)c1] | 1-(2-bromoethoxy)-3,5-difluorobenzene |
| B4 (salt) | 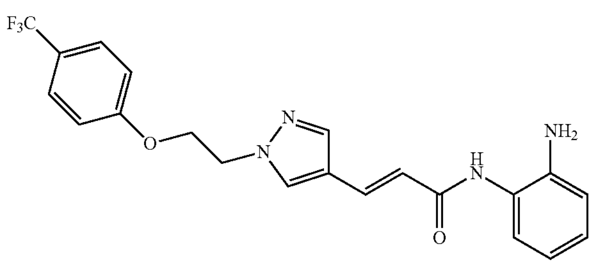 [SMILES: Nc1ccccc1NC(=O)/C=C/c1cnn(CCOc2ccc(C(F)(F)F)cc2)c1] | 1-(2-bromoethoxy)-4-(trifluoromethyl)benzene |
| B5 (salt) | 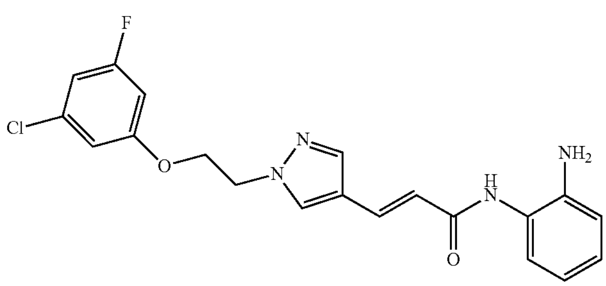 [SMILES: Nc1ccccc1NC(=O)/C=C/c1cnn(CCOc2cc(F)cc(Cl)c2)c1] | 1-(2-bromoethoxy)-3-chloro-5-fluorobenzene |
| B6 | 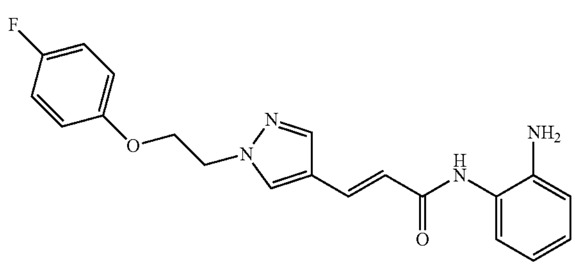 [SMILES: Nc1ccccc1NC(=O)/C=C/c1cnn(CCOc2ccc(F)cc2)c1] | 1-(2-bromoethoxy)-4-fluorobenzene |

-continued

| Compound | MS | NMR |
|---|---|---|
| B1 (salt) | ES⁺ (M + H)⁺ 283 | ¹H NMR (CD₃OD) δ: 8.13 (s, 1H), 7.91 (s, 1H), 7.72 (d, J = 15.7 Hz, 1H), 7.30-7.62 (m, 4H), 6.65 (d, J = 15.7 Hz, 1H), 4.05 (d, J = 7.1 Hz, 2H), 1.17-1.46 (m, 1H), 0.56-0.82 (m, 2H), 0.36-0.49 (m, 2H) |
| B2 (salt) | ES⁺ (M + H)⁺ 363 | ¹H NMR (CD₃OD) δ: 8.08 (s, 1H), 7.90 (s, 1H), 7.73 (d, J = 15.7 Hz, 1H), 7.34-7.58 (m, 6H), 7.05 (t, J = 9.1 Hz, 2H), 6.63 (d, J = 15.7 Hz, 1H), 6.63 (dd, J = 15.7, 0.8 Hz, 1H), 6.38 (dt, J = 15.7, 6.3 Hz, 1H), 4.95 (dd, J = 6.3, 0.8 Hz. 2H) |
| B3 (salt) | ES⁺ (M + Na)⁺: 407 | ¹H NMR (CD₃OD) δ: 8.07 (s, 1H), 7.86 (s, 1H), 7.70 (d, J = 15.4 Hz, 1H), 7.28-7.54 (m, 4H), 6.62 (d, J = 15.7 Hz, 1H), 6.45-6.57 (m, 3H), 4.55 (t, J = 5.2 Hz, 2H), 4.37 (t, J = 5.2 Hz, 2H) |
| B4 (salt) | ES⁺ (M + Na)⁺: 429 | ¹H NMR (CD₃OD) δ: 8.09 (s, 1H), 7.87 (s, 1H), 7.72 (d, J = 15.7 Hz, 1H), 7.57 (d, J = 8.8 Hz, 2H), 7.40-7.54 (m, 3H), 7.37 (dd, J = 8.0, 1.5 Hz, 1H), 7.06 (d, J = 8.8 Hz, 2H), 6.61 (d, J = 15.7 Hz, 1H), 4.59 (t, J = 5.2 Hz, 2H), 4.45 (t, J = 5.2 Hz, 2H) |
| B5 (salt) | ES⁺ (M + Na)⁺: 423 | ¹H NMR (CD₃OD) δ: 8.07 (s, 1H), 7.87 (s, 1H), 7.71 (d, J = 15.7 Hz, 1H), 7.32-.57 (m, 4H), 6.77 (dt, J = 8.2, 2.2 Hz, 1H), 6.78 (d, J = 2.2 Hz, 1H), 6.61 (d, J = 15.9 Hz, 1H), 6.66 (dt, J = 10.7, 2.2 Hz, 1H), 4.55 (t, J = 5.2 Hz, 2H), 4.38 (t, J = 5.2 Hz, 2H) |
| B6 | ES⁺ (M + Na)⁺: 367 | ¹H NMR (CD₃OD) δ: 8.00 (s, 1H), 7.82 (s, 1H), 7.55 (d, J = 15.7 Hz, 1H), 7.17 (dd, J = 8.0, 1.4 Hz, 1H), 6.92-7.07 (m, 3H), 6.82-6.92 (m, 3H), 6.73 (td, J = 7.6, 1.4 Hz, 1H), 6.58 (d, J = 15.7 Hz, 1H), 4.51 (t, J = 5.2 Hz, 1H), 4.31 (t, J = 5.2 Hz, 1H) |

Method C

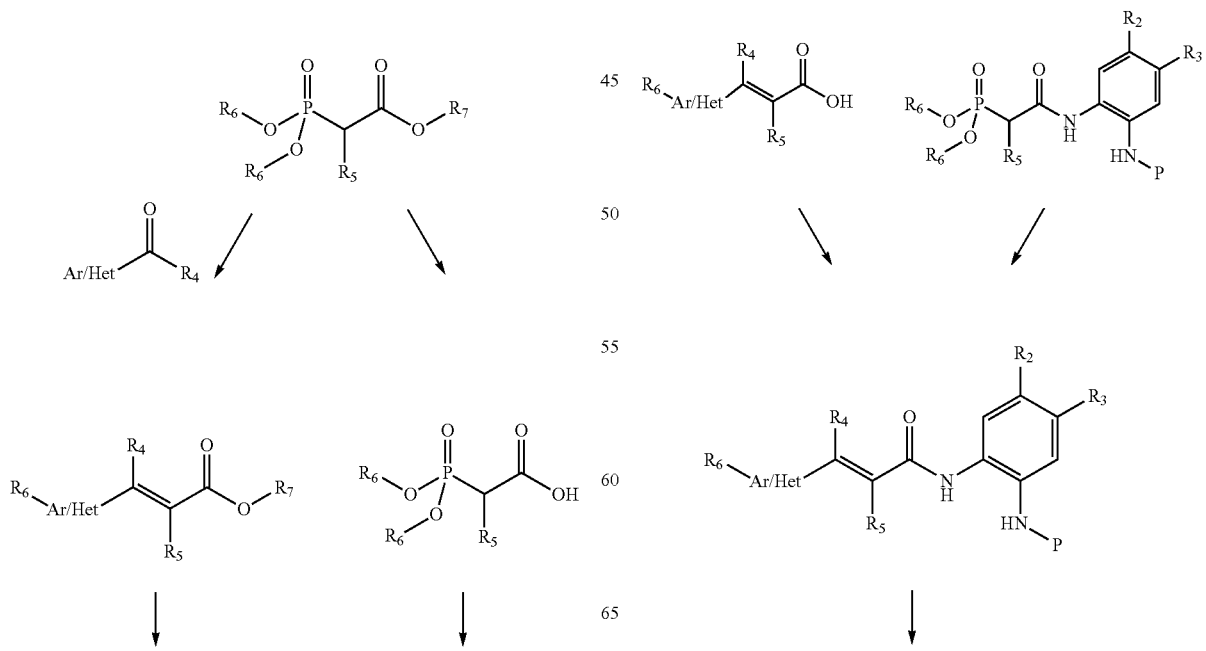

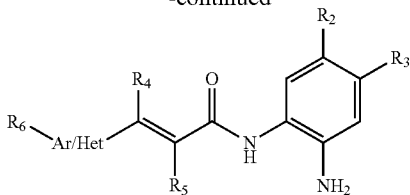

Compounds described herein, where n=1 and R2, R3, R4, R5 are defined as anywhere herein, where Ar/Het is a mono or bicyclic heterocycle with a free amino group, and R6 stands for R1-X, can be prepared using a Homer Wadsworth Emmons approach where the corresponding heterocyclic aldehyde or ketone, such as, but not limited to, 1H-pyrazole-3-carbaldehyde, 1H-pyrazole-4-carbaldehyde, 1-(1H-pyrazol-4-yl)ethanone, 1H-imidazole-4-carbaldehyde, is reacted with a dialkoxyphosphono acetic acid ester to give the corresponding γ-(N-alkylheterocycle)acrylate ester. The ester can be hydrolyzed and the acid reacted with a protected or unprotected substituted or unsubstituted o-phenylenediamine to give compounds of the invention after deprotection if required using methods well known to those skilled in the art and which are described for example in P. G. M. Wuts and T. W. Greene, 2006, Greene's Protective Groups in Organic Synthesis, Fourth Edition, John Wiley & Sons, Inc., Hoboken, N.J., USA.

Example 5: (E)-N-(2-amino-5-fluorophenyl)-3-(1-methyl-1H-pyrazol-4-yl)acrylamide C2

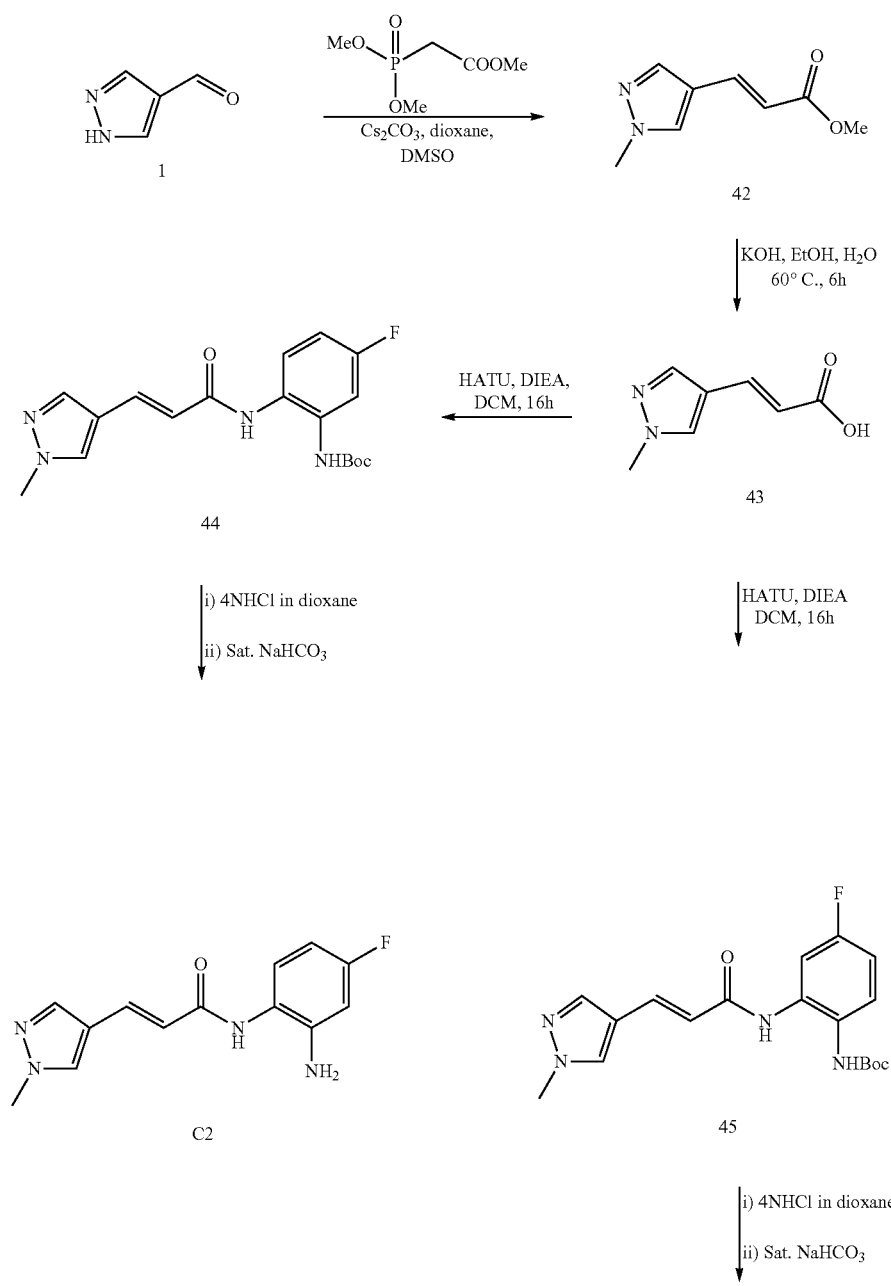

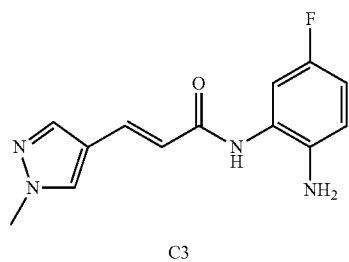

C3

(E)-methyl 3-(1-methyl-1H-pyrazol-4-yl)acrylate

Cs$_2$CO$_3$ (1.304 g, 4 mmol) was added to a solution of 1H-pyrazole-4-carbaldehyde (0.192 g, 2 mmol) in dioxane (8 mL) at room temperature. Trimethylphosphonoacetate (0.364 g, 0.40 mmol) was added to this suspension, followed by DMSO (2 mL). The reaction mixture was heated to 100° C. overnight. It was then diluted with EtOAc (40 mL), and washed with water (40 mL) and brine (20 mL). The organic layer was concentrated under vacuum. The crude was purified by silica gel column chromatography using a 0-100% gradient of EtOAc in hexanes to provide (E)-methyl 3-(1-methyl-1H-pyrazol-4-yl)acrylate (0.278 g). ES$^+$ (M+H)$^+$ 167

(E)-3-(1-methyl-1H-pyrazol-4-yl)acrylic acid (E)-methyl 3-(1-methyl-1H-pyrazol-4-yl)acrylate (0.24 g, 1.45 mmol) was dissolved in MeOH (10 mL). A 1M solution of KOH (5.8 mL) was added and the mixture was heated at 70° C. overnight. The reaction mixture was then evaporated under reduced pressure and water (10 mL) was added to the residue. This solution was carefully acidified to pH 4 with a 3M aqueous solution of HCl. The carboxylic acid precipitated and was extracted with ethyl acetate. The EtOAc layer was washed with water (2×10 mL) and brine (1×15 mL). It was dried over sodium sulfate, filtered and evaporated under vacuum to give (E)-3-(1-methyl-1H-pyrazol-4-yl)acrylic acid as a white solid (160 mg). ES$^+$ (M+H)$^+$ 153

(E)-tert-butyl (5-fluoro-2-(3-(1-methyl-1H-pyrazol-4-yl)acrylamido)phenyl)carbamate DIPEA (0.16 g, 1.20 mmol), 4-fluoro-tert-butyl-2-aminophenylcarbamate (0.14 g, 0.64 mmol) and HATU (0.20 g, 0.52 mmol) were added to a solution of (E)-3-(1-methyl-1H-pyrazol-4-yl)acrylic acid (0.061 g, 0.401 mmol) in DCM (10 mL). The reaction mixture was stirred overnight at room temperature under nitrogen. After completion of the reaction as indicated by HPLC, the organic solution was washed with saturated NaHCO$_3$ then brine. It was dried over Na$_2$SO$_4$ and the solvent was evaporated. Crude (E)-tert-butyl (5-fluoro-2-(3-(1-methyl-1H-pyrazol-4-yl)acrylamido)phenyl)carbamate was purified by column chromatography using a 20-80% gradient of EtOAc in hexanes to give the title compound (0.15 g) as an off-white solid. ES$^+$ (M+H)$^+$ 361.

(E)-N-(2-amino-4-fluorophenyl)-3-(1-methyl-1H-pyrazol-4-yl)acrylamide (E)-tert-butyl (5-fluoro-2-(3-(1-methyl-1H-pyrazol-4-yl)acrylamido)phenyl)carbamate (0.15 g, 0.42 mmol) was dissolved in dioxane (4 mL). A 4M solution of HCl in dioxane (4 mL) was added and the mixture was stirred at room temperature for 3 h. Salt precipitation was observed. The reaction mixture was then diluted with diethyl ether (20 mL) and the crude hydrochloride salt was filtered. It was stirred with saturated sodium bicarbonate (excess) and filtered. The precipitate was washed with water and vacuum dried. (E)-N-(2-amino-4-fluorophenyl)-3-(1-methyl-1H-pyrazol-4-yl) acrylamide (73 mg) was obtained as an off-white solid. $^1$H NMR (CD$_3$OD) δ: 7.88 (s, 1H), 7.77 (s, 1H), 7.53 (d, J=15.7 Hz, 1H), 7.12 (dd, J=8.5, 5.9 Hz, 1H), 6.54 (d, J=15.9 Hz, 1H), 6.55 (dd, J=10.5, 3.0 Hz, 1H), 6.39 (td, J=8.5, 2.7 Hz, 1H), 3.90 (s, 4H); ES$^+$ (M+H)$^+$ 261.

Example 6: (E)-N-(2-amino-4-fluorophenyl)-3-(1-methyl-1H-pyrazol-4-yl)acrylamide C3

(E)-tert-butyl (4-fluoro-2-(3-(1-methyl-1H-pyrazol-4-yl)acrylamido)phenyl)carbamate The protocol described above for the synthesis of (E)-tert-butyl (4-fluoro-2-(3-(1-methyl-1H-pyrazol-4-yl)acrylamido)phenyl)carbamate was used substituting 4-fluoro-tert-butyl-2-aminophenylcarbamate (0.14 g, 0.64 mmol) for the 5-fluoro analog. Thus starting from (E)-3-(1-methyl-1H-pyrazol-4-yl)acrylic acid (0.061 g, 0.401 mmol) in DCM (10 mL), 0.10 g of pure (E)-tert-butyl (4-fluoro-2-(3-(1-methyl-1H-pyrazol-4-yl)acrylamido) phenyl)carbamate were obtained as an off-white solid after silica gel chromatography. ES$^+$ (M+H)$^+$ 361.

(E)-N-(2-amino-5-fluorophenyl)-3-(1-methyl-1H-pyrazol-4-yl)acrylamide

Protecting group removal was effected by addition of a 4M solution of HCl in dioxane (2.5 mL) to a solution of (E)-tert-butyl (4-fluoro-2-(3-(1-methyl-1H-pyrazol-4-yl) acrylamido) phenyl)carbamate (0.10 g, 0.28 mmol) in dioxane (2.5 mL). The mixture was stirred at room temperature for 3 h. The reaction mixture was diluted with diethyl ether (20 mL) and the hydrochloride salt of (E)-N-(2-amino-5-fluorophenyl)-3-(1-methyl-1H-pyrazol-4-yl)acrylamide precipitated was filtered. It was suspended in a saturated sodium bicarbonate solution and the mixture was stirred. The solid was filtered and washed with water then dried under vacuum to give the pure product (58 mg) as an off-white solid. ES$^+$ (M+H)$^+$ 261.

Table: method 3

| Compound | Structure | R—(RO)$_2$P(O)CH$_2$CO$_2$R | diamine | MS | NMR |
|---|---|---|---|---|---|
| C1 | (1-ethyl-pyrazol-4-yl) CH=CH-C(O)NH-(2-aminophenyl) | CH$_3$—CH$_2$— | Boc-NH-(2-aminophenyl) | ES$^+$ (M + H)$^+$ 257 | $^1$H NMR (CD$_3$OD) δ: 7.94 (s, 1H), 7.79 (s, 1H), 7.55 (d, J = 15.7 Hz, 1H), 7.17 (dd, J = 8.0, 1.1 Hz, 1H), 7.04 (td, J = 7.7, 1.4 Hz, 1H), 6.87 (dd, J = 8.0, 1.4 Hz, 1H), 6.74 (td, J = 7.7, 1.4 Hz, 1H), 6.57 (d, J = 15.7 Hz, 1H), 4.20 (q, J = 7.4 Hz, 2H), 1.47 (t, J = 7.4 Hz, 3H) |
| C2 | (1-methyl-pyrazol-4-yl) CH=CH-C(O)NH-(2-amino-4-fluorophenyl) | CH$_3$— | Boc-NH-(2-amino-5-fluorophenyl) | ES$^+$ (M + H)$^+$ 261 | $^1$H NMR (CD$_3$OD) δ: 7.88 (s, 1H), 7.77 (s, 1H), 7.53 (d, J = 15.7 Hz, 1H), 7.12 (dd, J = 8.5, 5.9 Hz, 1H), 6.54 (d, J = 15.7 Hz, 1H), 6.55 (dd, J = 10.5, 3.0 Hz, 1H), 6.39 (td, J = 8.5, 2.7 Hz, 1H), 3.90 (s, 3H) |
| C3 | (1-methyl-pyrazol-4-yl) CH=CH-C(O)NH-(2-amino-5-fluorophenyl) | CH$_3$— | Boc-NH-(2-amino-4-fluorophenyl) | ES$^+$ (M + H)$^+$ 261 | $^1$H NMR (CD$_3$OD) δ: 7.89 (s, 1H), 7.77 (s, 1H), 7.56 (d, J = 15.7 Hz, 1H), 7.13 (dd, J = 9.9, 2.7 Hz, 1H), 6.78 (td, J = 8.5, 2.7 Hz, 1H), 6.84 (dd, J = 8.8, 5.8 Hz, 1H), 6.56 (d, J = 15.7 Hz, 1H), 3.90 (s, 3H) |

Method D

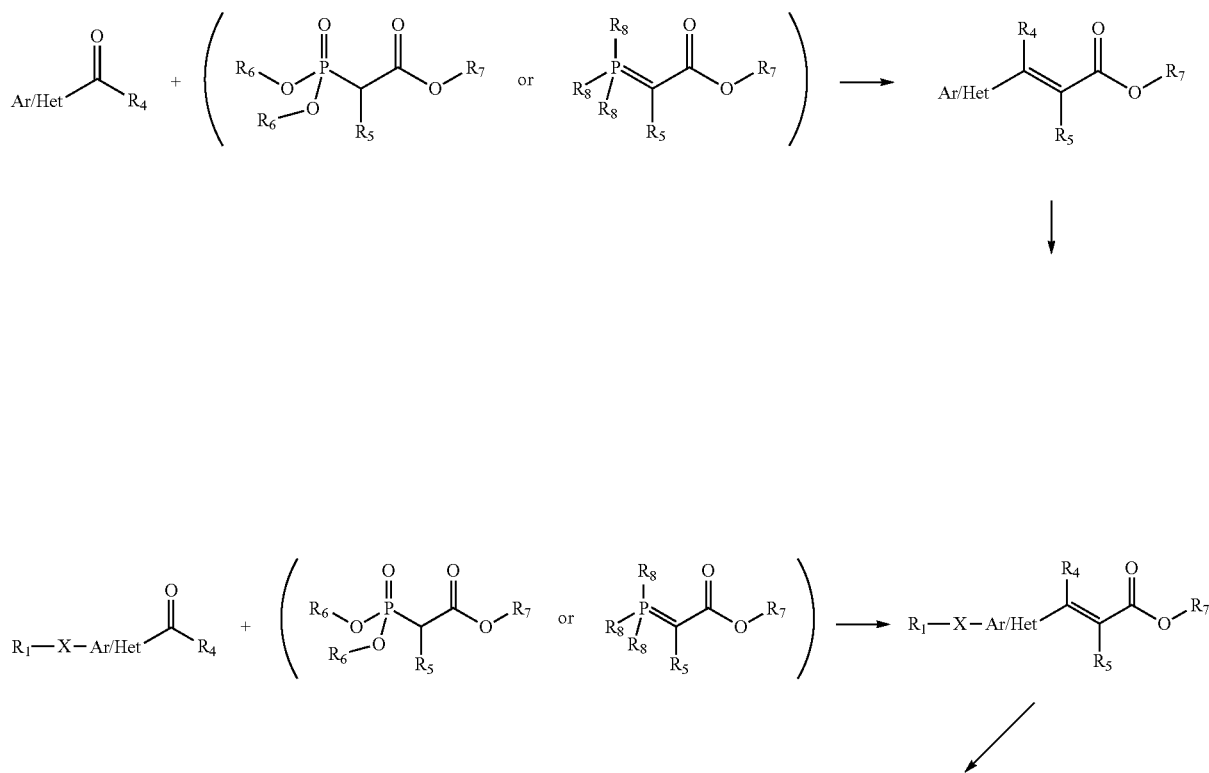

-continued

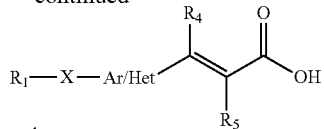

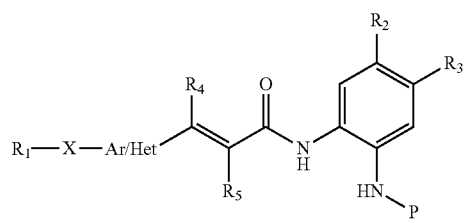

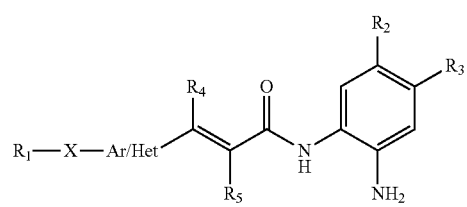

Compounds described herein, where n=1, and R1, X, R2, R3, R4, R5, and Ar/Het are defined as defined anywhere herein, can be prepared by reaction of a mono or bicyclic heterocycle aldehyde or ketone, which can be prepared by methods well known to those skilled in the art and detailed in, for example, Joule J A and Mills K, Heterocyclic Chemistry, Fifth Edition, John Wiley & Sons, Inc., Hoboken, N.J., USA, with a dialkoxyphosphoryl acetic acid ester or a trialkyl, or triphenyl phosphoranylidene acetic acid ester to give the corresponding γ-(heterocycle)acrylate ester Ar/Het-CR4=CR5-COOR7. The R1-X-moiety can then be added to this intermediate by synthetic methods well known to those skilled in the art, including but not limited to Heck coupling, Suzuki reaction, alkylation, acylation. Alternatively the R1-X-substituent can be coupled to the aldehyde or ketone prior to the Wittig or Horner-Wadsworth-Emmons reaction to give the same intermediate ester. The ester can then be hydrolyzed and the acid reacted with a protected or unprotected substituted or unsubstituted o-phenylenediamine to give compounds of the invention after deprotection if required using methods well known to those skilled in the art and which are described for example in P. G. M. Wuts and T. W. Greene, 2006, Greene's Protective Groups in Organic Synthesis, Fourth Edition, John Wiley & Sons, Inc., Hoboken, N.J., USA.

Example 7: (E)-N-(2-aminophenyl)-3-(1-(2-phenoxyethyl)-1H-pyrazol-4-yl)acrylamide D3
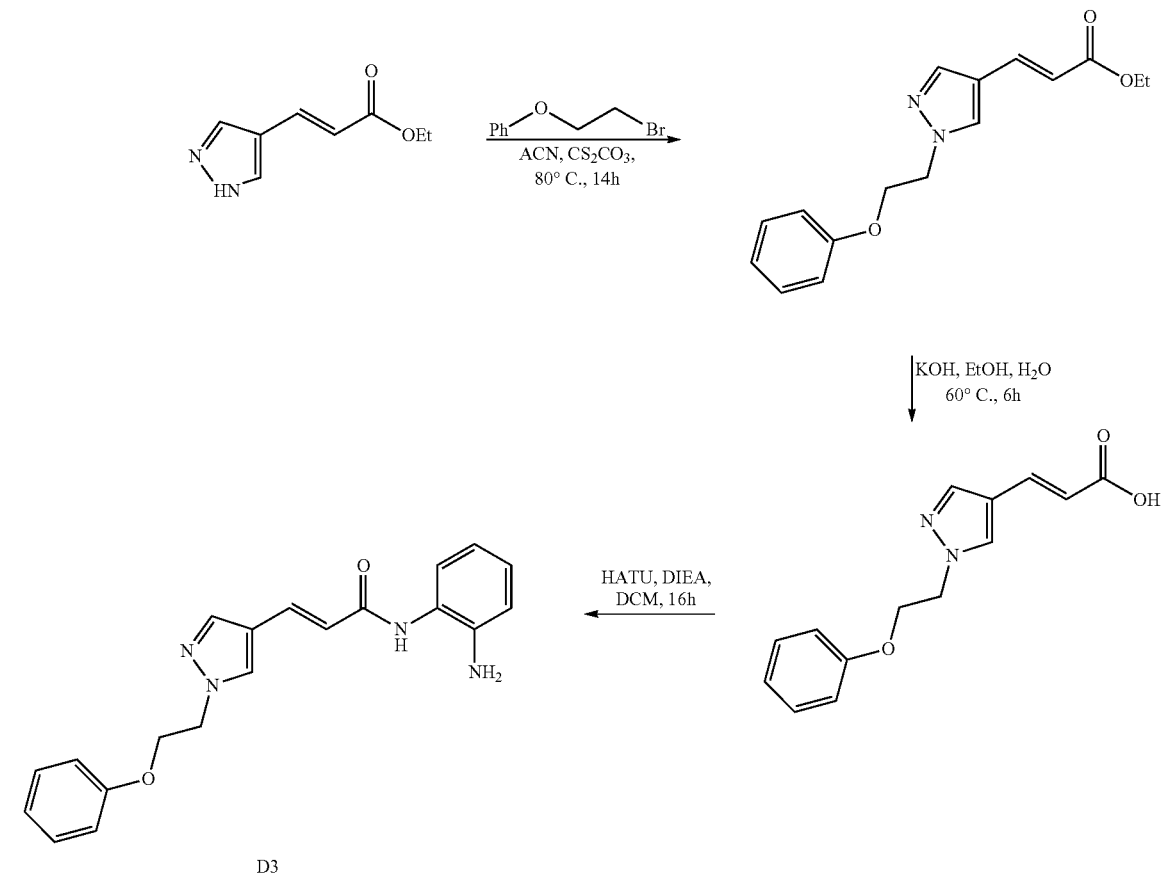
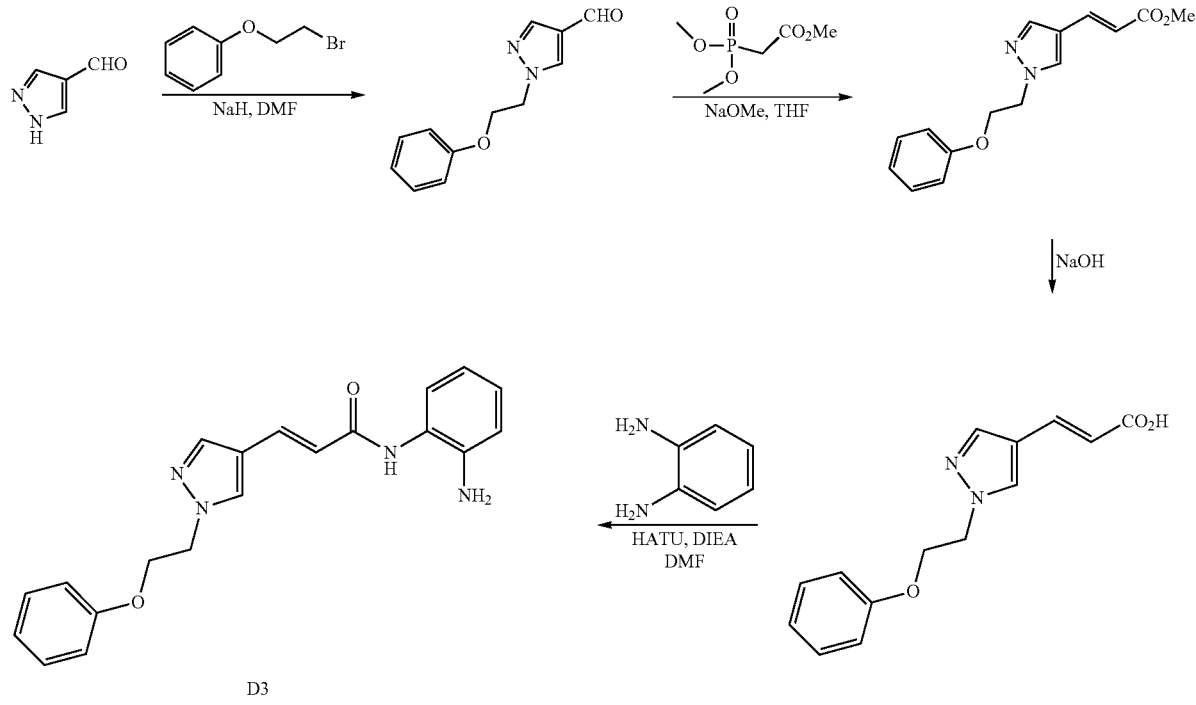

(E)-ethyl 3-(1-(2-phenoxyethyl)-1H-pyrazol-4-yl)acrylate

Cesium carbonate (0.490 g, 1.5 mmol) and 1-(2-bromoethoxy)benzene (0.261 g, 1.30 mmol) were added to a solution of (E)-ethyl 3-(1H-pyrazol-4-yl)acrylate (0.167 g, 1 mmol) in ACN (8 mL) at room temperature. The suspension was stirred overnight at 80° C. The reaction mixture was then cooled down to room temperature and the precipitated solids were filtered off. The filtrate was concentrated and purified by silica gel column chromatography using a gradient of 0-60% of EtOAc in hexanes to provide the title compound (0.203 g, 71%) as a colorless oil. ES$^+$ (M+H)$^+$ 287

(E)-3-(1-(2-phenoxyethyl)-1H-pyrazol-4-yl)acrylic acid

To a solution of (E)-ethyl 3-(1-(2-phenoxyethyl)-1H-pyrazol-4-yl)acrylate (0.143 g, 0.5 mmol) in EtOH (6 mL) was added KOH (0.168 g, 3 mmol) in water (2 mL) and the solution was heated at 60° C. for 6 h. The reaction mixture was then evaporated under vacuum and water (10 mL) was added to the residue. This solution was acidified to pH 4 with aqueous 3N HCl and extracted with EtOAc. The organic extracts were washed with water and brine, dried over Na$_2$SO$_4$ and evaporated in vacuo to get the acid (0.117 g, 91%) as a white solid. ES$^+$ (M+H)$^+$ 259

Alternate Synthesis: 1-(2-phenoxyethyl)-1H-pyrazole-4-carbaldehyde

Sodium hydride (60%, 6.3 g, 1.0 eq) was added to a solution of 1H-pyrazole-4-carbaldehyde (15 g, 156 mmol) in DMF (150 ml) at 0° C. The mixture was allowed to warm and was stirred at room temperature. (2-Bromoethoxy)benzene (30.2 g, 1 eq) was then added and the resulting mixture was stirred overnight at room temperature. It was quenched by addition of aqueous ammonium chloride, diluted with water and extracted with EtOAc. The combined organic layers were dried over Na$_2$SO$_4$, filtered, and concentrated. The residue was purified by column chromatography using a hexane/EtOAc gradient (10:1 to 0:100). Pure fractions were combined and evaporated under reduced pressure to yield 1-(2-phenoxyethyl)-1H-pyrazole-4-carbaldehyde (24 g, 71%).

Alternate Synthesis: (E)-methyl 3-(1-(2-phenoxyethyl)-1H-pyrazol-4-yl)acrylate Trimethyl phosphonoacetate (20.6 g, 112 mmol) was dissolved in 350 mL THF. A 25% w/w NaOMe solution (25 mL) was then added at room temperature and the resulting mixture was stirred for 30 min. 1-(2-Phenoxyethyl)-1H-pyrazole-4-carbaldehyde (24 g, 111 mmol) dissolved in 150 mL THF was added and the reaction mixture was stirred for 5 h before being quenched with aqueous ammonium chloride and extracted with EtOAc. The combined organic layers were dried over Na$_2$SO$_4$, filtered, and concentrated under vacuum. The residue was purified by column chromatography using a gradient of hexane/EtOAc (30:1 to 1:2) to yield (E)-methyl 3-(1-(2-phenoxyethyl)-1H-pyrazol-4-yl)acrylate (22 g, 72.7%).

Alternate Synthesis: (E)-3-(1-(2-phenoxyethyl)-1H-pyrazol-4-yl)acrylic acid

A 3M aqueous solution of NaOH (80 mL) was added to a solution of (E)-methyl 3-(1-(2-phenoxyethyl)-1H-pyrazol-4-yl)acrylate (22 g, 81 mmol) in MeOH (150 mL) at room temperature and the mixture was stirred overnight. The solvent was evaporated under reduced pressure. The concentrated solution was washed with diethylether, acidified to pH=2 with dilute HCl, and extracted with dichloromethane. The combined organic extracts were washed with water and brine, before being dried over Na$_2$SO$_4$. Salts were filtered and washed and the filtrate was evaporated under reduced pressure. The product precipitated from the concentrated solution upon standing. It was filtered and dried under vacuum to give the corresponding (E)-3-(1-(2-phenoxyethyl)-1H-pyrazol-4-yl)acrylic acid (18 g, 86%).

(E)-N-(2-aminophenyl)-3-(1-(2-phenoxyethyl)-1H-pyrazol-4-yl)acrylamide, D3

HATU (0.228 g, 0.60 mmol), DIPEA (0.258 g, 2.00 mmol) and o-phenylenediamine (0.129 g, 1.20 mmol) were added to a solution of ((E)-3-(1-(2-phenoxyethyl)-1H-pyrazol-4-yl)acrylic acid (0.103 g, 0.40 mmol) in DCM (25 mL). The solution was stirred overnight at room temperature. Solvents were evaporated in vacuo and the residue was taken up in EtOAc (40 mL). This solution was washed with saturated NaHCO$_3$ and brine, dried (Na$_2$SO$_4$) and evaporated. The crude product was purified by silica gel column chromatography (gradient of 0-80% EtOAc in hexanes) to get D3 as an off-white solid (0.094 g, 68%). $^1$H NMR (CD$_3$OD) δ: 8.01 (s, 1H), 7.82 (s, 1H), 7.55 (d, J=15.8 Hz, 1H), 7.21-7.31 (m, 2H), 7.17 (dd, J=8.0, 1.1 Hz, 1H), 7.03 (td, J=7.8, 1.2 Hz, 1H), 6.81-6.97 (m, 4H), 6.73 (td, J=7.6, 1.4 Hz, 1H), 6.58 (d, J=15.7 Hz, 1H), 4.53 (t, J=5.1 Hz, 2H), 4.34 (t, J=5.0 Hz, 2H); ES$^+$ (M+H)$^+$ 349.

Example 8: Hydrochloride Salt of (E)-N-(2-amino-4-fluorophenyl)-3-(1-cinnamyl-1H-pyrazol-4-yl)acrylamide D2

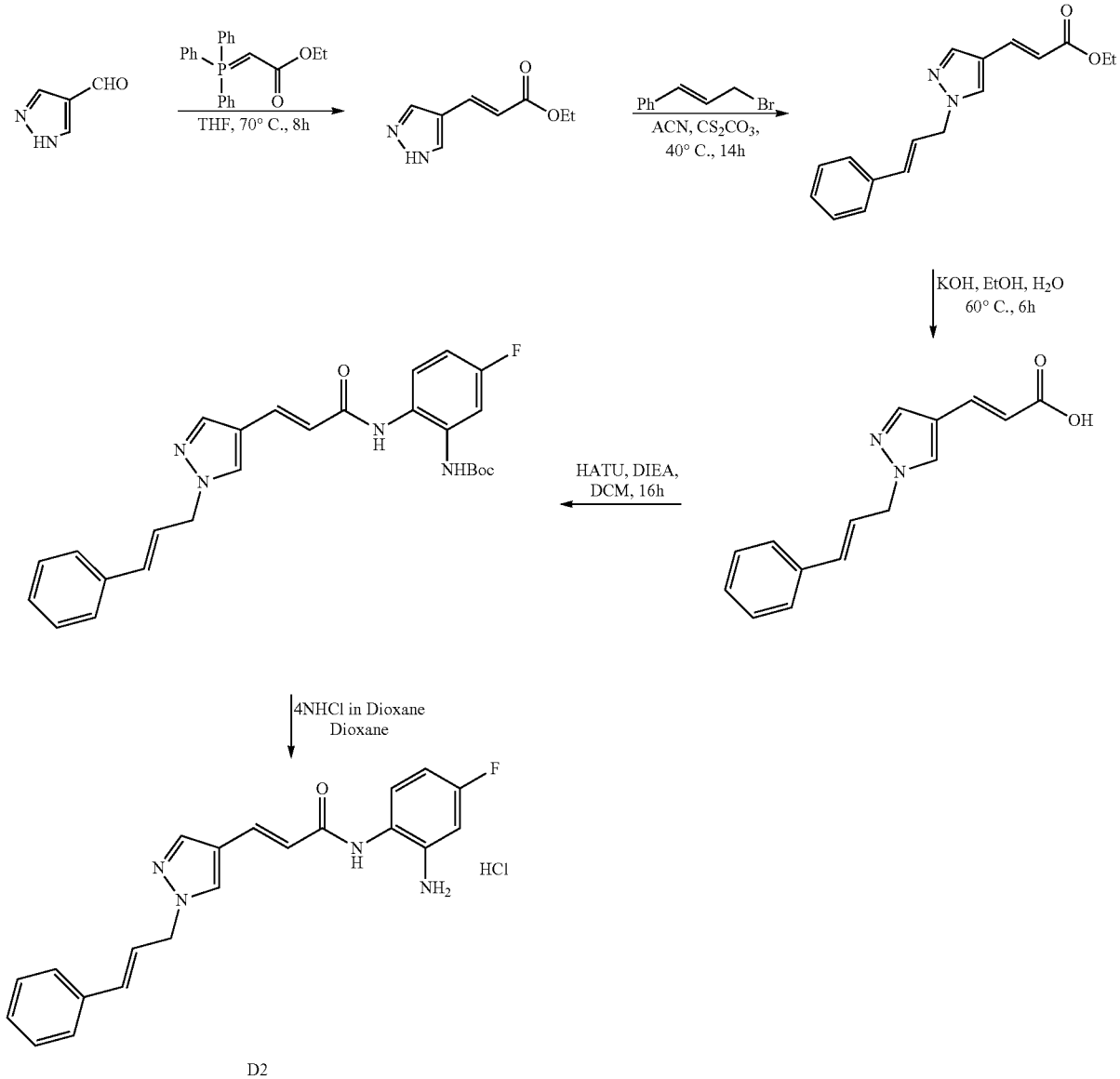

D2

(E)-ethyl 3-(1H-pyrazol-4-yl)acrylate

[(Ethoxycarbonyl)methylene]triphenylphosphorane (0.836 g, 2.4 mmol) was added to a solution of 1H-pyrazole-4-carbaldehyde (0.192 g, 2 mmol) in THF (6 mL) at room temperature. This solution was heated at 70° C. under a nitrogen atmosphere for 8 h. HPLC/MS analysis indicated completion of the reaction and both E and Z isomers of product were observed. The reaction mixture was cooled down to room temperature and evaporated in vacuo to get the crude product. This crude was purified by silica gel column chromatography using 0-80% EtOAc in hexanes as eluent to provide, after evaporation of pooled fractions, pure (E)-ethyl 3-(1H-pyrazol-4-yl)acrylate (0.198 g, 60%) as a white solid. ES$^+$ (M+H)$^+$ 167

(E)-ethyl 3-(1-cinnamyl-1H-pyrazol-4-yl)acrylate

Cesium carbonate (0.490 g, 1.5 mmol) was added to a solution of (E)-ethyl 3-(1H-pyrazol-4-yl)acrylate (0.167 g, 1 mmol) in ACN (8 mL) at room temperature. The suspension was stirred and 1-((E)-3-bromoprop-1-enyl)benzene (0.256 g, 1.30 mmol) was added. The mixture was heated at 40° C. overnight. After cooling down to room temperature, the precipitated solids were filtered off. The filtrate was concentrated and purified by silica gel column chromatography using a 0-60% gradient of EtOAc in hexanes to provide the title compound as a colorless oil (0.214 g, 76%). ES$^+$ (M+H)$^+$ 283

(E)-3-(1-cinnamyl-1H-pyrazol-4-yl)acrylic acid

The ethyl ester of (E)-3-(1-cinnamyl-/H-pyrazol-4-yl) acrylic acid (0.141 g, 0.5 mmol) dissolved in ethanol (EtOH, 6 mL) was hydrolyzed by addition of a solution of KOH (0.168 g, 3 mmol) in water (2 mL). The mixture was heated to 60° C. and the temperature was maintained for 6 h. Solvents were then evaporated under vacuum and water (10 mL) was added to the residue. This solution was carefully acidified to pH 4 with a 3M solution of HCl in water and extracted with EtOAc. The organic layer was washed with water and brine. It was dried ($Na_2SO_4$), filtered and evaporated to give the acid as a white solid (0.118 g, 93%). ES$^+$ (M+H)$^+$ 255 tert-Butyl (2-((E)-3-(1-cinnamyl-1H-pyrazol-4-yl) acrylamido)-5-fluorophenyl)carbamate (E)-3-(1-cinnamyl-/H-pyrazol-4-yl)acrylic acid (0.110 g, 0.43 mmol) was dissolved in DCM (25 mL). HATU (0.246 g, 0.65 mmol), DIPEA (0.278 g, 2.15 mmol) and tert-butyl 2-amino-5-fluorophenylcarbamate (0.147 g, 0.65 mmol) were added and the mixture was stirred overnight at room temperature under nitrogen. Slovents were evaporated and the residue was taken up in EtOAc (40 mL). It was then washed with saturated $NaHCO_3$ and brine, dried over $Na_2SO_4$, filtered and evaporated in vacuo to get the crude. The product was purified by silica gel column chromatography using a gradient of 0-70% EtOAc in hexanes to get tert-butyl (2-((E)-3-(1-cinnamyl-1H-pyrazol-4-yl)acrylamido)-5-fluorophenyl)carbamate5 (0.138 g, 76%) as an off-white solid. ES$^+$ (M+Na)$^+$ 485.

Hydrochloride Salt of (E)-N-(2-amino-4-fluorophenyl)-3-(1-cinnamyl-1H-pyrazol-4-yl)acrylamide A 4M solution of HCl in dioxane (4 mL) was mixed under nitrogen with a solution of tert-butyl (2-((E)-3-(1-cinnamyl-1H-pyrazol-4-yl)acrylamido)-5-fluorophenyl)carbamate (0.138 g, 0.30 mmol) in dioxane (12 mL). The mixture was stirred for 4 h at room temperature under nitrogen. Salt precipitation was observed. The heterogeneous mixture was diluted with EtOAc (12 mL) and the precipitate was filtered, washed with solvent and dried overnight under vacuum to get the pure hydrochloride salt of (E)-N-(2-amino-4-fluorophenyl)-3-(1-cinnamyl-1H-pyrazol-4-yl)acrylamide (0.110 g, 92%) as an off-white solid. $^1$H NMR (CD$_3$OD) δ: 8.08 (s, 1H), 7.90 (s, 1H), 7.71 (d, J=15.5 Hz, 1H), 7.37-7.46 (m, 2H), 7.21-7.37 (m, 4H), 6.63 (d, J=15.7 Hz, 1H), 6.56-6.71 (m, 1H), 6.43 (dt, J=15.8, 6.2 Hz, 1H), 4.96 (dd, J=6.3, 1.1 Hz, 2H); ES$^+$ (M+H)$^+$ 363

| Compound | Structure | R1—X— coupling reagent |
|---|---|---|
| D1 | 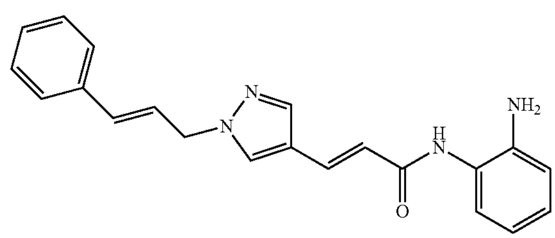 [SMILES: Nc1ccccc1NC(=O)/C=C/c1cnn(C/C=C/c2ccccc2)c1] | |
| D2 | 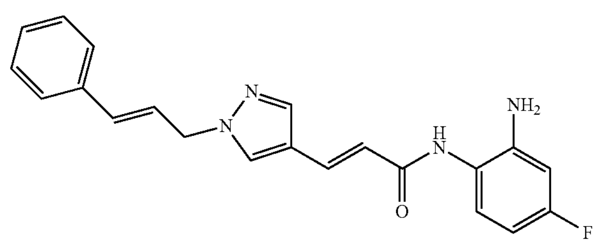 [SMILES: Nc1cc(F)ccc1NC(=O)/C=C/c1cnn(C/C=C/c2ccccc2)c1] | |
| D3 | 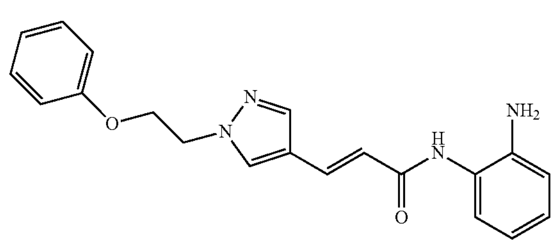 [SMILES: Nc1ccccc1NC(=O)/C=C/c1cnn(CCOc2ccccc2)c1] | |
| D4 | 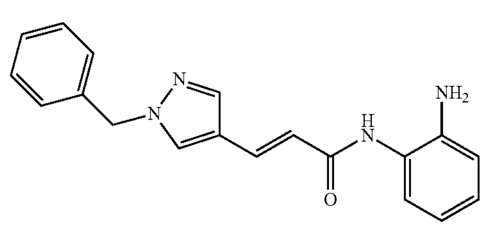 [SMILES: Nc1ccccc1NC(=O)/C=C/c1cnn(Cc2ccccc2)c1] | |

| | | |
|---|---|---|
| D5 | 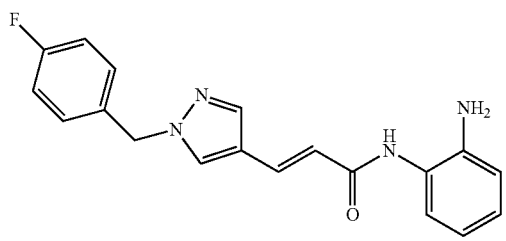 [SMILES: Nc1ccccc1NC(=O)/C=C/c1cnn(Cc2ccc(F)cc2)c1] | 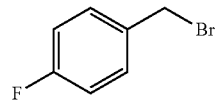 |
| D6 | 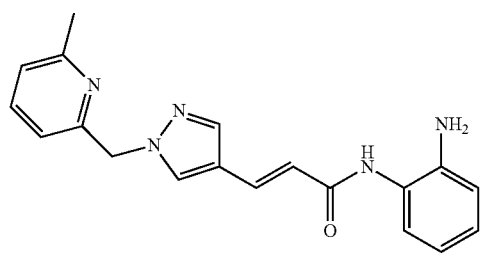 [SMILES: Cc1cccc(Cn2cc(/C=C/C(=O)Nc3ccccc3N)cn2)n1] | 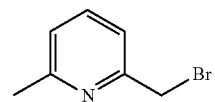 |
| D7 | 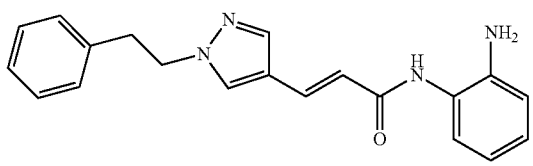 [SMILES: Nc1ccccc1NC(=O)/C=C/c1cnn(CCc2ccccc2)c1] | 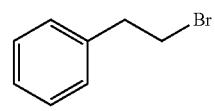 |
| D8 | 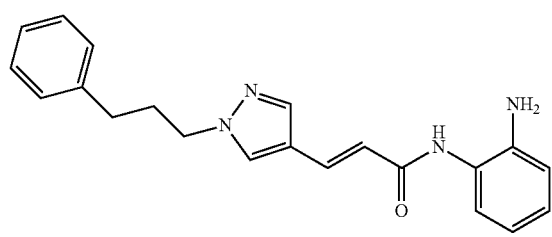 [SMILES: Nc1ccccc1NC(=O)/C=C/c1cnn(CCCc2ccccc2)c1] | 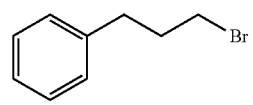 |
| D9 | 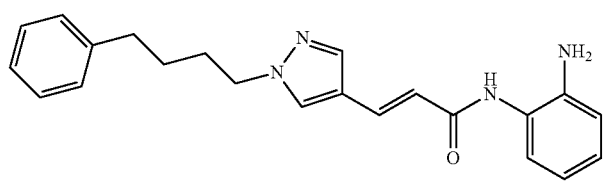 [SMILES: Nc1ccccc1NC(=O)/C=C/c1cnn(CCCCc2ccccc2)c1] | 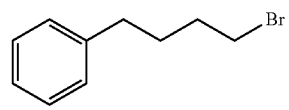 [SMILES: BrCCCCc1ccccc1] |
| D10 | 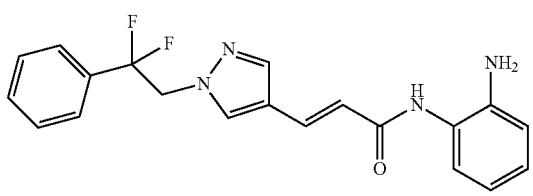 [SMILES: Nc1ccccc1NC(=O)/C=C/c1cnn(CC(F)(F)c2ccccc2)c1] | 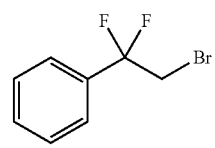 [SMILES: FC(F)(CBr)c1ccccc1] |
| D11 | 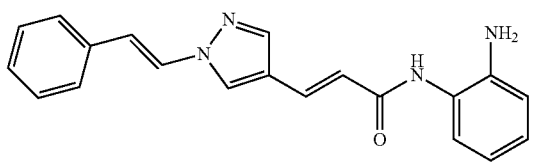 [SMILES: Nc1ccccc1NC(=O)/C=C/c1cnn(/C=C/c2ccccc2)c1] | 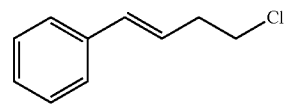 [SMILES: ClCC/C=C/c1ccccc1] |

-continued
| | | |
|---|---|---|
| D12 | 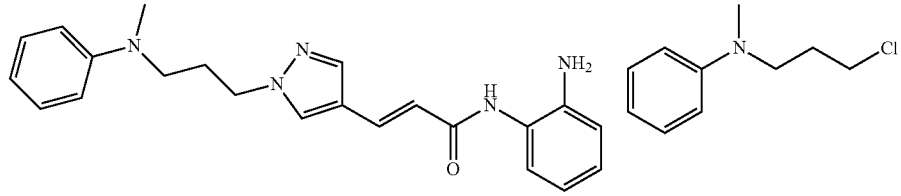 | |
| D13 | 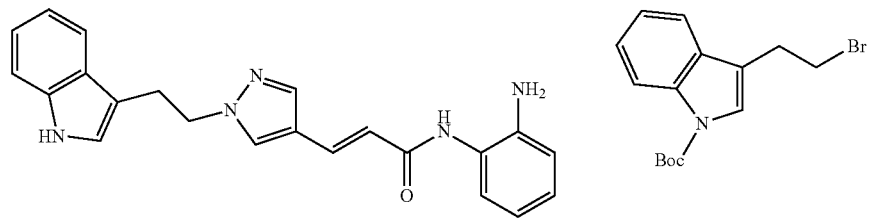 | |
| D14 | 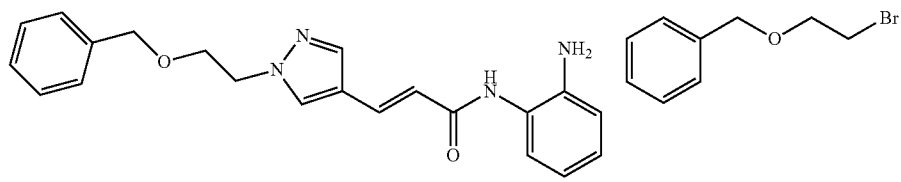 | |
| D15 | 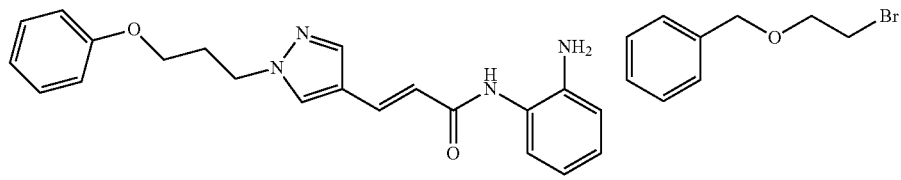 | |
| D16 | 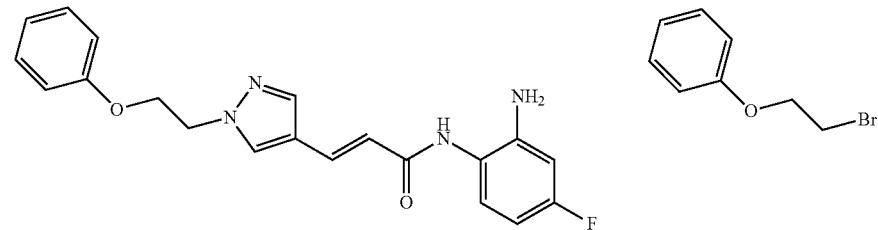 | |
| Compound | Diamine | MS | NMR |
|---|---|---|---|
| D1 | 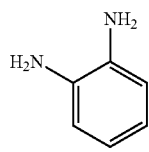 | ES⁺ (M + H)⁺ 345 | ¹H NMR (CD$_3$OD) δ: 7.98 (s, 1H), 7.83 (s, 1H), 7.56 (d, J = 15.8 Hz, 1H), 7.36-7.46 (m, 2H), 7.20-7.36 (m, 3H), 7.17 (dd, J = 8.1, 1.1 Hz, 1H), 7.03 (td, J = 7.7, 1.2 Hz, 1H), 6.86 (dd, J = 8.4, 1.2 Hz, 1H), 6.73 (td, J = 7.7, 1.4 Hz, 1H), 6.62 (d, J = 15.8 Hz, 1H), 6.59 (d, J = 15.7 Hz, 1H), 6.42 (dt, J = 15.8, 6.2 Hz, 1H), 4.93 (d, J = 6.2 Hz, 2H) |
| D2 | 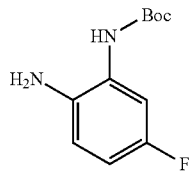 | ES⁺ (M + H)⁺ 363 | ¹H NMR (CD$_3$OD) - HCl salt - δ: 8.08 (s, 1H), 7.90 (s, 1H), 7.71 (d, J = 15.5 Hz, 1H), 7.37-7.46 (m, 2H), 7.21-7.37 (m, 4H), 6.63 (d, J = 15.7 Hz, 1H), 6.56-6.71 (m, 1H), 6.43 (dt, J = 15.8, 6.2 Hz, 1H), 4.96 (dd, J = 6.3, 1.1 Hz, 2H) |

-continued

| | | | |
|---|---|---|---|
| D3 | 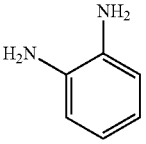 | ES+ (M + H)+ 349 | 1H NMR (CD3OD) δ: 8.01 (s, 1H), 7.82 (s, 1H), 7.55 (d, J = 15.8 Hz, 1H), 7.21-7.31 (m, 2H), 7.17 (dd, J = 8.0, 1.1 Hz, 1H), 7.03 (td, J = 7.8, 1.2 Hz, 1H), 6.81-6.97 (m, 4H), 6.73 (td, J = 7.6, 1.4 Hz, 1H), 6.58 (d, J = 15.7 Hz, 1H), 4.53 (t, J = 5.1 Hz, 2H), 4.34 (t, J = 5.0 Hz, 2H) |
| D4 | 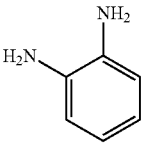 | ES+ (M + H)+ 319 | 1H NMR (CD3OD) δ: 7.98 (s, 1H), 7.82 (s, 1H), 7.55 (d, J = 15.7 Hz, 1H), 7.21-7.41 (m, 5H), 7.17 (dd, J = 7.8, 1.2 Hz, 1H), 7.03 (ddd, J = 8.0, 7.8, 1.1 Hz, 1H), 6.86 (dd, J = 8.0, 1.4 Hz, 1H), 6.73 (td, J = 7.7, 1.1 Hz, 1H), 6.58 (d, J = 15.7 Hz, 1H), 5.35 (s, 2H) |
| D5 | 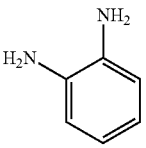 | ES+ (M + H)+ 337 | 1H NMR (CD3OD) δ: 7.99 (s, 1H), 7.82 (s, 1H), 7.54 (d, J = 15.7 Hz, 1H), 7.24-7.38 (m, 2H), 7.17 (dd, J = 8.0, 1.4 Hz, 1H), 6.99- 7.13 (m, 2H), 7.03 (td, J = 7.6, 1.6 Hz, 1H), 6.86 (dd, J = 8.0, 1.4 Hz, 1H), 6.73 (td, J = 7.6, 1.4 Hz, 1H), 6.58 (d, J = 15.7 Hz, 1H), 5.33 (s, 2H) |
| D6 | 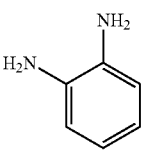 | ES+ (M + H)+ 333 | 1H NMR (CD3OD) δ: 8.07 (s, 1H), 7.85 (s, 1H), 7.68 (t, J = 7.7 Hz, 1H), 7.57 (d, J = 15.8 Hz, 1H), 7.22 (d, J = 7.7 Hz, 2H), 7.18 (dd, J = 7.7, 1.2 Hz, 1H), 7.04 (td, J = 7.7, 1.8 Hz, 1H), 6.87 (dd, J = 8.1, 1.4 Hz, 2H), 6.91 (d, J = 7.7 Hz, 1H), 6.74 (td, J = 7.6, 1.5 Hz, 1H), 6.60 (d, J = 15.7 Hz, 1H), 5.42 (s, 2H), 2.53 (s, 3H) |
| D7 | 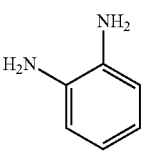 | ES+ (M + H)+ 333 | 1H NMR (CD3OD) δ: 7.80 (s, 1H), 7.62-7.71 (m, 1H), 7.47 (d, J = 15.7 Hz, 1H), 7.13-7.26 (m, 4H), 7.07-7.13 (m, 2H), 7.03 (td, J = 7.7, 1.5 Hz, 1H), 6.86 (dd, J = 8.1, 1.5 Hz, 1H), 6.73 (td, J = 7.6, 1.5 Hz, 1H), 6.51 (d, J = 15.7 Hz, 1H), 4.38 (t, J = 7.0 Hz. 2H), 3.14 (t, J = 7.0 Hz, 2H) |
| D8 | 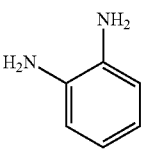 | ES+ (M + H)+ 347 | 1H NMR (CD3OD) δ: 7.92 (s, 1H), 7.81 (s, 1H), 7.55 (d, J = 15.7 Hz, 1H), 7.23-7.35 (m, 2H), 7.12-7.22 (m, 4H), 7.04 (td, J = 7.8, 1.5 Hz, 1H), 6.87 (dd, J = 8.0, 1.4 Hz, 1H), 6.74 (td, J = 7.6, 1.4 Hz, 1H), 6.57 (d, J = 15.7 Hz, 1H), 4.16 (t, J = 7.0 Hz, 3H), 2.60 (t, J = 7.7 Hz, 3H), 2.18 (tt, J = 7.7, 7.0 Hz, 3H) |
| D9 | 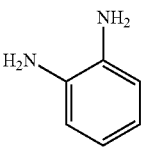 | ES+ (M + H)+ 361 | 1H NMR (CD3OD) δ: 7.90 (s, 1H), 7.79 (s, 1H), 7.54 (d, J = 15.7 Hz, 1H), 7.20-7.31 (m, 2H), 7.09-7.20 (m, 4H), 7.03 (td, J = 7.5, 1.4 Hz, 1H), 6.87 (dd, J = 8.1, 1.2 Hz, 1H), 6.74 (td, J = 7.5, 1.5 Hz, 1H), 6.56 (d, J = 15.7 Hz, 1H), 4.17 (t, J = 7.0 Hz, 2H), 2.63 (t, J = 7.6 Hz, 2H), 1.88 (quin, J = 7.0Hz, 2H), 1.59 (tt, J = 7.6. 7.0 Hz, 2H) |
| D10 | 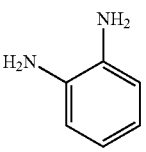 | ES+ (M + H)+ 369 | 1H NMR (CD3OD) δ: 7.85 (s, 1H), 7.78 (s, 1H), 7.5 (d, J = 15.6 Hz, 1H), 7.46-7.40 (m, 5H), 7.17 (dd, J = 8.1, 1.5 Hz, 1H), 7.04 (td, J = 7.2, 1.5 Hz, 1H), 6.86 (dd, J = 8.1, 1.2 Hz, 1H), 6.73 (td, J = 8.1, 1.2 Hz, 1H), 6.57 (d, J = 15.6 Hz, 1H), 4.84 (t, J = 13.5 Hz, 2H) |

| | | | |
|---|---|---|---|
| D11 | 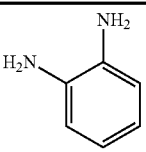 | ES+ (M + H)+ 359 | 1H NMR (CD3OD) δ: 7.94 (s, 1H), 7.81 (s, 1H), 7.53 (d, J = 15.7 Hz, 1H), 7.21-7.39 (m, 4H), 7.11-7.21 (m, 2H), 7.03 (td, J = 7.7, 1.4 Hz, 1H), 6.86 (dd, J = 8.0, 1.2 Hz, 1H), 6.73 (td, J = 7.6, 1.2 Hz, 1H), 6.56 (d, J = 15.5 Hz, 1H), 6.39 (d, J = 16.1 Hz, 1H), 6.18 (dt, J = 15.9, 7.0 Hz, 1H), 4.30 (t, J = 6.9 Hz, 2H), 2.75 (q, J = 6.8 Hz, 2H) |
| D12 | 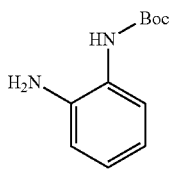 | ES+ (M + H)+ 378 | 1H NMR (CD3OD) δ: 7.90 (s, 1H), 7.83 (s, 1H), 7.55 (d, J = 15.7 Hz, 1H), 7.09-7.23 (m, 3H), 7.03 (td, J = 7.7, 1.2 Hz, 1H), 6.87 (dd, J = 8.0, 1.4 Hz, 1H), 6.74 (td, J = 7.7, 1.2 Hz, 1H), 6.61-6.70 (m, 3H), 6.57 (d, J = 15.8 Hz, 1H), 4.21 (t, J = 6.9 Hz, 2H), 3.33 (t, J = 7.1 Hz, 2H), 2.89 (s, 3H), 2.13 (quin, J = 7.1 Hz, 2H) |
| D13 | 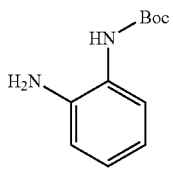 | ES+ (M + H)+ 372 | 1H NMR (CD3OD) δ: 7.81 (s, 1H), 7.63 (s, 1H), 7.48 (br. d, J = 7.7 Hz, 1H), 7.46 (d, J = 15.7 Hz, 1H), 7.32 (br. d, J = 8.2 Hz, 1H), 7.16 (dd, J = 7.9, 1.3 Hz, 1H), 7.08 (m, 3H), 6.88 (s, 1H), 6.86 (dd, J = 8.1, 1.4 Hz, 1H), 6.73 (td, J = 7.6, 1.5 Hz, 1H), 6.49 (d, J = 15.5 Hz, 1H), 4.42 (t, J = 7.0 Hz, 2H), 3.29 (t, J = 7.0 Hz, 2H) |
| D14 | 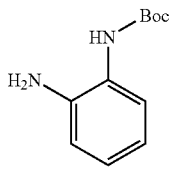 | ES+ (M + H)+ 363 | 1H NMR (CD3OD) δ: 7.94 (s, 1H), 7.80 (s, 1H), 7.56 (d, J = 15.7 Hz, 1H), 7.12-7.35 (m, 6H), 7.04 (td, J = 7.7, 1.2 Hz, 1H), 6.87 (dd, J = 8.1, 1.2 Hz, 1H), 6.74 (td, J = 7.6, 1.4 Hz, 1H), 6.58 (d, J = 15.7 Hz, 1H), 4.48 (s, 2H), 4.34 (t, J = 5.1 Hz, 2H), 3.82 (t, J = 5.1 Hz, 2H) |
| D15 | 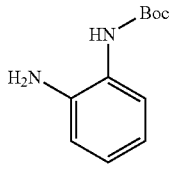 | ES+ (M + H)+ 363 | 1H NMR (CD3OD) δ: 7.96 (s, 1H), 7.83 (s, 1H), 7.62 (d, J = 15.7 Hz, 1H), 7.08-7.37 (m, 6H), 6.81-6.99 (m, 3H), 6.57 (d, J = 15.5 Hz, 1H), 4.38 (t, J = 6.7 Hz, 2H), 3.95 (t, J = 5.8 Hz, 2H), 2.32 (quin, J = 6.4 Hz, 2H) |
| D16 | 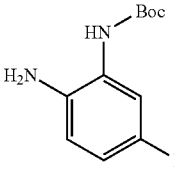 | | |

Method E

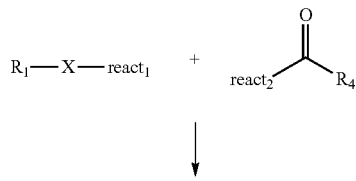

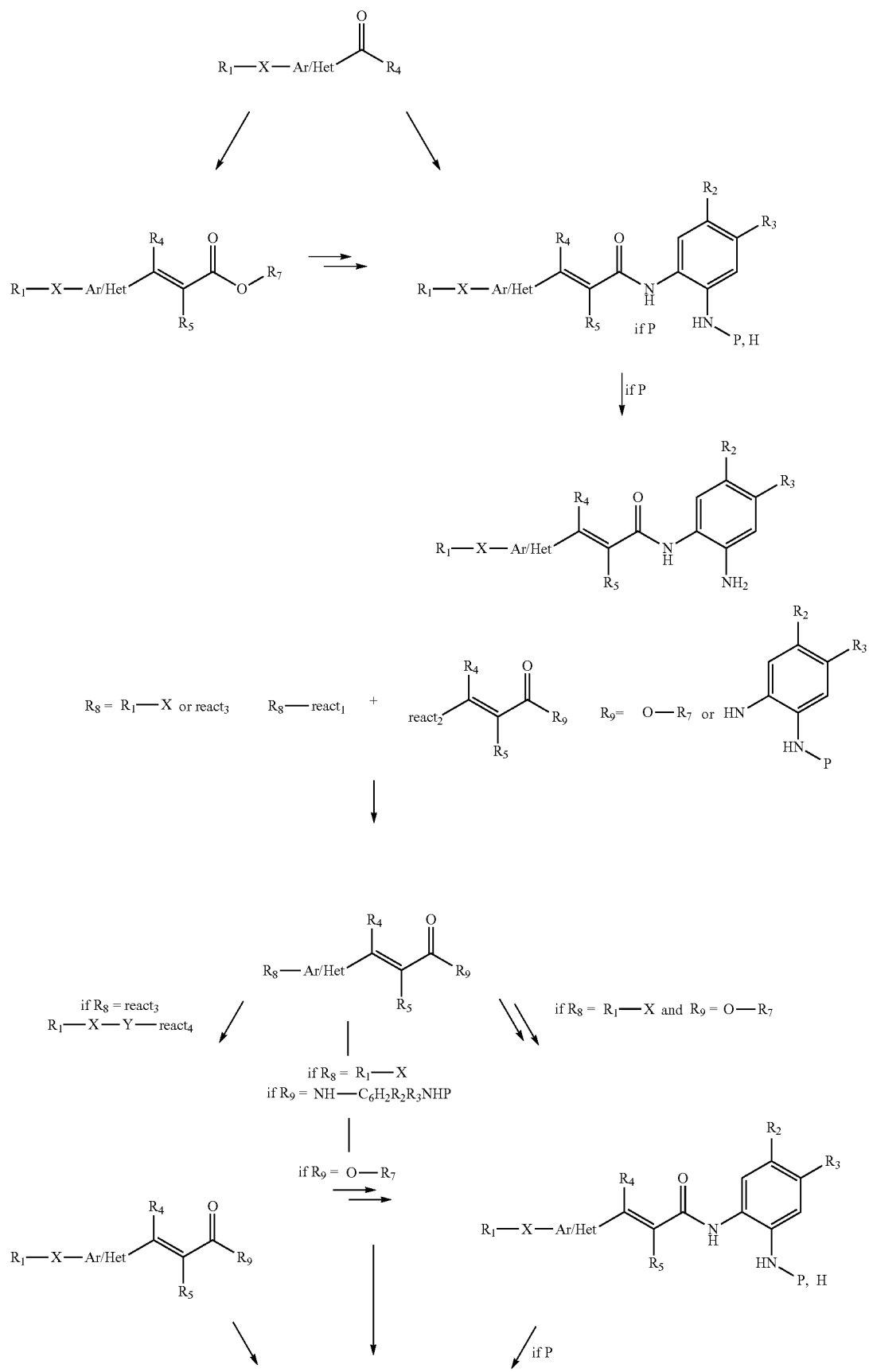

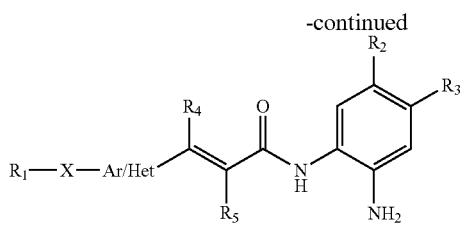

Compounds described herein, where n=1, and R1, X, R2, R3, R4, R5 are as defined anywhere herein, can be prepared by heterocycle ring formation using methods well known to those skilled in the art, examples of which can be found in, for example, Joule J A and Mills K, Heterocyclic Chemistry, Fifth Edition, John Wiley & Sons, Inc., Hoboken, N.J., USA. This methodology allows for synthesis of both monocyclic and bicyclic heterocyclic systems. As compared to previous methods described in this invention, method 5 consists in building a mono or bicyclic system bearing R1-X and/or C(R4)=C(R5)-CONH($C_6H_2$R2R3($NH_2$)) or a protected or unprotected synthetic precursor (see schemes above for generic examples). Thus adequately substituted reagents are coupled to form heterocyclic ring systems using methods such as the Hantsch thiazole synthesis, the Fisher indole synthesis, the Davidson or Robinson-Gabriel oxazole syntheses, as well as other annulation reactions using complementary bifunctional reagents to effect ring closure and aromatization. Similar techniques can be used to prepare bicyclic heterocycles by expanding monocyclic analogs. For example, azabridged triazolothiazoles and triazolooxazoles can be obtained by methods described in, for example, Pilla M et al, Bioorg Med Chem Lett 20 (2010) 7521; pyrazolopyridines can be prepared as detailed in, for example, Riether D et al, J Med Chem 53 (2010) 6681. The synthesis of substituted indolazines has also been detailed in many articles.

Example 9: (E)-N-(2-aminophenyl)-3-(6-(ethoxymethyl)imidazo[2,1-b]thiazol-2-yl)acrylamide E1

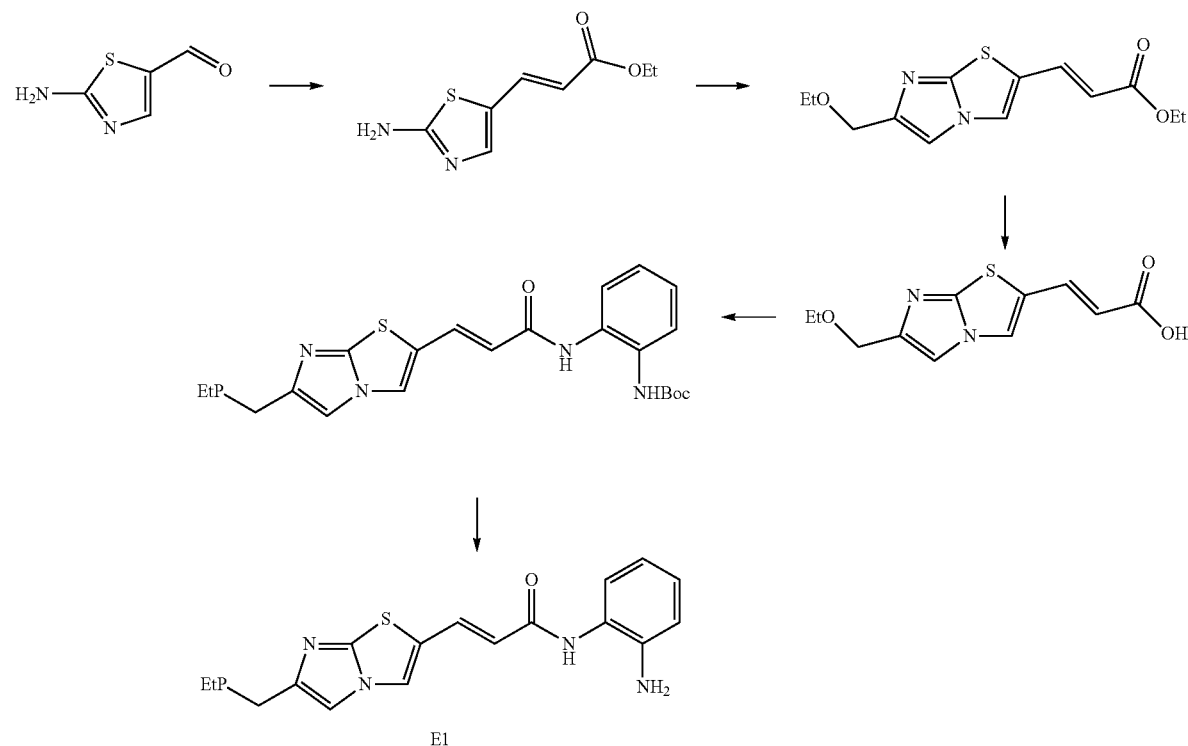

(E)-ethyl 3-(2-aminothiazol-5-yl)acrylate

2-Aminothiazole-5-carbaldehyde (0.25 g, 2 mmol) was dissolved in anhydrous THF (20 mL). (Ethoxycarbonylmethylene)triphenylphosphorane (0.790 g, 2.2 mmol) was added at room temperature and the reaction mixture was heated overnight at 65° C. The reaction mixture was then evaporated under reduced pressure. The residue was purified by silica gel column chromatography using a gradient of 50-80% EtOAc in Hexanes to provide pure (E)-ethyl 3-(2-aminothiazol-5-yl)acrylate (0.24 g) as a white solid. $ES^+$ $(M+H)^+$ 199.

(E)-ethyl 3-(6-(ethoxymethyl)imidazo [2,1-b]thiazol-2-yl)acrylate 1,3-Dichloroacetone (0.252 g, 2 mmol) was added to a solution of (E)-ethyl 3-(2-aminothiazol-5-yl)acrylate (0.199 g, 1 mmol) in EtOH (5 mL). The solution was heated at 80° C. overnight in a closed vial. The reaction mixture was then evaporated and the residue was treated with a saturated NaHCO$_3$ solution (20 mL). It was extracted with EtOAc (30 mL). The organic layer was separated, dried over Na$_2$SO$_4$, filtered and evaporated. The crude was purified by silica gel column chromatography (50-100% gradient of EtOAc in Hexanes) to provide pure (E)-ethyl 3-(6-(ethoxymethyl)imidazo[2,1-b] thiazol-2-yl)acrylate (0.080 g) as a tan solid. ES$^+$ (M+H)$^+$ 281.

(E)-3-(6-(ethoxymethyl)imidazo [2,1-b]thiazol-2-yl) acrylic acid

A solution of (E)-ethyl 3-(6-(ethoxymethyl)imidazo[2,1-b]thiazol-2-yl)acrylate (0.080 g, 0.28 mmol) in EtOH (5 mL) was treated with a 1M aqueous solution of KOH (1 mL). The mixture was heated to 50° C. for 6 h. The reaction mixture was then evaporated under reduced pressure and water (10 mL) was added to the residue. This solution was carefully acidified to pH 4 with 3M aqueous HCl. Since the product was soluble in water, the acidified solution was evaporated in vacuo to get (E)-3-(6-(ethoxymethyl)imidazo [2,1-b]thiazol-2-yl)acrylic acid as an HCl salt along with inorganic solids, which was used for the next step without further purification. ES$^+$ (M+H)$^+$ 253.

(E)-tert-butyl (2-(3-(6-(ethoxymethyl)imidazo [2,1-b]thiazol-2-yl)acrylamido)phenyl) carbamate The crude HCl salt of (E)-3-(6-(ethoxymethyl)imidazo[2,1-b]thiazol-2-yl)acrylic acid (0.080 g, 0.28 mmol, based on (E)-ethyl 3-(6-(ethoxymethyl)imidazo[2,1-b]thiazol-2-yl) acrylate) was suspended in DCM (10 mL. DIPEA (0.22 g, 1.68 mmol), tert-butyl-2-aminophenylcarbamate (0.087 g, 0.42 mmol) and HATU (0.160 g, 0.42 mmol) were added and the reaction mixture was stirred overnight at room temperature under nitrogen. After completion of the reaction as indicated by HPLC, the reaction mixture was washed with saturated NaHCO$_3$ and brine. The organic layer was then dried (Na$_2$SO$_4$), filtered and evaporated under reduced pressure. The crude product was purified by silica gel column chromatography using a gradient of 0 to 8% MeOH in DCM to provide pure (E)-tert-butyl (2-(3-(6-(ethoxymethyl)imidazo [2,1-b]thiazol-2-yl)acrylamido)phenyl) carbamate (0.033 g) as a tan solid. ES$^+$ (M+Na)$^+$ 465.

(E)-N-(2-aminophenyl)-3-(6-(ethoxymethyl)imidazo [2,1-b]thiazol-2-yl)acrylamide (E)-tert-butyl (2-(3-(6-(ethoxymethyl)imidazo [2,1-b]thiazol-2-yl)acrylamido)phenyl) carbamate (0.033 g, 0.071 mmol) was dissolved in dioxane (2 mL). A 4M solution of HCl in dioxane (2. mL) was then added and the mixture stirred at room temperature for 3 h. Salt precipitation was observed. The reaction mixture was then filtered and washed with DCM (3 mL). The white solid was treated with a saturated NaHCO3 solution to neutralize the acid. After washing with water and drying under vacuum, pure (E)-N-(2-aminophenyl)-3-(6-(ethoxymethyl)imidazo [2,1-b]thiazol-2-yl)acrylamide (14 mg) was obtained as a tan solid. ES$^+$ (M+H)$^+$ 343.

Example 10: (E)-N-(2-aminophenyl)-3-(2-cinnamylthiazol-4-yl)acrylamide, E2

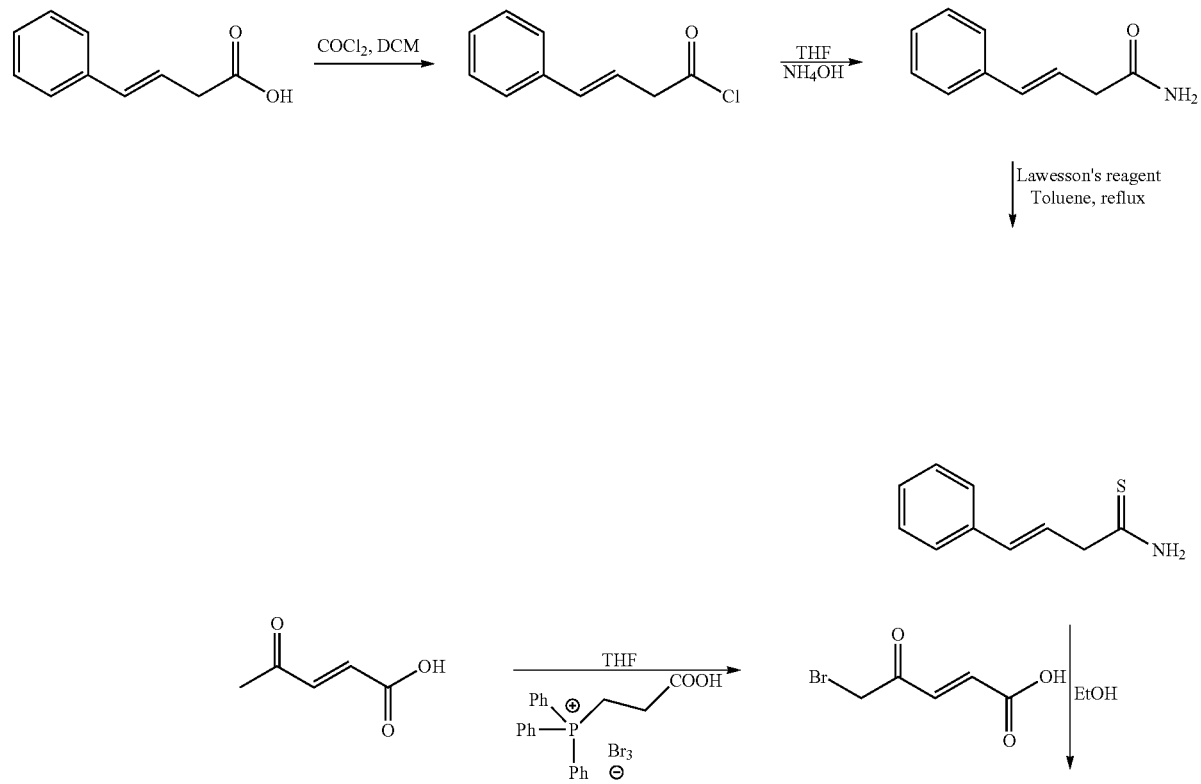

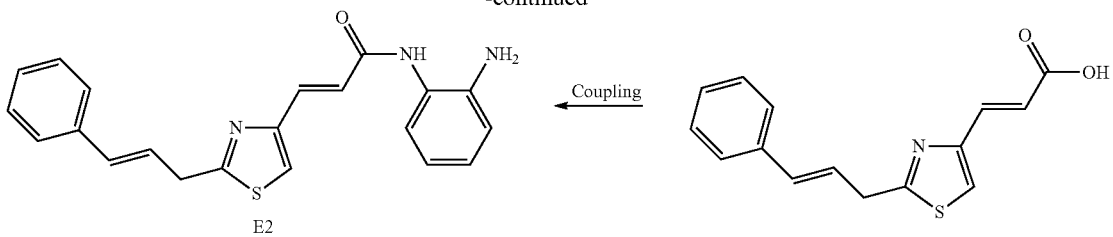

(E)-4-phenylbut-3-enamide

A solution of (E)-4-phenylbut-3-enoic acid (1.5 g, 9.25 mmol) in dichloromethane (100 mL) was cooled to 0° C. Oxalyl chloride (1.76 g, 13.86 mmol) was then added dropwise. After addition of three drops of anhydrous DMF, the reaction mixture was brought to room temperature and stirred for 2 h. Dichloromethane was evaporated under vacuum. The crude residue was dissolved in toluene (25 mL) and concentrated in-vacuo. This operation was repeated two times to give the acid chloride, which was dissolved in THF (30 mL) and treated with aqueous ammonium hydroxide (30%) (20 mL) to give the corresponding amide. Purification by silica gel column chromatography using a 20-100% gradient of EtOAc in hexane gave pure (E)-4-phenylbut-3-enamide (1.3 g) as a white solid.

(E)-4-phenylbut-3-enethioamide

Lawesson's reagent (1.88 g, 4.65 mmol) was added to (E)-4-phenylbut-3-enamide (500 mg, 3.10 mmol) in toluene (25 mL). The reaction mixture was refluxed for 24 h then cooled to room temperature. The solvent was then removed under reduced pressure. The crude residue was purified twice by column chromatography to give >90% pure (E)-4-phenylbut-3-enethioamide (320 mg).

(E)-3-(2-cinnamylthiazol-4-yl)acrylic acid (E)-4-phenylbut-3-enethioamide (120 mg, 0.68 mmol) was dissolved in ethanol (20 mL). (E)-5-bromo-4-oxopent-2-enoic acid (290 mg, 1.50 mmol) was then added at room temperature and the reaction mixture was stirred for 1 h. The solution was concentrated and the crude residue was purified by column chromatography to give (E)-3-(2-cinnamylthiazol-4-yl)acrylic acid (90 mg). ES+ (M+H)+ 272. [Note: (E)-5-bromo-4-oxopent-2-enoic acid was synthesized from commercially available (E)-4-oxopent-2-enoic acid using (2-carboxyethyl)triphenylphosphonium tribromide in THF]

(E)-N-(2-aminophenyl)-3-(2-cinnamylthiazol-4-yl)acrylamide

DIPEA (0.21 g, 0.54 mmol), o-phenylene diamine (39 mg, 0.36 mmol) and HATU (89 mg, 0.23 mmol) were added to a solution of (E)-3-(2-cinnamylthiazol-4-yl)acrylic acid (50 mg, 0.18 mmol) in DCM (20 mL) and the reaction mixture was stirred overnight at room temperature under nitrogen. After completion of the reaction as indicated by HPLC, the reaction mixture was washed with saturated $NaHCO_3$ and brine. The organic layer was then dried ($Na_2SO_4$) and evaporated to give the crude product. Repeated silica gel column chromatography using a 0-10% gradient of MeOH, containing 0.1% $NH_3$ in DCM gave pure (E)-N-(2-aminophenyl)-3-(2-cinnamylthiazol-4-yl)acrylamide (26 mg) as a tan-colored solid. ES+ (M+H)+ 362. $^1$H NMR ($CD_3OD$) δ: 7.66 (s, 1H), 7.60 (d, J=15.4 Hz, 1H), 7.39-7.45 (m, 2H), 7.27-7.35 (m, 2H), 7.20 (dd, J=8.0, 1.4 Hz, 1H), 7.17-7.26 (m, 1H), 7.04 (ddd, J=8.0, 7.7, 1.4 Hz, 1H), 7.05 (d, J=15.3 Hz, 1H), 6.87 (dd, J=8.0, 1.4 Hz, 1H), 6.74 (td, J=7.7, 1.4 Hz, 1H), 6.66 (dt, J=15.9, 1.1 Hz, 1H), 6.47 (dt, J=15.9, 6.9 Hz, 1H), 3.95 (dd, J=6.9, 1.1 Hz, 2H)

Method F

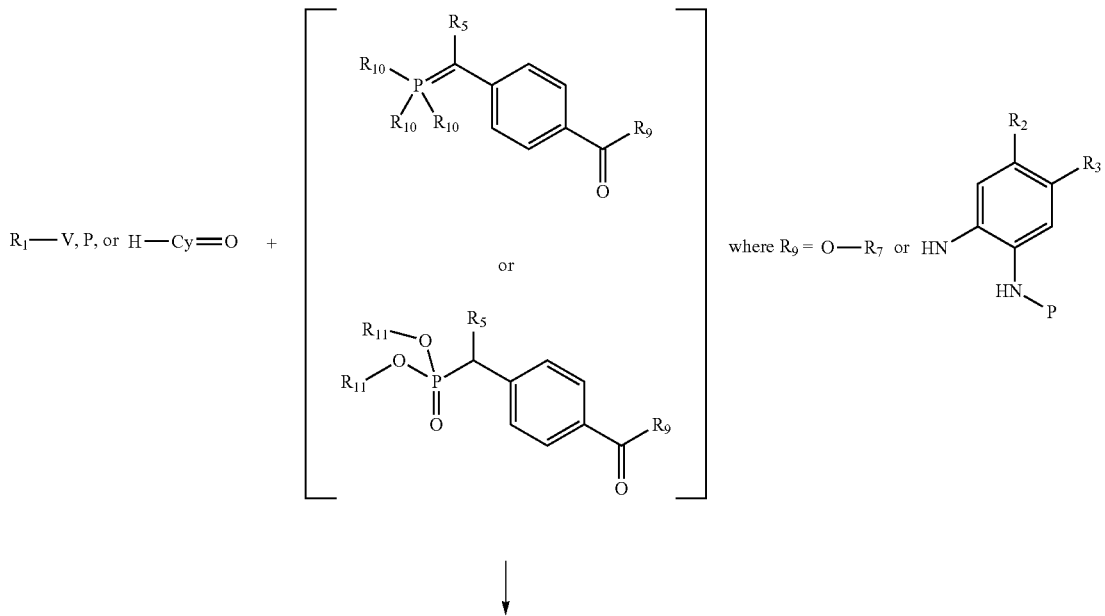

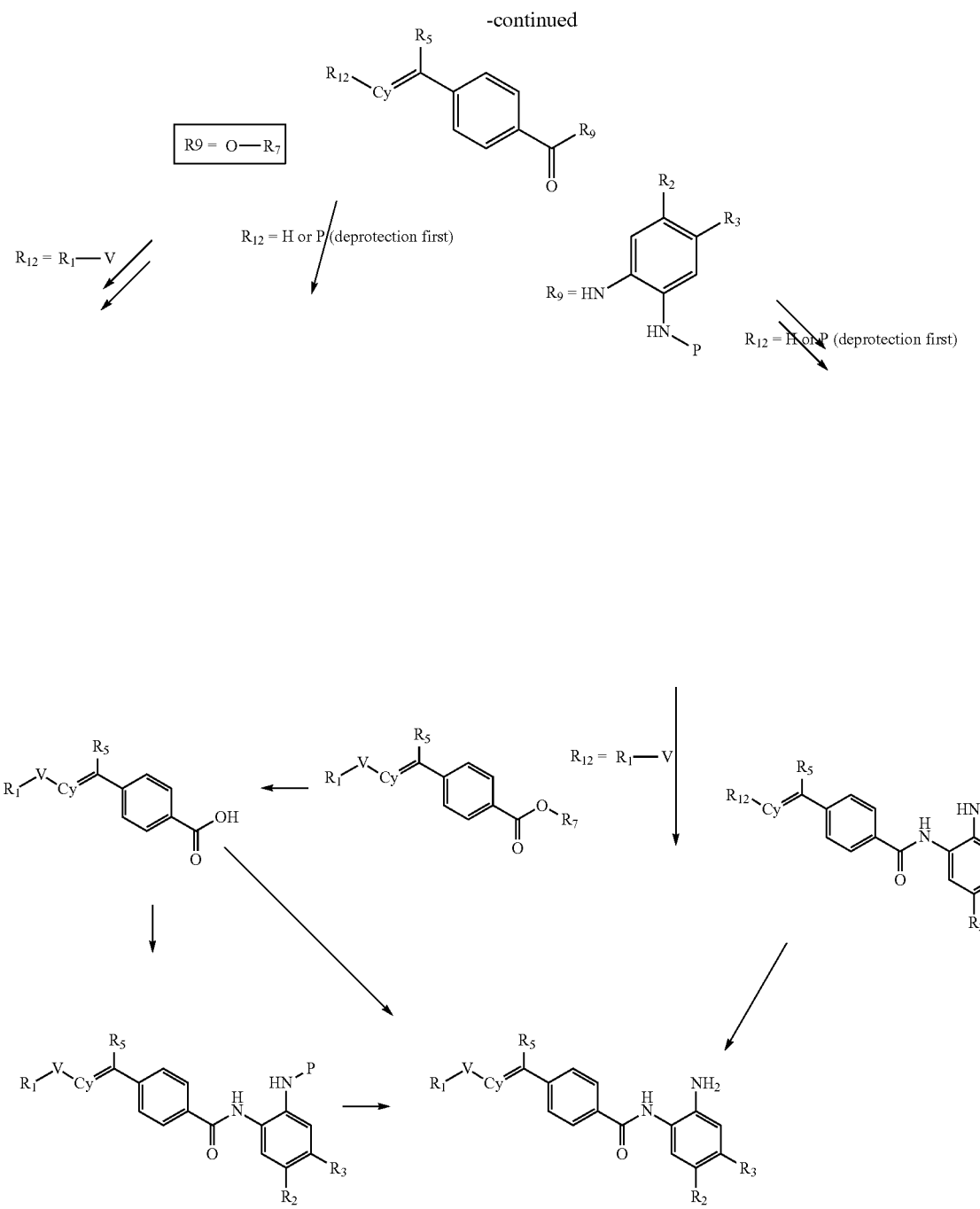

Compounds described herein, where n=0, Cy is a mono or bicyclic heterocyclic amine, can be prepared, amongst other potential approaches, by Wittig or Horner Wadsworth Emmons coupling of an N-protected mono or bicyclic amino heterocyclic ketone with a 4-α-phosphoranylidenemethyl or phosphonate-substituted or unsubstituted 4-alkyl or aralkyl benzoic acid derivative, such as, but not limited to, an ester or amide. The exocyclic alkene substituted protected heterocyclic amine derivative can be deprotected by methods well known to those skilled in the art and which can be found, for example, in P. G. M. Wuts and T. W. Greene, 2006, Greene's Protective Groups in Organic Synthesis, Fourth Edition, John Wiley & Sons, Inc., Hoboken, N.J., USA. The amine can then be derivatized by R1-V substituents using methods as diverse as, but not limited to, acylation, alkylation, reductive amination. Saponification of the benzoate ester, if present, allows for reaction of the acid with a protected or unprotected substituted or unsubstituted o-phenylenediamine. Alternatively, the protected or unprotected substituted or unsubstituted o-phenylenediamine can be introduced at an earlier step in the synthesis. Compounds of the invention, R1-V-Cy-U—Ar/Het-CO—NH—$C_6H_2R2R3$-$NH_2$, are obtained after deprotection of the amino group using methodologies well known to those skilled in the art. The double bond between Cy and U can also be reduced by hydrogenation to give saturated analogs.

Example 11: 4-((1-(((1H-indol-6-yl)methyl)azetidin-3-ylidene)methyl)-N-(2-aminophenyl)-3-chlorobenzamide F5

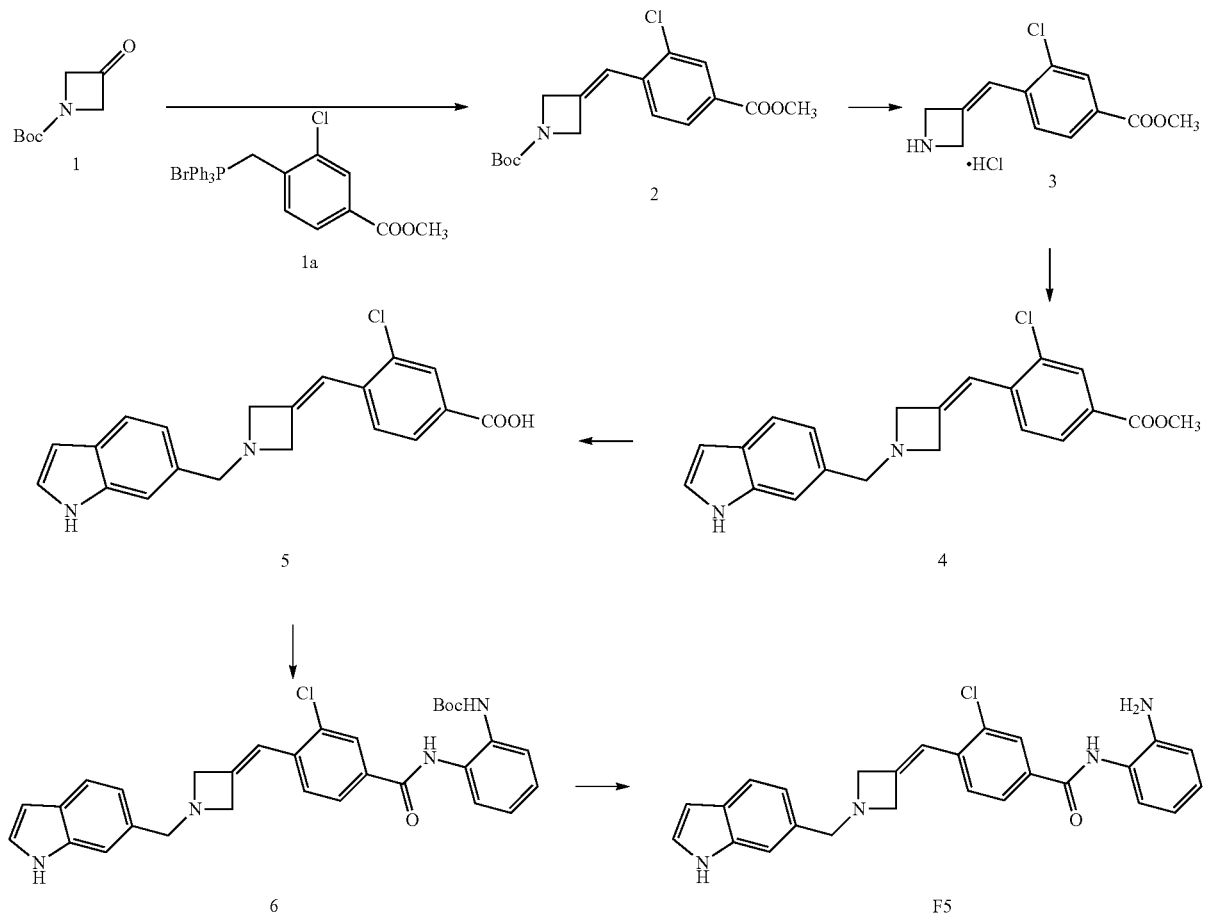

(2-chloro-4-(methoxycarbonyl)benzyl)triphenylphosphonium bromide

Methyl 3-chloro-4-methylbenzoate (2.20 g, 11.96 mmol) was dissolved in carbon tetrachloride (30 mL) and N-bromosuccinimide (2.10 g, 11.80 mmol) was added followed by a catalytic amount of benzoyl peroxide (25 mg). The reaction mixture was refluxed for 6 h. (ca. 90% conversion). After cooling to room temperature, a precipitate was filtered. The filtrate was concentrated to give crude brominated intermediate (3.20 g), which was used for the next step without further purification.

The brominated intermediate from above (3.20 g, 12.17 mmol) was dissolved in toluene (100 mL) and triphenylphosphine (6.50 g, 12.17 mmol) was added. The reaction mixture was heated at 70° C. for 6 h. Precipitation was observed right away. On completion as monitored by TLC the reaction mixture was cooled to room temperature and diluted with toluene (100 mL). The precipitate was filtered, washed with hexanes and air dried to give 4.68 g of (2-chloro-4-(methoxycarbonyl)benzyl)triphenylphosphonium bromide as a white solid. ES$^+$ (M+H)$^+$ 445.1.

tert-Butyl 3-(2-chloro-4-(ethoxycarbonyl)benzylidene)azetidine-1-carboxylate (2-Chloro-4-(methoxycarbonyl)benzyl)triphenylphosphonium bromide (1.04 g, 1.98 mmol) was dissolved in N,N-dimethylformamide (DMF, 20 mL) and the solution was cooled to 0° C. A 60% suspension of NaH in paraffin oil (80 mg, 2.00 mmol) was added and the reaction mixture was stirred at 0° C. for 15 mins. A solution of tert-butyl 3-oxoazetidine-1-carboxylate (0.32 g, 1.87 mmol) in anhydrous DMF (5 mL) was added and the reaction mixture was heated overnight at 65° C. After completion of the reaction as indicated by HPLC/MS, the cooled reaction mixture was diluted with EtOAC (20 mL) and quenched with a saturated NH$_4$Cl solution (10 mL). The organic layer was washed with water (3×20 mL) and brine (15 mL). It was then dried over anhydrous Na$_2$SO$_4$, filtered and evaporated to get the crude product. This crude was purified by silica gel column chromatography using 50-80% EtOAc in Hexanes as eluent to provide tert-butyl 3-(2-chloro-4-(methoxycarbonyl)benzylidene)azetidine-1-carboxylate (0.27 g) as a white solid. ES$^+$ (M+Na)$^+$ 360.

methyl 4-(azetidin-3-ylidenemethyl)-3-chlorobenzoate

A 4 M solution of HCl in dioxane (5 mL) was added to a solution of tert-butyl 3-(2-chloro-4-(methoxycarbonyl)benzylidene)azetidine-1-carboxylate (0.27 g, 0.66 mmol) in dioxane:DCM (1:1 v/v, 10 mL) and the mixture was stirred at room temperature for 3 h. Salt precipitation was observed. The reaction mixture was diluted with diethyl ether (20 mL). The precipitate was filtered, washed with ether and dried overnight to get the HCl salt of methyl 4-(azetidin-3-ylidenemethyl)-3-chlorobenzoate (0.12 g) as an off-white solid. ES$^+$ (M+H)$^+$ 238

Methyl 4-((1-((1H-indol-6-yl)methyl)azetidin-3-ylidene)methyl)-3-chlorobenzoate A solution of the hydrochloride salt of methyl 4-(azetidin-3-ylidenemethyl)-3-chlorobenzoate (0.20 g, 0.73 mmol) in THF:DCM (2:1) (25 mL) was neutralized by addition of triethylamine (0.14 mL, 0.88 mmol). After stirring at room temperature for 20 mins, indole-6-carboxaldehyde (0.16 g, 1.00 mmol) and sodium triacetoxyborohydride (0.50 g, 2.37 mmol) were added and the reaction mixture was heated at 50° C. overnight. It was then diluted with DCM (50 mL) and washed with saturated sodium bicarbonate (3×25 mL) and brine (1×15 mL). The organic layer was separated, dried (Na$_2$SO$_4$) and filtered. The filtrate was concentrated under vacuum to give the crude product which was purified by silica gel column chromatography using 10-40% EtOAc in hexanes as eluent. Fractions containing the pure product were pooled and evaporated to give 0.3 g of methyl 4-((1-((1H-indol-6-yl)methyl)azetidin-3-ylidene)methyl)-3-chlorobenzoate (0.30 g) as a colorless oil. ES$^+$ (M+H)$^+$ 367

4-((1-((1H-indol-6-yl)methyl)azetidin-3-ylidene)methyl)-3-chlorobenzoic acid A 2 M aqueous solution of KOH (1.5 mL) was added to a solution of methyl 4-((1-((1H-indol-6-yl)methyl)azetidin-3-ylidene)methyl)-3-chlorobenzoate (0.3 g, 0.82 mmol) in MeOH (7 mL) and the mixture was stirred at room temperature overnight. The mixture was then evaporated under reduced pressure and water (10 mL) was added to the residue. The solution was carefully acidified to pH 5 with a 3 M aqueous solution of HCl. The precipitated solid was extracted with ethyl acetate. The EtOAc layer was washed with water (2×10 mL) and brine (1×15 mL). It was dried (Na$_2$SO$_4$), filtered, and concentrated in vacuo to give 4-((1-((1H-indol-6-yl)methyl)azetidin-3-ylidene)methyl)-3-chlorobenzoic acid as a white solid (0.26 g). ES$^+$ (M+H)$^+$ 353.

tert-Butyl (2-(4-((1-((1H-indol-6-yl)methyl)azetidin-3-ylidene)methyl)-3-chlorobenzamido)phenyl)carbamate To a solution of 4-((1-((1H-indol-6-yl)methyl)azetidin-3-ylidene)methyl)-3-chlorobenzoic acid (0.26 g, 0.74 mmol) in DCM (25 mL) was added DIPEA (0.29 g, 2.22 mmol), tert-butyl-2-aminophenylcarbamate (0.27 g, 1.18 mmol) and HATU (0.37 g, 0.96 mmol). The reaction mixture was stirred overnight at room temperature under a nitrogen atmosphere. After completion of the reaction as indicated by HPLC, the mixture was washed with saturated sodium bicarbonate (2×20 mL) and brine (1×15 mL). It was dried (Na$_2$SO$_4$), filtered and evaporated to give the crude product which was purified by column chromatography (10% MeOH: 90% DCM). After evaporation of pooled fractions of pure product, tert-butyl (2-(4-((1-((1H-indol-6-yl)methyl)azetidin-3-ylidene)methyl)-3-chlorobenzamido)phenyl)carbamate (0.2 g) was isolated as an off-white solid. ES$^+$ (M+H)$^+$ 543.

4-((1-((1H-Indol-6-yl)methyl)azetidin-3-ylidene)methyl)-N-(2-aminophenyl)-3-chlorobenzamide A 4 M solution of HCl in dioxane (5 mL) was added to a solution of tert-butyl (2-(4-((1-((1H-indol-6-yl)methyl)azetidin-3-ylidene)methyl)-3-chlorobenzamido)phenyl)carbamate (0.20 g, 0.37 mmol) in dioxane (5 mL) and the mixture was stirred at room temperature for 3 h. Salt precipitation was observed. After completion of the reaction as indicated by HPLC/MS, the mixture was diluted with diethyl ether (20 mL) and the salt was filtered to give 110 mg of ca. 85% pure product. 45 mg were purified by mass-triggered reverse phase auto-purification (0.1% NH$_4$OH as additive) to give 8 mg of pure 4-((1-((1H-indol-6-yl)methyl)azetidin-3-ylidene)methyl)-N-(2-aminophenyl)-3-chlorobenzamide. $^1$H $^1$H NMR (CD$_3$OD) δ: 8.03 (d, J=1.8 Hz, 1H), 7.85 (dd, J=8.2, 1.8 Hz, 1H), 7.52 (d, J=8.1 Hz, 1H), 7.38 (s, 1H), 7.30 (d, J=8.2 Hz, 1H), 7.22 (d, J=3.2 Hz, 1H), 7.16 (dd, J=7.8, 1.3 Hz, 1H), 7.07 (ddd, J=8.1, 7.3, 1.5 Hz, 1H), 7.02 (dd, J=8.1, 1.5 Hz, 1H), 6.89 (dd, J=8.1, 1.4 Hz, 1H), 6.76 (td, J=7.7, 1.4 Hz, 1H), 6.68 (quin, J=2.3 Hz, 1H), 6.41 (dd, J=3.2, 1.0 Hz, 1H), 4.23-4.34 (m, 2H), 4.10-4.19 (m, 2H), 3.93 (s, 2H); ES$^+$ (M+H)$^+$ 443.

-continued

| | | |
|---|---|---|
| F3 | 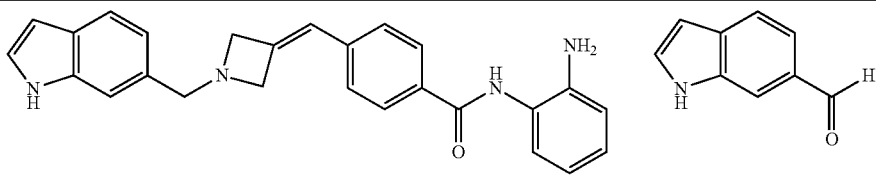 | |
| F4 | 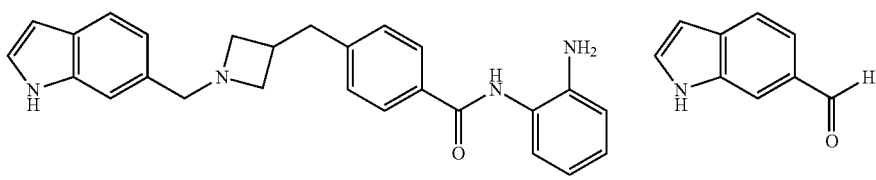 | |
| F5 | 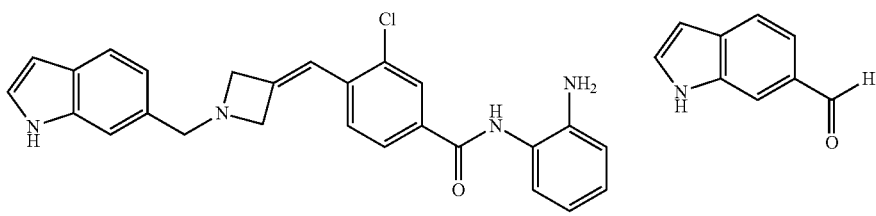 | |
| F6 | 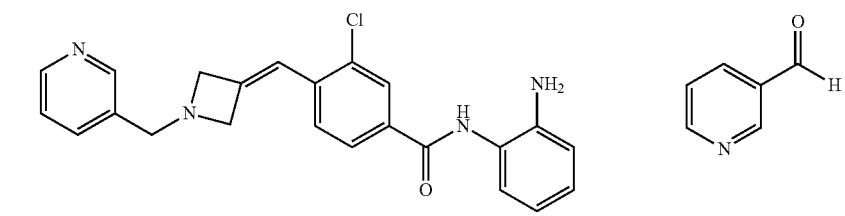 | |
| F7 | 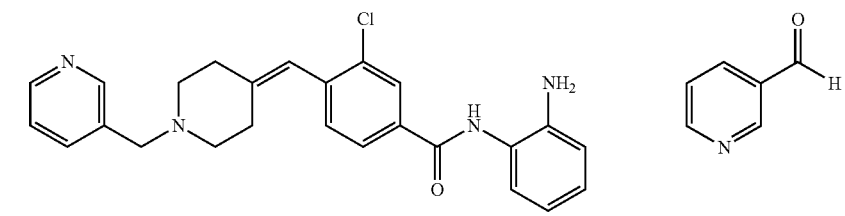 | |

| Compound | diamine | MS | NMR |
|---|---|---|---|
| F1 | 2,3-diaminobenzene (H$_2$N, NH$_2$) | ES$^+$ (M + H)$^+$ 442 | $^1$H NMR (CD$_3$OD) δ: 8.02 (d, J = 8.2 Hz, 1H), 7.21-7.52 (m, 10H), 6.85-7.15 (m, 2H), 6.50 (s, 1H), 5.14 (s, 2H), 3.44-3.71 (m, 4H), 2.32-2.61 (m, 4H) |
| F2 | 2,3-diaminobenzene (H$_2$N, NH$_2$) | ES$^+$ (M + H)$^+$ 399 | $^1$H NMR (CD$_3$OD) δ: 8.52 (d, J = 1.8 Hz, 1H), 8.45 (dd, J = 4.9, 1.6 Hz, 1H), 7.93 (d, J = 8.1 Hz, 2H), 7.86 (dt, J = 7.8, 1.9 Hz, 1H), 7.42 (ddd, J = 7.8, 4.9, 0.7 Hz, 1H), 7.33 (d, J = 8.1 Hz, 2H), 7.18 (dd, J = 7.8, 1.3 Hz, 1H), 7.07 (ddd, J = 8.0, 7.3, 1.4 Hz, 1H), 6.90 (dd, J = 8.1, 1.2 Hz, 1H), 6.76 (td, J = 7.6, 1.4 Hz, 1H), 6.39 (s, 1H), 3.60 (s, 2H), 2.40-2.65 (m, 8H) |
| F3 | 2,3-diaminobenzene (H$_2$N, NH$_2$) | ES$^+$ (M + H)$^+$ 409 | $^1$H NMR (CD$_3$OD) δ: 7.92 (d, J = 8.0 Hz, 2H), 7.53 (d, J = 8.4 Hz, 1H), 7.33-7.43 (br. s, 1H), 7.24 (d, J = 8.0 Hz, 2H), 7.22 (d, J = 3.2 Hz, 1H), 7.17 (dd, J = 7.6, 1.5 Hz, 1H), 7.07 (td, J = 7.9, 1.5 Hz, 1H), 7.03 (dd, J = |

| | | | |
|---|---|---|---|
| | | | 8.5, 1.5 Hz, 3H), 6.89 (dd, J = 8.0, 1.3 Hz, 1H), 6.76 (td, J = 7.7, 1.4 Hz, 1H), 6.42 (dd, J = 3.2, 0.9 Hz, 1H), 6.34 (quin, J = 1.8 Hz, 1H), 4.36 (br. s., 2H), 4.17 (br. s., 2H), 3.95 (s, 2H) |
| F4 | 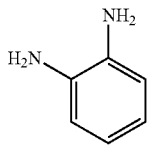 | ES+ (M + H)+ 411 | 1H NMR (CD3OD) δ: 7.91 (d, J = 8.0 Hz, 2H), 7.55 (d, J = 8.2 Hz, 1H), 7.39 (br. s., 1H), 7.32 (d, J = 8.0 Hz, 2H), 7.26 (t, J = 1.6 Hz, 1H), 7.17 (d, J = 8.2 Hz, 1H), 7.07 (td, J = 8.0, 1.4 Hz, 1H), 7.00 (dd, J = 8.2, 1.4 Hz, 1H), 6.90 (dd, J = 8.0, 1.4 Hz, 1H), 6.76 (td, J = 7.0, 1.9 Hz, 1H), 6.44 (d, J = 3.3 Hz, 1H), 4.02 (s, 2H), 3.73 (m, 2H), 3.36-3.52 (m, 2H), 2.87- .03 (m, 3H) |
| F5 | 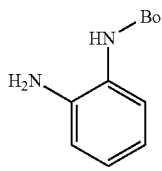 | ES+ (M + H)+ 443 | 1H NMR (CD3OD) δ: 8.03 (d, J = 1.8 Hz, 1H), 7.85 (dd, J = 8.2, 1.8 Hz, 1H), 7.52 (d, J = 8.1 Hz, 1H), 7.38 (s, 1 H), 7.30 (d, J = 8.2 Hz, 1H), 7.22 (d, J = 3.2 Hz, 1H), 7.16 (dd, J = 7.8, 1.3 Hz, 1H), 7.07 (ddd, J = 8.1, 7.3, 1.5 Hz, 1H), 7.02 (dd, J = 8.1, 1.5 Hz, 1H), 6.89 (dd, J = 8.1, 1.4 Hz, 1H), 6.76 (td, J = 7.7, 1.4 Hz, 1H), 6.68 (quin, J = 2.3 Hz, 1H), 6.41 (dd, J = 3.2, 1.0 Hz, 1H), 4.29 (q, J = 1.9 Hz, 2H), 4.16 (t, J = 1.9 Hz, 2H), 3.93 (s, 2H) |
| F6 | 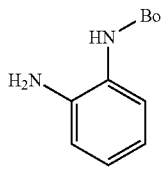 | ES+ (M + H)+ 406 | 1H NMR (CD3OD) δ: 8.56 (dd, J = 2.2, 0.7 Hz, 1H), 8.48 (dd, J = 4.8, 1.5 Hz, 1H), 8.04 (d, J = 1.6 Hz, 1H), 7.82-7.91 (m, 2H), 7.45 (ddd, J = 7.7, 4.9, 0.8 Hz, 1H), 7.30 (d, J = 8.2 Hz, 1H), 7.16 (dd, J = 8.0, 1.4 Hz, 1H), 7.08 (ddd, J = 8.1, 7.3, 1.5 Hz, 1H), 6.89 (dd, J = 8.1, 1.2 Hz, 1H), 6.76 (td, J = 7.6, 1.5 Hz, 1H), 6.70 (quin, J = 2.0 Hz, 1H), 4.31-4.41 (m, 2H), 4.17-4.27 (m, 2H), 3.95 (s, 2H) |
| F7 | 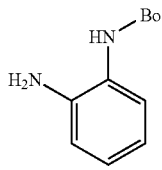 | ES+ (M + H)+ 433 | 1H NMR (CD3OD) δ: 8.53 (d, J = 1.9 Hz, 1H), 8.45 (dd, J = 4.9, 1.4 Hz, 1H), 8.04 (br. s, 1H), 7.87 (d, J = 8.0 Hz, 1H), 7.86 (d, J = 8.3 Hz, 1H), 7.43 (dd, J = 8.3, 4.9 Hz, 1H), 7.39 (d, J = 8.0 Hz, 1H), 7.18 (d, J = 8.0 Hz, 1H), 7.08 (t, J = 7.4 Hz, 1H), 6.90 (d, J = 8.0 Hz, 1H), 6.76 (t, J = 7.7 Hz, 1H), 6.37 (s, 1H), 3.62 (s, 2H), 2.62 (t, J = 5.5 Hz, 2H), 2.46-2.55 (m, 4H), 2.43 (t, J = 5.5 Hz, 2H) |

Method G

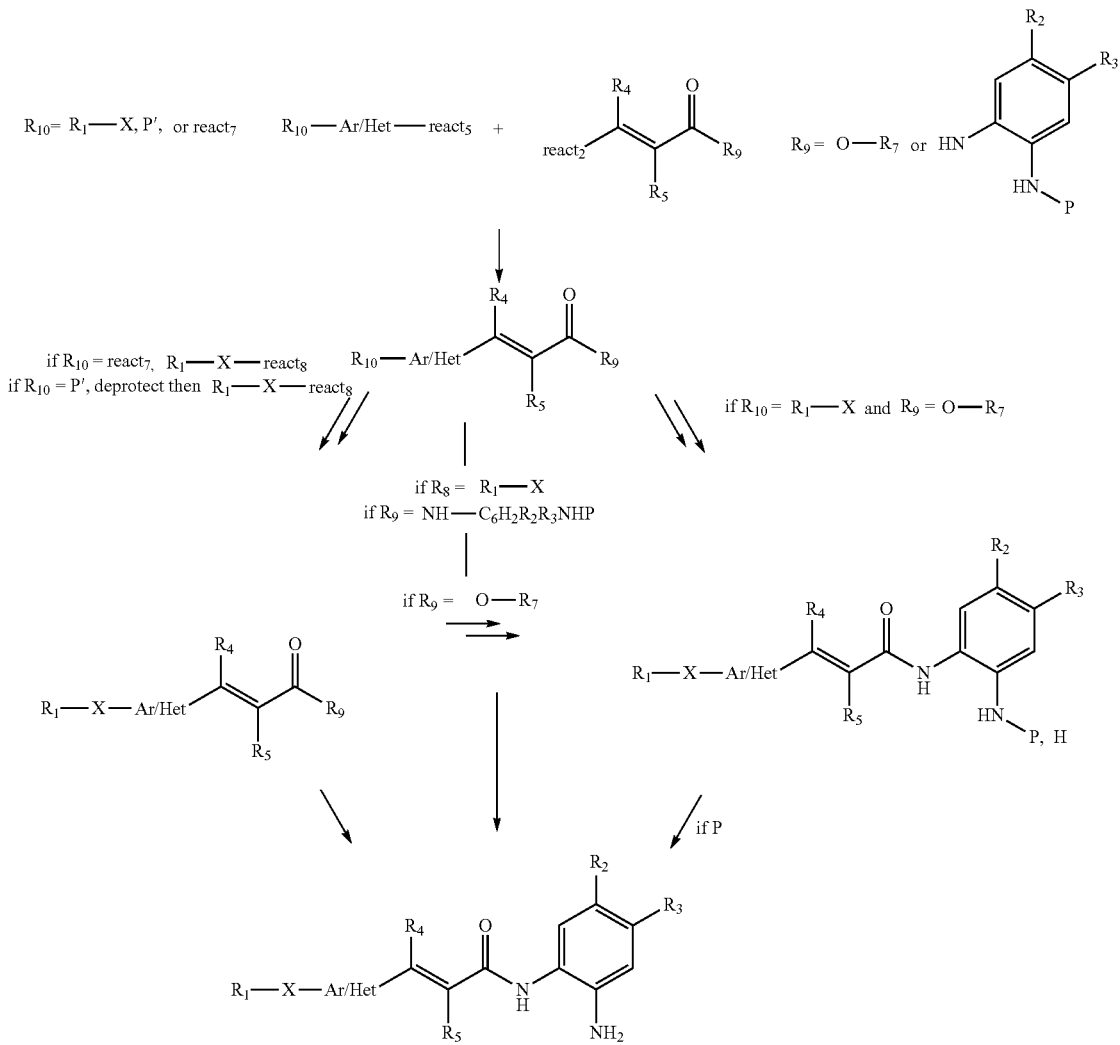

Compounds described hererin, where n=1, and R1, X, R2, R3, R4, R5, and Ar/Het are defined as defined anywhere herein, can be prepared by cross-coupling reactions well known to those skilled in the art such as the Mizoroki-Heck reaction, the Suzuki-Miyaura coupling, the Negishi coupling, and other such methods as described in, for example, Alonso D A and Najera C, Science of Synthesis, 47 (2010), 439-482 and presented in the generic scheme above, where react, (i=5-8) are reactive moieties selected as appropriate for the different coupling strategies mentioned above, and where P and P' are adequate protecting groups that can be introduced using methods well known to those skilled in the art and which are described for example in P. G. M. Wuts and T. W. Greene, 2006, Greene's Protective Groups in Organic Synthesis, Fourth Edition, John Wiley & Sons, Inc., Hoboken, N.J., USA. For example, one can prepare compounds of the invention using the Mizoroki-Heck reaction of a mono or bicyclic halogenated heterocycle, or a mono or bicyclic heterocycle triflate (react$_5$=halogen, OTf, where Tf stands for trifuloromethylsulfonyl or triflyl), which can be prepared by methods well known to those skilled in the art and detailed in, for example, Joule J A and Mills K, Heterocyclic Chemistry, Fifth Edition, John Wiley & Sons, Inc., Hoboken, N.J., USA, with an activated alkene, i.e. substituted or unsubstituted acrylic ester (react$_6$=H), to give the corresponding γ-(heterocycle)acrylate ester Ar/Het-CR4=CR5-COOR7, using protecting groups on the heterocycle when necessary. The R1-X moiety can then be added to this intermediate by synthetic methods well known to those skilled in the art, including but not limited to Heck coupling, Suzuki reaction, alkylation, acylation. Alternatively the R1-X substituent can be coupled to the mono or bicyclic heterocycle prior to the Heck reaction to give the same intermediate ester. In all cases the R1-X moiety can be built onto the scaffold in several steps using synthetic chemistry methodologies well known to those skilled in the art. The ester can then be hydrolyzed and the acid reacted with a protected or unprotected substituted or unsubstituted o-phenylenediamine to give compounds of the invention after deprotection if required using methods well known to those skilled in the art and which are described for example in P. G. M. Wuts and T. W. Greene, 2006, Greene's Protective Groups in Organic Synthesis, Fourth Edition, John Wiley & Sons, Inc., Hoboken, N.J., USA. Alternatively, the ester of the intermediate protected or unprotected γ-(heterocycle)acrylate ester Ar/Het-CR4=CR5-COOR7 described above could be hydrolyzed and the acid reacted with a protected or unprotected substituted or unsubstituted o-phenylenediamine to give compounds of the invention after deprotection if required using methods well known to those skilled in the art. Finally, the Heck coupling of the protected or unprotected halogenated mono or bicyclic heterocycle or mono or bicyclic heterocycle triflate could be performed using a substituted or unsubstituted acrylamide prepared by reaction of the corresponding substituted or unsubstituted acrylic acid, prepared by methods well known to those skilled in the art, with a protected substituted or unsubstituted o-phenylenediamine. The R1-X moiety can then be added to the intermediate amide Ar/Het-CR4=CR5-CONH (o-N(R8R9)$C_6H_2$R2R3), after deprotection of Ar/Het when required, by synthetic methods well known to those skilled in the art, including but not limited to Heck coupling, Suzuki reaction, alkylation, acylation. Alternatively the R1-X substituent can be coupled to the mono or bicyclic heterocycle prior to the Heck reaction. As mentioned above, the R1-X moiety can be built onto the molecule in several steps using synthetic chemistry methodologies well known to those skilled in the art and which can include, but are not limited to, oxidation, reduction, coupling, protection, and deprotection. Compounds of the invention can be obtained by deprotection of the ortho-amine on the amide using methods well known to those skilled in the art.

Example 12: (E)-N-(2-aminophenyl)-3-(1-((1-methylpiperidin-4-yl)methyl)-1H-pyrazol-4-yl)acrylamide G1

1-(4-iodo-1H-pyrazol-1-yl)ethanone

Acetyl chloride (38.2 mL, 1.07 equiv) and triethylamine (86 mL, 1.2 equiv) were added at 0° C. to a solution of 4-iodo-1H-pyrazole (100 g, 0.515 mol) in dichloromethane (1 L). The mixture was stirred overnight at room temperature. The reaction mixture was poured into water. The aqueous layer was extracted with dichloromethane. The combined organic layers were washed with brine, dried over anhydrous sodium sulfate ($Na_2SO_4$), and filtered. The residue obtained by concentration was purified by silica gel column chromatography (Hexane/EtOAc 20:1 to 1:1) to give N-acetyl 4-iodo-1H-pyrazole as a solid (110 g, 91%).

(E)-methyl 3-(1-acetyl-1H-pyrazol-4-yl)acrylate

A 5-L multineck flask was fitted with a mechanical stirrer, a gas inlet adapter, and a thermometer and cooled in a salt-ice bath to between −10 and −15° C. The system was purged with dry nitrogen for a few minutes. A solution of 1-(4-iodo-1H-pyrazol-1-yl)ethanone (100 g, 0.425 mol) 1.2 L of N,N-dimethylformamide (DMF) was added followed by methyl acrylate (110 g, 1.275 mol), triethylamine (64 mL, 0.458 mol), trimethyl phosphite (5.27 g, 42.5 mmol), and palladium acetate (4.76 g, 21.25 mmol). The mixture was then warmed to 110° C. under dry nitrogen atmosphere and stirred for 1 hour. LC/MS analysis of an aliquot showed only 10% product formation. Trimethyl phosphite (5.27 g, 42.5 mmol), and palladium acetate (4.76 g, 21.25 mmol) were then added to the reaction mixture. The reaction went to completion after another 1.5 h as monitored by LC/MS. The mixture was allowed to cool to room temperature and the DMF was removed under reduced pressure. The residue was stirred with 1.5 L of methylene chloride, and the suspension was filtered through a plug of silica gel. The filtrate was collected and washed with 1 L of 3% hydrochloric acid, 1 L of water, and 1 L of saturated brine. The solution was dried over magnesium sulfate and filtered. The solvent was removed under reduced pressure and the residue was purified by silica gel column chromatography (Hexane/EtOAc

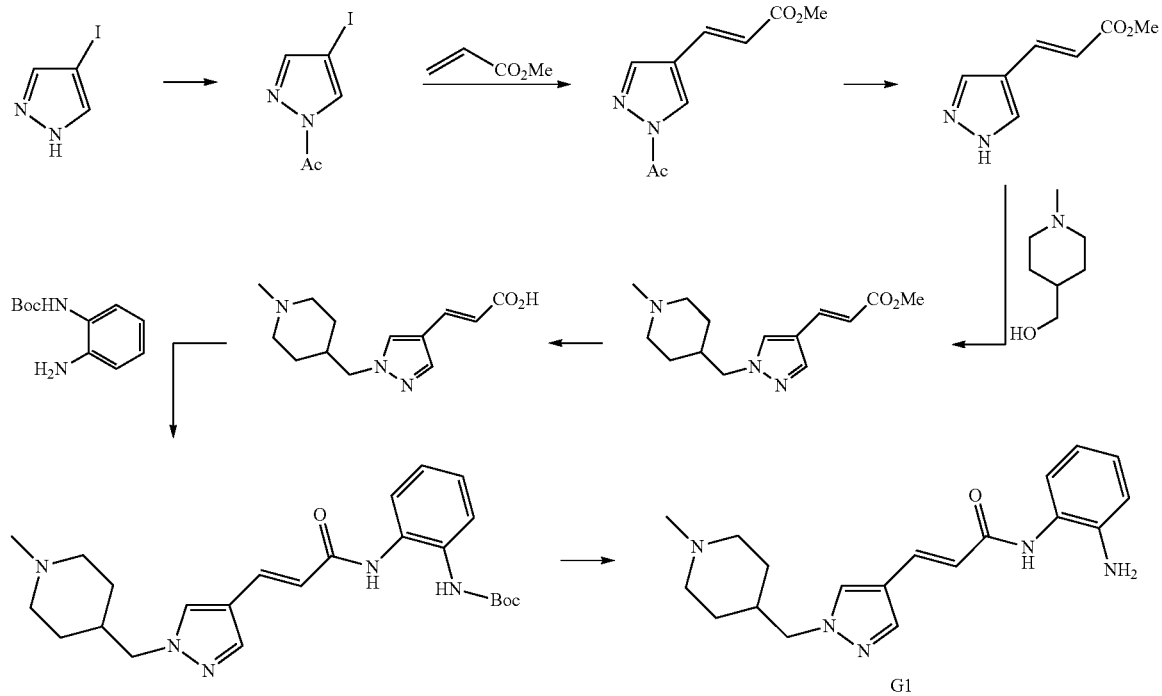

10:1 to 1:1) to give (E)-methyl 3-(1-acetyl-1H-pyrazol-4-yl)acrylate as a solid (70 g, 84%).

(E)-methyl 3-(1H-pyrazol-4-yl)acrylate

Sodium hydrogenocarbonate, NaHCO$_3$ (32 g, 1.15 equiv), was added to a suspension of protected compound, (E)-methyl 3-(1-acetyl-1H-pyrazol-4-yl)acrylate (65 g, 0.33 mol), in MeOH (600 mL). The mixture was stirred for 7 h at room temperature. The solids were then filtered and washed with dichloromethane. The filtrate was concentrated under reduced pressure and the residue was purified by silica gel column chromatography (Hexane/EtOAc 8:1 to 1:2) to give the title compound as a solid (47 g, 92%).

(E)-methyl 3-(1-((1-methylpiperidin-4-yl)methyl)-1H-pyrazol-4-yl)acrylate

Triphenylphosphine (393 mg, 1.5 mmol) and (E)-methyl 3-(1H-pyrazol-4-yl)acrylate, prepared as described above, (12 mg, 1 mmol) were added to a solution of N-methyl-4-hydroxymethyl-piperidine (165 mg, 1.25 mmol) in tetrahydrofuran (THF, 2 mL). After addition of di-tert-butyl azodicarboxylate (345 mg, 1.5 mmol), the reaction was stirred overnight at room temperature. Solvents were evaporated under reduced pressure and the residue was purified by silica gel chromatography using a gradient of Hexane in EtOAc from 1:1 to 0:100 v/v. Fractions containing product were pooled and evaporated to give 220 mg of pure material (0.84 mmol, 84%).

(E)-3-(1-((1-methylpiperidin-4-yl)methyl)-1H-pyrazol-4-yl)acrylic acid

An aqueous 3N sodium hydroxide solution (2 mL) was added to a solution of (E)-methyl 3-(1-((1-methylpiperidin-4-yl)methyl)-1H-pyrazol-4-yl)acrylate (220 mg) in MeOH (5 mL) and THF (3 mL) was added aq NaOH (3N, 2 mL) to saponify the methyl ester. Workup was performed as described in Example 12 to generate 209 mg of pure product (0.84 mmol, 100%).

(E)-N-(2-aminophenyl)-3-(1-((1-methylpiperidin-4-yl)methyl)-1H-pyrazol-4-yl)acrylamide G1

A solution of the acrylic acid prepared above (130 mg, 0.52 mmol) in DMF (2 mL) was treated with tert-butyl-(2-aminophenyl)carbamate (114 mg, 0.55 mmol), HATU (262 mg, 1.2 eq), and diisopropylethylamine (DIPEA, 0.34 mL) at 0° C. The solution was allowed to warm up. After stirring 16 h at room temperature, the reaction mixture was quenched with aqueous ammonium chloride. The mixture was diluted with water, extracted with dichloromethane. The organic phase was washed with saturated NaHCO$_3$, and brine. It was dried over Na$_2$SO$_4$, filtered, and concentrated. The residue was purified by preparative HPLC to afford pure tert-butyloxycarbonyl G1 (56 mg, 0.13 mmol, 25%).

Deprotection of the amino group was achieved as described above by overnight treatment of a solution in dioxane (1 mL) and MeOH (1 mL) with 4 M HCl in dioxane (0.5 mL). Purification by preparative HPLC gave compound G1 as a HCl salt. This product was neutralized with a solution of NaHCO$_3$ and repurified by preparative HPLC to give pure G1 (18 mg, 0.053 mmol, 41%).

$^1$H NMR (CD$_3$OD) δ: 7.97 (s, 1H), 7.84 (s, 1H), 7.55 (d, J=15.6 Hz, 1H), 7.17 (dd, J=8.0, 4.5 Hz, 1H), 7.05 (dt, 1H), 6.88 (dd, J=8.0, 4.5 Hz, 1H), 6.75 (dt, 1H), 6.60 (d, J=15.6 Hz, 1H), 4.14 (d, J=6.6 Hz, 2H), 3.6-3.4 (br, 2H), 3.1-2.9 (br, 2H), 2.84 (s, 3H); 2.22 (br, 1H), 1.95-1.80 (br, 2H), 1.7-1.45 (br, 2H); ES$^+$ (M+H)$^+$ 340.

Example 13: (E)-N-(2-aminophenyl)-3-(1-cinnamyl-3,5-dimethyl-1H-pyrazol-4-yl)acrylamide G2

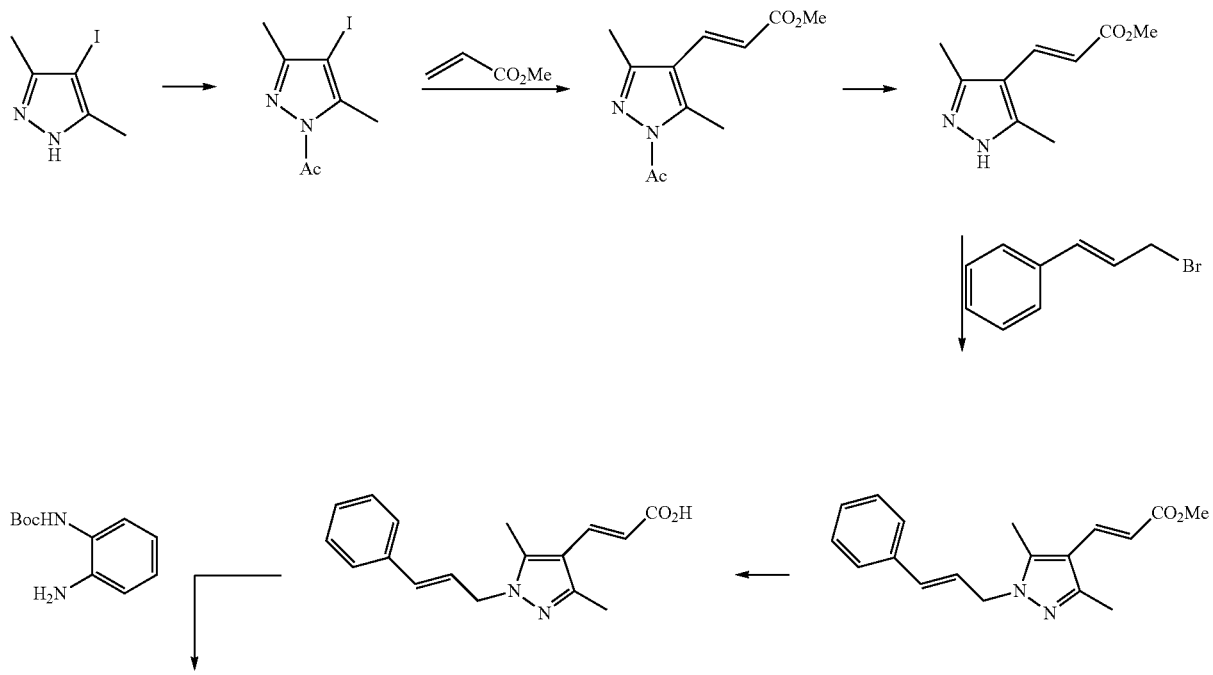

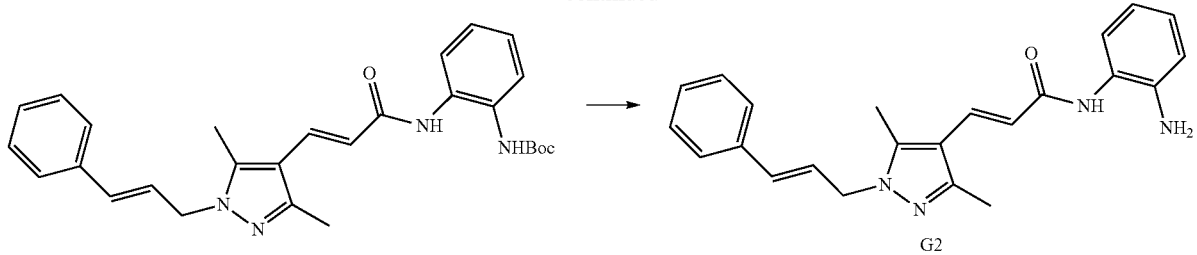

(E)-methyl 3-(3,5-dimethyl-1H-pyrazol-4-yl)acrylate

The preparation of the dimethylpyrazolyl acrylate was performed using a similar protocol as described for the synthesis of (E)-methyl 3-(1H-pyrazol-4-yl)acrylate (example 12). Thus, from 1.1 g of 4-iodo-3,5-dimethyl-1H-pyrazole (5 mmol), 440 mg of (E)-methyl 3-(3,5-dimethyl-1H-pyrazol-4-yl)acrylate were isolated (2.44 mmol, 49% over 3 steps).

(E)-methyl 3-(1-cinnamyl-3,5-dimethyl-1H-pyrazol-4-yl)acrylate (E)-methyl 3-(3,5-dimethyl-1H-pyrazol-4-yl)acrylate (360 mg, 2 mmol) was dissolved in DMF (6 mL). Sodium hydride, (NaH 60% dispersion, 80 mg, 1 equiv) was added in small portions while maintaining the temperature at 0° C. The mixture was then stirred at room temperature for 1 h. The mixture was cooled to 0° C. and cinnamyl bromide (394 mg, 1 equiv) was added. The mixture was then stirred overnight at room temperature. It was quenched with aqueous ammonium chloride, diluted with water, and extracted with EtOAc. The combined organic layers were dried over $Na_2SO_4$, filtered, and concentrated. The residue was purified by column chromatography using a gradient of hexane/EtOAc (10:1 to 0:100 v/v). Fractions containing pure product were combined and the solvents were removed under reduced pressure to yield (E)-methyl 3-(1-cinnamyl-3,5-dimethyl-1H-pyrazol-4-yl)acrylate (401 mg, 68%).

(E)-3-(1-cinnamyl-3,5-dimethyl-1H-pyrazol-4-yl) acrylic acid

The acid was obtained as described above in examples 12 and 13. Thus 44 mg of pure acid (0.16 mmol) were obtained by base hydrolysis of 124 mg (0.42 mmol) for a yield of 38%.

(E)-N-(2-aminophenyl)-3-(1-cinnamyl-3,5-dimethyl-1H-pyrazol-4-yl)acrylamide G2

Title compound G2 was obtained in two steps as described above by coupling of the acid (44 mg, 0.16 mmol) with tert-butyl (2-aminophenyl) carbamate followed by acid deprotection. Purification by preparative HPLC of the neutralized hydrochloride salt gave pure G2 (25 mg, 0.065 mmol, 42%).

$^1$H NMR (CD$_3$OD) δ: 7.65 (d, J=15.6 Hz, 1H), 7.38 (br d, J=8.4 Hz, 2H), 7.29 (br dt, J=8.4, 1.5 Hz, 2H), 7.25-7.23 (m, 1H), 7.17 (dd, J=8.0, 4.5 Hz, 1H), 7.04 (dt, J=7.8, 1.5 Hz, 1H), 6.88 (dd, J=7.8, 1.5 Hz, 1H), 6.75 (dt, J=7.8, 1.5 Hz, 1H), 6.53 (d, J=15.6 Hz, 1H), 6.4-6.3 (2 multiplets, 2H), 4.80 (d, J=4.2 Hz, 2H), 2.43 (s, 3H), 2.41 (s, 3H); ES$^+$ (M+H)$^+$ 373.

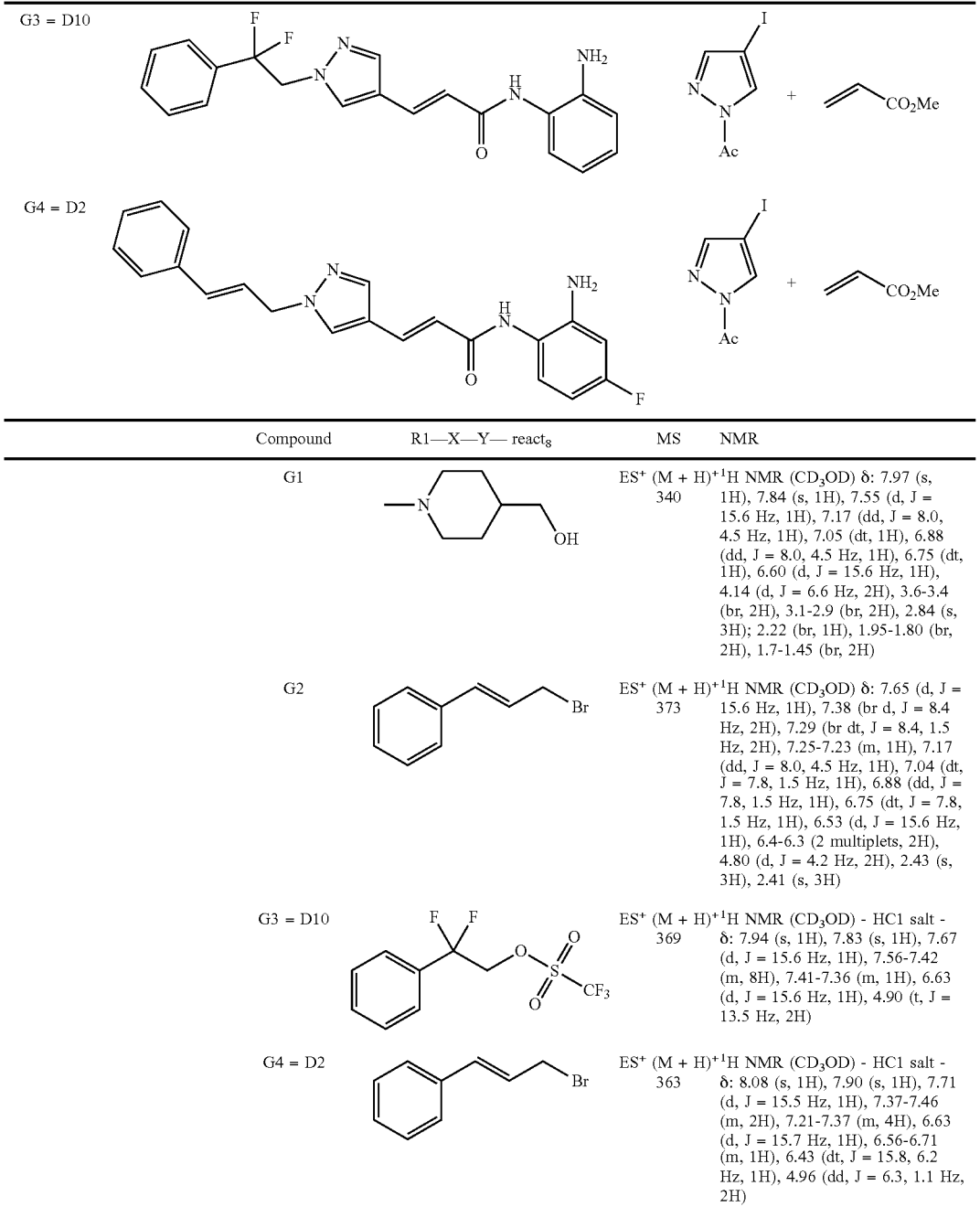

Methods
HDAC Enzyme Inhibition

The HDAC activity inhibition assay was performed as follows to determine the ability of a test compound to inhibit HDAC enzymatic activity. Serial dilutions of HDAC inhibitors were prepared in HDAC assay buffer (25 mM Tris/HCl, pH 8.0, 137 mM NaCl, 2.7 mM KCl, 1 mM $MgCl_2$, pH 8) in 96-well assay plates (Fisher scientific, #07-200-309) and were pre-incubated for 2 hours at room temperature in the presence of 125 µg/ml BSA and purified HDAC1 (BPS Bioscience, San Diego, Calif., #50051), HDAC2 (BPS Bioscience, #50053), or HDAC3/NcoR2 (BPS Bioscience, #50003) at concentrations of 1.25, 1.32, and 0.167 µg/mL, respectively. Following pre-incubation, Fluor-de-Lys™ substrate (Enzo Life Sciences, Plymouth Meeting, Pa., BML-KI104-0050) was added to a final concentration of 10 µM and plates were further incubated for 30 minutes at room temperature. The enzymatic reaction was stopped by addition of Trichostatin A (Sigma-Aldrich, St Louis, Mo., #T8552, final concentration: 100 nM) and trypsin (MP Biomedicals, Solon, Ohio, #02101179) was added to reach a final concentration of 100 µg/mL. After a 15 minute incubation at room temperature, fluorescence was recorded using a Spectramax M2 fluorometer (Molecular Devices, Sunnyvale, Calif.) with excitation at 365 nm and emission at 460 nm. IC50 values were calculated by using a sigmoidal dose-response (variable slope) equation in GraphPad Prism® 5 for Windows (GraphPad Software, La Jolla, Calif.). Results for selected compounds of the invention in the HDAC activity inhibition assay are presented in Table 1 (IC50 ranges: IA>20 µM, A<1 µM, 1<B<5 µM, 5<C<10 µM, 10<D<20 µM, ND: not determined)

TABLE 1

IC50 for inhibition of HDAC1, 2, and 3 isoforms

| compound | HDAC1 | HDAC2 | HDAC3 |
| --- | --- | --- | --- |
| D1 | A | A | A |
| D2 | B | B | A |
| D3 | A | A | A |
| D9 | A | A | A |
| B6 | A | A | A |
| B2 | A | B | A |
| B4 | A | B | A |
| B3 | A | A | A |
| D16 | B | B | A |
| B5 | A | A | A |
| A12 | B | C | A |
| D4 | A | B | A |
| D7 | A | B | A |
| D8 | A | A | A |
| D14 | A | A | A |
| D11 | A | A | A |
| D5 | A | B | A |
| D12 | A | A | A |
| D13 | A | A | A |
| D15 | A | A | A |
| D10 | A | B | A |
| D6 | B | B | A |
| A6 | C | C | A |
| A8 | A | B | A |
| A9 | B | B | A |
| A10 | B | B | A |
| E1 | B | C | A |
| A2 | C | D | A |
| A7 | B | B | A |
| C2 | IA | IA | B |
| C3 | B | B | A |
| A11 | B | B | A |
| C1 | B | B | A |
| B1 | B | C | A |
| A1 | B | C | A |
| A3 | C | C | A |
| A4 | IA | IA | B |
| A5 | D | D | A |
| E2 | A | B | A |
| F1 | A | B | A |
| F2 | A | A | A |
| F3 | A | A | A |
| F4 | A | ND | A |
| F5 | A | B | A |
| F6 | A | B | A |
| F7 | A | A | A |
| G1 | B | B | A |
| G2 | B | B | A |

Acid Stability Determination

A 100 µM solution of test compound was prepared by dilution of a 10 mM DMSO stock solution in a 0.01 M solution of HCl in deionized water. Immediately after mixing, an aliquot (100 µL) was sampled and analyzed by HPLC/UV. The area under the compound peak was determined and used as the time zero reference point. The remainder of the acid sample was incubated at 50° C. and samples were taken after 2, 4, and 24 hours of incubation. On a few occasions, samples were taken at 30 rather than 24 hours. These were analyzed by the same HPLC/UV method and the area of the peak corresponding to the test compound was measured. Percent remaining at a given time point was then calculated as the ratio of the area under the peak after incubation to that at time zero times 100. In those cases where a 30 hour time point was recorded, the percent remaining at 24 hours was obtained by interpolation of the percent remaining versus time curve assuming a unimolecular process, i.e. a monoexponential decay. Percent remaining after 24 hours incubation are presented in Table 2 below, where A corresponds to more than 60%, B is between 40 and 60%, C covers 20 to 40% and D means less than 20%.

Brain Penetration Studies

Test compounds were prepared at either 0.5 mg/ml or 5 mg/ml in 30% hydroxypropyl-β-cyclodextrin, 100 mM sodium acetate pH 5.5, 5% DMSO. C57/BL6/J mice were dosed s.c. at 5 mg/kg or 50 mg/kg, or i.v. at 5 mg/kg. Animals were euthanized at pre-dose, 5, 15, 30 min, 1, 2 and 4 hours post-dose and plasma and brain obtained. Three animals per dose per time points were used. The levels of compound in the plasma and brain were determined by standard LC/MS/MS methods. Brain/plasma ratio (BPR) was calculated as the ratio of the $C_{max}$(brain)/$C_{max}$(plasma). The results are shown in Table 2, where IA corresponds to a BPR less than 0.1, D is between 0.1 and 0.2, C is 0.2 to 0.5, B comprises 0.5 to 1 and A is greater than 1.

In-Cell Deacetylase Inhibition Assay (DAC Assay)

GM 15850 (lymphoblastoid cells line) cells were seeded in 96-well plates at an appropriate density (100,000 cells/well) in 90 µL RPMI1640 medium containing 10% v/v fetal bovine serum (FBS), 1% v/v penicillin/streptomycin, and 1% v/v L-glutamine. Compound dilutions were made in 100% DMSO followed by parallel dilution in media with 2% DMSO. 10 µl of the compound dilutions were added to the cells to achieve the desired concentrations. The final concentration of DMSO in each well was 0.2%. The cells were incubated for 4 h at 37° C. with 5% $CO_2$. After incubation, the cells were centrifuged down and the supernatant was removed. The cell pellets were washed with 100 µL phosphate-buffered saline (PBS) and then lysed with 45 µL lysis buffer (HDAC assay buffer at pH 8.0 (25 mM Tris/HCl, 137 mM NaCl, 2.7 mM KCl, 1 mM $MgCl_2$)+1% v/v Igepal CA-630). To initiate the reaction, the HDAC substrate KI-104 (Enzo Life Sciences, Farmingdale, N.Y.) was added to a final concentration of 50 µM. The reaction was stopped after 30 min incubation by addition of 50 µL developer (6 mg/mL trypsin in HDAC assay buffer). The reaction was allowed to develop for 30 min at room temperature and the fluorescence signal was detected using a fluorometer (Spectramax M2, Molecular Devices, Sunnyvale, Calif.) with excitation and emission wavelengths of 360 nm and 470 nm respectively. The data was fitted to a sigmoidal dose response equation with variable slope in GraphPad Prism 5.0 (GraphPad Software, La Jolla, Calif.) to determine IC50. Bottom and top of the curve were fixed to the average fluorescence response of control wells with no cells and cells but no compound respectively. IC50's are reported in Table 2, where A stands for IC50 less than 1 µM, B between 1 and 5 µM, C from 5 to 10 µM, D from 10 to 20 µM, and IA for IC50 above 20 µM.

Cell Proliferation Assay

HCT116 cells (5000 cells/well) in 80 µL McCoy's 5A medium containing 10% v/v FBS, 1% v/v penicillin/streptomycin and 1% v/v L-glutamine were incubated in 96-well plates with compounds at various concentrations for 72 h at 37° C. in a 5% $CO_2$ atmosphere. The compound dilutions were made in 100% DMSO followed by parallel dilutions in media. The final concentration of DMSO in each well was 0.05%. After 72 h, 20 µL of Cell titer 96 aqueous one solution (Promega Corporation, Madison, Wis.) were added to the cells and the plate was incubated at 37° C. for another 4 h. The absorbance at 490 nm was then recorded on a 96-well plate reader (Spectramax M2, Molecular Devices, Sunnyvale, Calif.). Data analysis was performed in Microsoft Excel (Microsoft Corp, Redmond, Wash.). ((O.D. sample−average O.D. positive control)/(average O.D. negative control−average O.D. positive control))*100, where O.D. is the measured absorbance, O.D. positive control is the absorbance from cells incubated with trichostatin A at 5 µM and O.D. negative control is the absorbance measured from cells incubated without any compound, was plotted against compound concentration and an IC50 was determined by graphical interpolation of the concentration required for 50% inhibition of cell growth. IC50's are presented in Table 2, where A stands for IC50 less than 5 µM, B covers the range between 5 and 10 µM, C is from 10 to 20 µM, and IA is used for IC50 greater than 20 µM.

Effect of HDAC Inhibitors on Frataxin (FXN) mRNA Expression

Blood is collected from Friedreich's ataxia patient donors into tubes containing the anti-coagulant EDTA. Primary lymphocytes are isolated using Lymphocyte Separation Medium (MP Biomedicals, Solon, Ohio) following the manufacturer's instructions and including a few modifications made by Repligen. After a final wash in Phosphate Buffered Saline (PBS), the cells are distributed into a 6-well cell culture plate in cell growth medium. The test HDAC inhibitor compound is added to cells in a dose escalating manner (usually concentrations range from 1 to 10 µM) and 0.1% DMSO is added to one well of cells as a no treatment control. Cells are incubated for 48 hours at 37° C. in a $CO_2$ incubator; cell counts are taken using a Countess automated cell counter (Invitrogen, Carlsbad, Calif.). Equivalent numbers of cells for all treatment conditions are pelleted by centrifugation and resuspended in cell lysis buffer. Total RNA is isolated from approximately $1 \times 10^6$ primary lymphocytes using a RNeasy Mini Kit (Qiagen, Valencia, Calif.), following the manufacturer's instructions and including an optional on-column DNAse digestion step. The isolation is performed either manually or using the QIAcube (Qiagen, Valencia, Calif.), an instrument that automates much of the isolation procedure. The RNA yield and concentration is determined using a Nanodrop spectrophotometer (Thermo Fisher Scientific, Waltham, Mass.) and depending on the RNA concentration, one of two protocols is used to measure frataxin (FXN) transcript levels. For samples containing at least 15 ng/µL RNA a TaqMan® Probe-based (Applied Biosystems, Carlsbad, Calif.) qRT-PCR method is used, while for samples containing less than 15 ng/µL RNA a SYBR Green qRT-PCR method is used. In the TaqMan® Probe-based method specific primer/probe pairs for FXN and GAPDH are multi-plexed in each reaction. In the SYBR Green method FXN and GAPDH are amplified in separate reactions. In both methods each RNA sample is analyzed in triplicate (preferably) or duplicate (minimally) using a one-step qRT-PCR master mix that contains all the components necessary for cDNA synthesis and PCR amplification in a single, continuous reaction. After cycling is complete, MxPro Software (Agilent Technologies, Santa Clara, Calif.) is used to analyze the collected data and determine the relative amount of FXN mRNA compared to a control sample. An adaptive baseline method is used for baseline correction whereby an algorithm automatically selects the appropriate baseline cycles for each well and each dye. An amplification-based threshold is set and the corresponding threshold cycle, or Ct, is obtained for calculating target concentration. The Ct values for each target gene (FXN and GAPDH) for each replicate series are averaged. The amount of FXN (or GAPDH) in the sample is determined as the relative quantity to the calibrator where the calibrator sample is assigned an arbitrary quantity of 1. The following equation is used: Relative quantity to the calibrator=$2^{-\Delta Ct}$ where $\Delta Ct$=(Ct_gene) unknown−(Ct_gene) calibrator, gene is either FXN or GAPDH, calibrator is a DMSO control sample, and unknown is a HDACi treated sample. The relative quantity of FXN is normalized to cell number and RNA input. Data is reported in Table 2 below, where the concentration required for a 2-fold increase in FXN mRNA is reported as A if less than 5 µM, B if between 5 and 10 µM, C if greater than 10 µM.

TABLE 2 acid stability, cell deacetylase inhibition, anti-proliferation, frataxin mRNA expression and tissue distribution assay results

| compound | acid stability | 850 DAC | Hct-116 | FXN 2x | BPR |
|---|---|---|---|---|---|
| F1 | B | IA | | | IA |
| F2 | B | D | A | A | A |
| F3 | B | B | A | A | C |
| F4 | B | B | A | A | B |
| A1 | | IA | | | B |
| A2 | B | D | IA | | B |
| A3 | | IA | | | |
| A5 | B | | | | C |
| D1 | A | B | B | A | B |
| D2 | | IA | IA | C | C |
| D3 | A | B | A | B | C |
| D10 | | C | IA | C | B |
| D4 | A | C | IA | C | C |
| D7 | B | C | A | B | B |
| D9 | A | B | B | A | B |
| D8 | | B | A | C | C |
| D5 | | C | IA | | D |
| D6 | | D | IA | C | IA |
| A6 | | IA | C | | D |
| E2 | A | D | IA | | A |
| A7 | | IA | | | B |
| A8 | B | D | | | B |
| A9 | | IA | | | |
| G1 | | B | IA | | |
| D14 | B | C | | B | |
| D11 | | B | | B | A |
| D12 | A | B | | | B |
| D13 | | B | | | IA |
| A10 | | D | | | C |
| A11 | A | | | | A |
| C1 | | IA | | | B |
| E1 | | IA | | | |
| D15 | | B | | | |
| B1 | | D | | | |
| F5 | | C | | | |
| F6 | | D | | | |
| C3 | | IA | | | |
| B6 | | C | | | |
| B2 | | C | | | |
| B4 | | D | | | C |
| B3 | | B | | | C |
| D16 | | D | | | |
| G2 | | D | IA | | |
| B5 | | C | | | C |
| A12 | | IA | | | |

Effect of Compounds on Long Term Memory for Object Recognition

C57BL/6J male mice were handled 1-2 min for 5 days and were habituated to the experimental apparatus 5 min a day for 4 consecutive days in the absence of objects. During the training trial, mice were placed in the experimental apparatus with two identical objects and were allowed to explore these objects for 3 min, which does not result in short- or long-term memory (Stefanko et al., 2009). Immediately following training, mice received subcutaneous injections of either vehicle (20% glycerol, 20% PEG 400, 20% propylene glycol, and 100 mM sodium acetate, pH 5.4), reference compound 1, RGFP109, class I HDAC inhibitor, (3, 10, 30 mg/kg), reference compound 2, RGFP136 (3, 10, 30 mg/kg), or compound D2 (3, 10, 30 mg/kg). 24-h later mice were tested for memory retention (5 min) using the object recognition memory task (ORM), in which a familiar object was replaced with a novel one. All training and testing trials were videotaped and analyzed by individuals blind to the treatment condition and the genotype of subjects. A mouse was scored as exploring an object when its head was oriented toward the object within a distance of 1 cm or when the nose was touching the object. The relative exploration time was recorded and expressed by a discrimination index [DI= (tnovel−tfamiliar)/(tnovel+tfamiliar)×100].

All doses of the compounds significantly enhanced long-term memory formation compared to vehicle-treated mice (FIG. 1). Dose dependent effects were seen with RGFP 109 and 136, but there was no effect of dose for D2. The lack of an observed dose effect for D2 is likely due to its enhanced brain penetration, such that 3 mg/kg is sufficient to produce the full behavioral effect. See FIG. 1.

Other Embodiments

A number of embodiments of the invention have been described. Nevertheless, it will be understood that various modifications may be made without departing from the spirit and scope of the invention. Accordingly, other embodiments are within the scope of the following claims.

We claim:
1. A method of treating (i) a neurological disease or disorder selected from Friedreich's ataxia, myotonic dystrophy, spinal muscular atrophy, fragile X syndrome, Huntington's disease, spinocerebellar ataxia, Kennedy's disease, amyotrophic lateral sclerosis, spinal and bulbar muscular atrophy, and Alzheimer's disease; (ii) an inflammatory disease; (iii) a memory impairment condition or (iv) a drug addiction in a subject in need thereof, the method comprising administering to the subject an effective amount of a compound having a structure of formula (I):

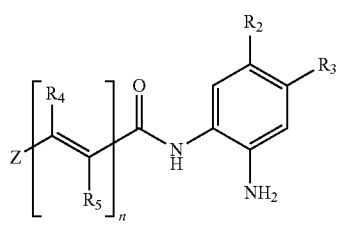

(I)

wherein n=0 or 1;
I. when n=1, Z is $R_1$—X—Ar/Het wherein:
Ar/Het is:
(i) a 5 membered heteroaryl selected from the group consisting of pyrazolyl, thiazolyl, oxazolyl, imidazolyl, thienyl, furanyl, isoxazolyl, isothiazolyl, thiadiazolyl, oxadiazolyl, and 1,2,4-triazolyl; or
(ii) a bicyclic 8-, 9-, or 10-membered heteroaryl selected from the group consisting of benzofuranyl, benzothienyl, benzothiazolyl, indolyl, indazolyl, quinolonyl, naphthyridinyl, indolizinyl, pyrrolopyrimidinyl, pyrazolopyridinyl, imidazopyridinyl, imidazopyridazinyl, triazolopyridinyl, imidazothiazolyl, imidazooxazolyl, triazolothiazolyl, and triazolooxazolyl;

X is:
(i) —Y—[C($R^a$)$_2$]$_a$-A-[C($R^b$)$_2$]$_b$—B—;
wherein:
Y is bond, $CR^c$=$CR^d$, O, $NR^e$, or S(O)$_m$;
each of A and B is, independently, a bond, O, $NR^f$, or S(O)$_m$;
a is 1-3;
b is 0-3;
m is 0-2;
each occurrence of $R^a$ and $R^b$ is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy, C1-C6 fluoroalkoxy, and cyano; or
any two $R^a$, together with the carbons to which each is attached, together form C3-C6 cycloalkyl or heterocyclyl having 3-6 ring atoms, in which one of the heterocyclyl ring atoms is selected from O, S(O)$_m$, and $NR^g$; or
one $R^a$ and one $R^b$, together with the carbons to which each is attached, form C3-C6 cycloalkyl or heterocyclyl having 3-6 ring atoms, in which one of the heterocyclyl ring atoms is selected from O, S(O)$_m$, and $NR^g$; or
any two $R^b$, together with the carbons to which each is attached, form C3-C6 cycloalkyl or heterocyclyl having 3-6 ring atoms, in which one of the ring atoms is selected from O, S(O)$_m$, and $NR^g$;
each of $R^c$ and $R^d$ is, independently, selected from H, F, OH, C1-C6 alkyl, C3-C5 cycloalkyl, $NH_2$, OCO—(C1-C6 alkyl), OCO—(C3-C5 cycloalkyl), C1-C6 alkoxy, C1-C6 fluoroalkoxy, and cyano;
or $R^c$ and $R^d$, together with the carbons to which each is attached form a C5-C7 cycloalkenyl or heterocyclenyl having 3-6 ring atoms, in which from 1-2 of the heterocyclenyl ring atoms is/are independently selected from O, S(O)$_m$, and $NR^{g'}$;
each occurrence of $R^e$, $R^f$, $R^g$ and $R^{g'}$ is independently selected from H, C1-C6 alkyl, C(=O)H, C(=O)$R^h$, C(=O)O(C1-C6 alkyl), C(=O)N($R^i$)$_2$, $SO_2$—$R^h$;
wherein $R^h$ is selected from C1-C6 alkyl, $CH_2$-(heteroaryl having 5-10 ring atoms), $CH_2$—(C6-C10 aryl), and C6-C10 aryl; and each occurrence of $R^i$ is independently selected from H, C1-C6 alkyl, $CH_2$-(heteroaryl having 5-10 ring atoms), $CH_2$—(C6-C10 aryl), and C6-C10 aryl and wherein the aryl or heteroaryl groups in $R^h$ and $R^i$ can be optionally substituted with one or more groups independently selected from the group consisting of F, C1-C6 alkyl, fluoro(C1-C6 alkyl), C3-C6 cycloalkyl, C1-C6 alkoxy, C1-C6 fluoroalkoxy, and cyano;
further wherein:
(a) when b is 0 or 1, then A and B cannot both be heteroatoms; and
(b) when A or B serves as the point of connection of X to Ar/Het, and the Ar/Het is linked to X via a nitrogen ring atom in Ar/Het, then the A or B connector cannot be a heteroatom;
or X is:
(ii) direct bond; or
(iii) C=O, C($R^j$)$_2$—C(=O), C(=O)—C($R^j$)$_2$, $SO_2$—$NR^k$, $NR^k$—$SO_2$, C(=O)$NR^k$ or $NR^k$—C(=O);
wherein:
each occurrence of $R^j$ is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy, C1-C6 fluoroalkoxy, and cyano;

or R$^j$—C—R$^j$ together form C3-C6 cycloalkyl or heterocyclyl having 3-6 ring atoms, in which one of the heterocyclyl ring atoms is selected from O, S(O)$_m$, and NR$^{j'}$;

each occurrence of R$^{j'}$ and R$^k$ is independently selected from H, C1-C6 alkyl, C(=O)H, C(=O)R$^m$, C(=O)O(C1-C6 alkyl), C(=O)N(R'')$_2$, and SO$_2$—R$^m$, wherein R$^m$ is selected from C1-C6 alkyl, CH$_2$-heteroaryl, CH$_2$-aryl, and aryl; and each occurrence of R'' is independently selected from H, C1-C6 alkyl, CH$_2$-(heteroaryl having 5-10 ring atoms), CH$_2$—(C6-C10 aryl), and C6-C10 aryl, and wherein the aryl and heteroaryl groups in R$^m$ and R'' are optionally substituted with one or more groups independently selected from F, C1-C6 alkyl, fluoro(C1-C6 alkyl), C3-C6 cycloalkyl, C1-C6 alkoxy, C1-C6 fluoroalkoxy, and cyano;

each of R$_4$ and R$_5$ is, independently, selected from H, C1-C6 alkyl and F;

R$_1$ is:
(i) hydrogen; or
(ii) C6-C10 aryl, which is optionally substituted with from 1-3 R$^o$; or
(iii) monocyclic or bicyclic heteroaryl having from 5-10 ring atoms, which is optionally substituted with from 1-3 R$^o$; wherein from 1-4 of the ring atoms is/are independently selected from O, N, N—H, N—R$^o$, and S; or
(iv) heterocyclyl having from 4-10 ring atoms, which is optionally substituted with from 1-3 R$^o$; wherein from 1-4 of the ring atoms is/are independently selected from O, N, N—H, N—R$^o$, and S; and each occurrence of R$^o$ is independently selected from the group consisting of halogen; C1-C6 alkyl; fluoro(C1-C6 alkyl); hydroxyl; hydroxy(C1-C4 alkyl); C1-C6 alkoxy; fluoro(C1-C6 alkoxy); (C1-C6 alkyl)C(O)—; (C1-C6 alkyl)NH—; (C1-C6 alkyl)$_2$N—; —N*(R$^{o'}$)$_2$, wherein R$^{o'}$—N*—R$^{o'}$ together form a saturated ring having 5 or 6 ring atoms, wherein 1 or 2 ring atoms in addition to the N* ring atom is/are optionally a heteroatom independently selected from NH, N(C1-C6 alkyl), O, or S; formyl; formyl(C1-C4 alkyl); cyano; cyano(C1-C4 alkyl); benzyl; benzyloxy; heterocyclyl-(C0-C6 alkyl), wherein the heterocyclyl portion includes 5 or 6 ring atoms, in which 1 or 2 of the ring atoms is/are independently selected from NH, N(C1-C6 alkyl), O, or S; phenyl or heteroaryl having from 5-6 ring atoms, wherein from 1-4 of the ring atoms is/are independently selected from O, N, N—H, N—R$^{o''}$, and S, wherein the phenyl or heteroaryl are each optionally substituted with from 1-3 R$^{o''}$; SO$_2$—(C1-C6 alkyl); SO—(C1-C6 alkyl); and nitro;

each occurrence of R$^{o''}$ is independently selected from the group consisting of halogen; C1-C6 alkyl; fluoro(C1-C6 alkyl); hydroxyl; hydroxy(C1-C4 alkyl); C1-C6 alkoxy; fluoro(C1-C6 alkoxy); (C1-C6 alkyl)C(O)—; (C1-C6 alkyl)NH—; (C1-C6 alkyl)$_2$N—; formyl; formyl(C1-C4 alkyl); cyano; cyano(C1-C4 alkyl); benzyl; benzyloxy; heterocyclyl-(C0-C6 alkyl), wherein the heterocyclyl portion includes 5 or 6 ring atoms, in which 1 or 2 of the ring atoms is/are independently selected from NH, N(C1-C6 alkyl), O, and S; phenyl or heteroaryl having from 5-6 ring atoms, wherein from 1-4 of the ring atoms is/are independently selected from O, N, N—H, N—(C1-C6 alkyl), and S; SO$_2$—(C1-C6 alkyl); SO—(C1-C6 alkyl); and nitro;

II. when n=0, Z is R$_1$—V-Cy-U—Ar'/Het' wherein:
Ar'/Het' is:
(i) phenyl, pyridyl, or pyrimidinyl, each of which is optionally substituted with from 1-3 R$^p$; provided that the point of connection on said phenyl, pyridyl, or pyrimidinyl to U and the point of connection on said phenyl, pyridyl, or pyrimidinyl to the amide carbonyl do not result in 1,2-relation to one another on said phenyl, pyridyl, or pyrimidinyl; wherein R$^p$ at each occurrence is, independently, selected from H, F, chloro, CH$_3$, CF$_3$, OCH$_3$, OCF$_3$, and OCHF$_2$;
(ii) a 5-membered heteroaryl selected from pyrazolyl, pyrrolyl, thiazolyl, thienyl, furanyl, imidazolyl, oxazolyl, oxadiazolyl, thiadiazolyl, isoxazolyl, isothiazolyl, each of which is optionally substituted with from 1-3 R$^p$; provided that the point of connection on said 5-membered heteroaryl to U and the point of connection on said 5-membered heteroaryl to the amide carbonyl do not result in 1,2-relation to one another on said 5-membered heteroaryl;
(iii) a 8-, 9- or 10-membered bicyclic heteroaryl selected from benzothienyl, benzofuranyl, benzothioazolyl, benzoxazolyl, indolyl, isoindolonyl, indolizinyl, pyrrolopyrimidinyl, pyrazolopyridinyl, imidazopyridinyl, imidazopyridazinyl, triazolopyridinyl, imidazothiazolyl, imidazooxazolyl, quinolinyl, and naphthyridinyl;
each of which is optionally substituted with from 1-3 R$^p$;
R$_1$ is:
(i) hydrogen; or
(ii) C6-C10 aryl, which is optionally substituted with from 1-3 R$^q$; or
(iii) monocyclic or bicyclic heteroaryl having from 5-10 ring atoms, which is optionally substituted with from 1-3 R$^q$; wherein from 1-4 of the ring atoms is/are independently selected from O, N, N—H, N—R$^q$, and S; or
(iv) heterocyclyl having from 4-10 ring atoms, which is optionally substituted with from 1-3 R$^q$; wherein from 1-4 of the ring atoms is/are independently selected from O, N, N—H, N—R$^q$, and S; and
each occurrence of R$^q$ is independently selected from the group consisting of halogen; C1-C6 alkyl; fluoro(C1-C6 alkyl); hydroxyl; hydroxy(C1-C4 alkyl); C1-C6 alkoxy; fluoro(C1-C6 alkoxy); (C1-C6 alkyl)C(O)—; (C1-C6 alkyl)NH—; (C1-C6 alkyl)$_2$N—; —N*(R$^{q'}$)$_2$, wherein R$^{q'}$—N*—R$^{q'}$ together form a saturated ring having 5 or 6 ring atoms, wherein 1 or 2 ring atoms in addition to the N* ring atom is/are optionally a heteroatom independently selected from NH, N(C1-C6 alkyl), O, or S; formyl; formyl(C1-C4 alkyl); cyano; cyano(C1-C4 alkyl); benzyl; benzyloxy; heterocyclyl-(C0-C6 alkyl), wherein the heterocyclyl portion includes 5 or 6 ring atoms, in which 1 or 2 of the ring atoms is/are independently selected from NH, N(C1-C6 alkyl), O, or S; phenyl or heteroaryl having from 5-6 ring atoms, wherein from 1-4 of the ring atoms is/are independently selected from O, N, N—H, N—R$^{q''}$, and S, wherein the phenyl or heteroaryl are each optionally substituted with from 1-3 R$^{q''}$; SO$_2$—(C1-C6 alkyl); SO—(C1-C6 alkyl); and nitro;
each occurrence of R$^{q''}$ is independently selected from the group consisting of halogen; C1-C6 alkyl; fluoro(C1-C6alkyl); hydroxyl; hydroxy(C1-C4 alkyl); C1-C6 alkoxy; fluoro(C1-C6alkoxy); (C1-C6 alkyl)C(O)—; (C1-C6 alkyl)NH—; (C1-C6 alkyl)$_2$N—; formyl; formyl(C1-C4 alkyl); cyano; cyano(C1-C4 alkyl); benzyl; benzyloxy; heterocyclyl-(C0-C6 alkyl), wherein the heterocyclyl portion includes 5 or 6 ring atoms, in which 1 or 2 of the ring atoms is/are independently selected from NH, N(C1-C6 alkyl), O, or S; phenyl or heteroaryl having from 5-6 ring atoms, wherein from 1-4 of the ring atoms is/are independently selected from O, N, N—H, N—(C1-C6 alkyl), and S; $SO_2$—(C1-C6 alkyl); SO—(C1-C6 alkyl); and nitro;

U is:
(i) =$CR^r$, wherein the carbon atom in =$CR^r$ is doubly bonded to a ring atom of Cy, thereby forming an exocyclic double bond; or
(ii) —U'—$C(R^s)_2$— or —$C(R^s)_2$—U'—;
wherein:
$R^r$ is hydrogen, F, C1-C6 alkyl, fluoro(C1-C6 alkyl), C3-C6 cycloalkyl, C1-C6 alkoxy, C1-C6 fluoroalkoxy, or cyano;
each occurrence of $R^s$ is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy, C1-C6 fluoroalkoxy, and cyano; or
$R^s$—C—$R^s$ together form C3-C6 cycloalkyl or heterocyclyl having 3-6 ring atoms, in which one of the heterocyclyl ring atoms is selected from O; $S(O)_m$, wherein m is 0-2; and $NR^U$;
each occurrence of $R^u$ is independently selected from H, C1-C6 alkyl, C(=O)H, C(=O)$R^v$, C(=O)O(C1-C6 alkyl), C(=O)N($R^w$)$_2$, and $SO_2$—$R^v$, wherein $R^v$ is selected from C1-C6 alkyl, $CH_2$-(heteroaryl having 5-10 ring atoms), $CH_2$—(C6-C10 aryl), and C6-C10 aryl; and each occurrence of $R^w$ is independently selected from H, C1-C6 alkyl, $CH_2$-(heteroaryl having 5-10 ring atoms), $CH_2$—(C6-C10 aryl), and C6-C10 aryl wherein the aryl and heteroaryl portion in $R^v$ and $R^w$ can be optionally substituted with one or more groups independently selected from F, C1-C6 alkyl, fluoro(C1-C6 alkyl), C3-C6 cycloalkyl, C1-C6 alkoxy, C1-C6 fluoroalkoxy, and cyano;
U' is a bond; O; $NR^u$; $S(O)_m$; $CH_2$; or U"—$CH_2$—; wherein U" is O; $NR^u$; or $S(O)_m$; and m is 0-2;
Cy is C4-C10 cycloalkyl or saturated heterocyclyl having 4-10 ring atoms, wherein from 1-3 heteroatoms are independently selected from N—H, $NR^{x'}$, and $S(O)_m$; m is 0-2; $R^{x'}$ is defined as $R^{q''}$; and Cy is optionally substituted with from 1-3 $R^x$; and each occurrence of $R^x$ is independently selected from F, OH, C1-C6 alkyl, fluoro(C1-C6 alkyl), C3-C6 cycloalkyl, C1-C6 alkoxy, C1-C6 fluoroalkoxy, and cyano; and wherein when the heterocyclyl contains a secondary amine as part of its structure, then:

(i) V is linked through the nitrogen of the secondary amine portion of the heterocyclyl; and
(ii) U is linked to Cy via a Cy ring carbon atom; wherein the bond between U and the Cy ring carbon is a single or double bond; and
(iii) the Cy ring carbon atom that is attached to U is not adjacent to Cy ring nitrogen atom that is attached to V;

V is:
(i) —V'—$C(R^y)_2$— or —$C(R^y)_2$—V'—; or
(ii) O, $NR^z$, or $S(O)_m$, wherein m is 0-2; or
(iii) —CH=CH—, C=O, $C(R^y)_2$—C(=O), C(=O)—$C(R^y)_2$—, —$SO_2NR^z$, $NR^zSO_2$, C(=O)$NR^z$, or $NR^zC$(=O); wherein:
each occurrence of $R^y$ is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy, C1-C6 fluoroalkoxy, and cyano; or
$R^y$—C—$R^y$ together form C3-C6 cycloalkyl or heterocyclyl having 3-6 ring atoms, in which one of the heterocyclyl ring atoms is selected from O, $S(O)_m$, and $NR^{aa}$, and m is 0-2;
each occurrence of $R^z$ and $R^{aa}$ is independently selected from H, C1-C6 alkyl, C(=O)H, C(=O)$R^v$, C(=O)O(C1-C6 alkyl), C(=O)N($R^w$)$_2$, and $SO_2$—$R^v$, wherein $R^v$ is selected from C1-C6 alkyl, $CH_2$-(heteroaryl having 5-10 ring atoms), $CH_2$—(C6-C10 aryl), and C6-C10 aryl; and each occurrence of $R^w$ is independently selected from H, C1-C6 alkyl, $CH_2$-(heteroaryl having 5-10 ring atoms), $CH_2$—(C6-C10 aryl), and C6-C10 aryl;
V' is a bond; O; $NR^u$; $S(O)_m$; —C(O)—O—$(CR^y_2)_{0-2}$—, —$(CR^y_2)_{0-2}$—O—C(O)—, $C(R^y)_2$, $C(R^y)_2$—$C(R^y)_2$; —$(R^y)_2$—V"; or V"—$C(R^y)_2$—; wherein V" is O; $NR^z$; or $S(O)_m$, and m is 0-2; wherein $R^u$ is independently selected from H, C1—C6 alkyl, C(=O)H, C(=O)$R^v$, C(=O)O(C1—C6 alkyl), C(=O)N($R^w$)$_2$ and $SO_2$—$R^v$, wherein $R^v$ is selected from C1—C6 alkyl, $CH_2$-(heteroaryl having 5-10 ring atoms), $CH_2$—(C6-C10 aryl), and C6-C10 aryl, and each occurrence of $R^y$ is independently selected from H, F, OH, C1—C6 alkyl, C3-C6 cycloalkyl, $NH_2$, OCO—(C1—C6 alkyl), OCO—(C3-C6 cycloalkyl), C1—C6 alkoxy, C1—C6 fluoroalkoxy, and cyano;
$R_2$ is selected from H, F, Cl, $CF_3$, $CF_2CF_3$, $CH_2CF_3$, $OCF_3$, $OCHF_2$, phenyl; phenyl substituted with from 1-3 substituents independently selected from F, OH, C1-C6 alkyl, fluoro(C1-C6 alkyl), C3-C6 cycloalkyl, $NH_2$, C1-C6 alkoxy, C1-C6 fluoroalkoxy, and cyano; thienyl; thiazolyl; and pyrazol-1-yl; and
$R_3$ is H, F, or Cl,
or a pharmaceutically acceptable salt thereof.

2. The method of claim 1, wherein n is 1.
3. The method of claim 2, wherein the compound of formula (I) has the following structure:

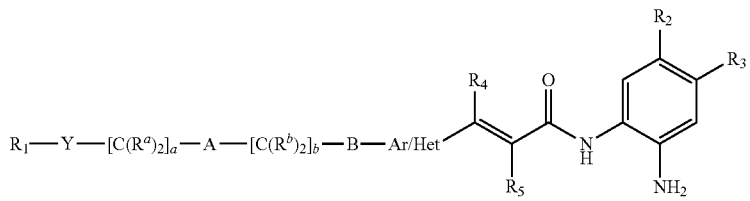

wherein
Ar/Het is selected from the group consisting of pyrazolyl, thiazolyl, oxazolyl, imidazolyl, thienyl, furanyl, isoxazolyl, isothiazolyl, thiadiazolyl, oxadiazolyl, 1,2,4-triazolyl, pyrazolopyridinyl, imidazopyridinyl, and imidazothiazolyl;
Y is bond, $CR^c$=$CR^d$, O, $NR^e$, or $S(O)_m$;

each A and B is, independently, a bond, O, $NR^f$, or $S(O)_m$;
a is 1-3;
b is 0-3;
m is 0-2;
each occurrence of $R^a$ and $R^b$ is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy, C1-C6 fluoroalkoxy, and cyano;
each of $R^c$ and $R^d$ is, independently, selected from H, F, OH, C1-C6 alkyl, C3-C5 cycloalkyl, $NH_2$, OCO—(C1-C6 alkyl), OCO—(C3-C5 cycloalkyl), C1-C6 alkoxy, C1-C6 fluoroalkoxy, and cyano;
$R^e$ is independently selected from H, C1-C6 alkyl, C(=O)H, $C(=O)R^h$, $C(=O)O(C1-C6$ alkyl), $C(=O)N(R^i)_2$, $SO_2$—$R^h$; wherein $R^h$ is selected from C1-C6 alkyl, $CH_2$-(heteroaryl having 5-10 ring atoms), $CH_2$—(C6-C10 aryl), and C6-C10 aryl; and each occurrence of $R^i$ is independently selected from H, C1-C6 alkyl, $CH_2$-(heteroaryl having 5-10 ring atoms), $CH_2$—(C6-C10 aryl), and C6-C10 aryl and the aryl or heteroaryl portion in $R^h$ and $R^i$ can be optionally substituted with one or more groups independently selected from the group consisting of F, C1-C6 alkyl, fluoro(C1-C6 alkyl), C3-C6 cycloalkyl, C1-C6 alkoxy, C1-C6 fluoroalkoxy, and cyano;
each of $R_4$ and $R_5$ is, independently, selected from H, C1-C6 alkyl and F;
$R_1$ is:
(i) hydrogen; or
(ii) C6-C10 aryl, which is optionally substituted with from 1-3 $R^o$; or
(iii) monocyclic or bicyclic heteroaryl having from 5-10 ring atoms, which is optionally substituted with from 1-3 $R^o$; wherein from 1-4 of the ring atoms is/are independently selected from O, N, N—H, N—$R^o$, and S; or
(iv) heterocyclyl having from 4-10 ring atoms, which is optionally substituted with from 1-3 $R^o$; wherein from 1-4 of the ring atoms is/are independently selected from O, N, N—H, N—$R^o$, and S; and
each occurrence of $R^o$ is independently selected from the group consisting of halogen; C1-C6 alkyl; fluoro(C1-C6 alkyl); hydroxyl; hydroxy(C1-C4 alkyl); C1-C6 alkoxy; fluoro(C1-C6 alkoxy); (C1-C6 alkyl)C(O)—; (C1-C6 alkyl)NH—; (C1-C6 alkyl)$_2$N—; formyl; formyl(C1-C4 alkyl); cyano; cyano(C1-C4 alkyl); benzyl; benzyloxy; $SO_2$—(C1-C6 alkyl); SO—(C1-C6 alkyl); and nitro;
$R_2$ is selected from H, F, Cl, $CF_3$, $CF_2CF_3$, $CH_2CF_3$, $OCF_3$, $OCHF_2$, phenyl; phenyl substituted with from 1-3 substituents independently selected from F, OH, C1-C6 alkyl, fluoro(C1-C6 alkyl), C3-C6 cycloalkyl, $NH_2$, C1-C6 alkoxy, C1-C6 fluoroalkoxy, and cyano; thienyl; thiazolyl; and pyrazol-1-yl; and
$R_3$ is H, F, or Cl;
or a pharmaceutically acceptable salt thereof.

4. The method of claim 3, wherein each occurrence of $R^a$ and $R^b$ is independently selected from H, F, and C1-C6 alkyl.

5. The method of claim 3, wherein A is a bond and/or B is a bond.

6. The method of claim 3, wherein Y is $CR^c$=$CR^d$, O, or $NR^e$.

7. The method of claim 3, wherein each of $R_4$ and $R_5$ is H.

8. The method of claim 3, wherein one of the following applies: (i) $R_2$ is F, Cl, $CF_3$, $CF_2CF_3$, $CH_2CF_3$, $OCF_3$, $OCHF_2$, phenyl; phenyl substituted with from 1-3 substituents independently selected from F, OH, C1-C6 alkyl, fluoro(C1-C6 alkyl), C3-C6 cycloalkyl, $NH_2$, C1-C6 alkoxy, C1-C6 fluoroalkoxy, and cyano; thienyl; thiazolyl; or pyrazol-1-yl, and $R_3$ is hydrogen; or (ii) $R_2$ is hydrogen, and $R_3$ is F or Cl.

9. The method of claim 3, wherein each of $R_2$ and $R_3$ is hydrogen.

10. The method of claim 3, wherein Ar/Het is pyrazolyl.

11. The method of claim 3, wherein $R_1$ is H, phenyl, or pyridyl.

12. The method of claim 1, wherein n is 0.

13. The method of claim 12, wherein Ar'/Het' is phenyl, pyridyl, or pyrimidinyl, each of which is optionally substituted with from 1-3 $R^p$; provided that the point of connection on said phenyl, pyridyl, or pyrimidinyl to U and the point of connection on said phenyl, pyridyl, or pyrimidinyl to the amide carbonyl results in a 1,4-relation to one another on said phenyl, pyridyl, or pyrimidinyl.

14. The method of claim 12, wherein Cy is a saturated heterocyclyl having 4-10 ring atoms, wherein 1-3 heteroatoms are independently selected from O, N—H, $NR^{x'}$ and $S(O)_m$; and Cy is optionally substituted with from 1-3 $R^x$; wherein each occurrence of $R^x$ is independently selected from F, OH, C1-C6 alkyl, fluoro(C1-C6 alkyl), C3-C6 cycloalkyl, C1-C6 alkoxy C1-C6 fluoroalkoxy, and cyano; and $R^{x'}$ is defined as $R^{q'}$; and m is 0-2; and wherein when the heterocyclyl contains a secondary amine as part of its structure, then:
(i) V is linked through the nitrogen of the secondary amine portion of the heterocyclyl; and
(ii) U is linked to Cy via a Cy ring carbon atom; wherein the bond between U and the Cy ring carbon is a single or double bond; and
(iii) the Cy ring carbon atom that is attached to U is not adjacent to Cy ring nitrogen atom that is attached to V.

15. The method of claim 14, wherein Cy is azetidinyl, pyrrolidinyl, piperidinyl, azepanyl, diazepanyl, isoxazolidinyl, thiazolidinonyl, imidazolidinonyl, pyrrolidinonyl, azabicyclooctyl, azabicycloheptanyl, or azabicyclohexanyl.

16. The method of claim 12, wherein $R_1$ is C6-C10 aryl, which is optionally substituted with from 1-3 $R^q$.

17. The method of claim 16, wherein $R_1$ is phenyl.

18. The method of claim 12, wherein $R_1$ is monocyclic or bicyclic heteroaryl having from 5-10 ring atoms, which is optionally substituted with from 1-3 $R^q$; wherein from 1-4 of the ring atoms is/are independently selected from O, N, N—H, N—$R^q$, and S.

19. The method of claim 18, wherein $R_1$ is pyridyl or indolyl.

20. The method of claim 12, wherein V is —V'—C($R^y$)$_2$— or —C($R^y$)$_2$—V'—, and wherein in each occurrence of $R^y$ is independently selected from H, F, OH, C1-C6 alkyl, C3-C6 cycloalkyl, $NH_2$, OCO—(C1-C6 alkyl), OCO—(C3-C6 cycloalkyl), C1-C6 alkoxy C1-C6 fluoroalkoxy, and cyano.

21. The method of claim 20, wherein V' is a bond or —($CR^y_2$)$_{0-2}$—O—C(O)—.

22. The method of claim 21, wherein U is =$CR^r$, wherein $R^r$ is hydrogen.

23. A method of treating (i) a neurological disease or disorder selected from Friedreich's ataxia, myotonic dystrophy, spinal muscular atrophy, fragile X syndrome, Huntington's disease, spinocerebellar ataxia, Kennedy's disease, amyotrophic lateral sclerosis, spinal and bulbar muscular atrophy, and Alzheimer's disease; (ii) an inflammatory disease; (iii) a memory impairment condition or (iv) a drug addiction in a subject in need thereof, the method comprising administering to the subject an effective amount of a compound selected from the group consisting of:
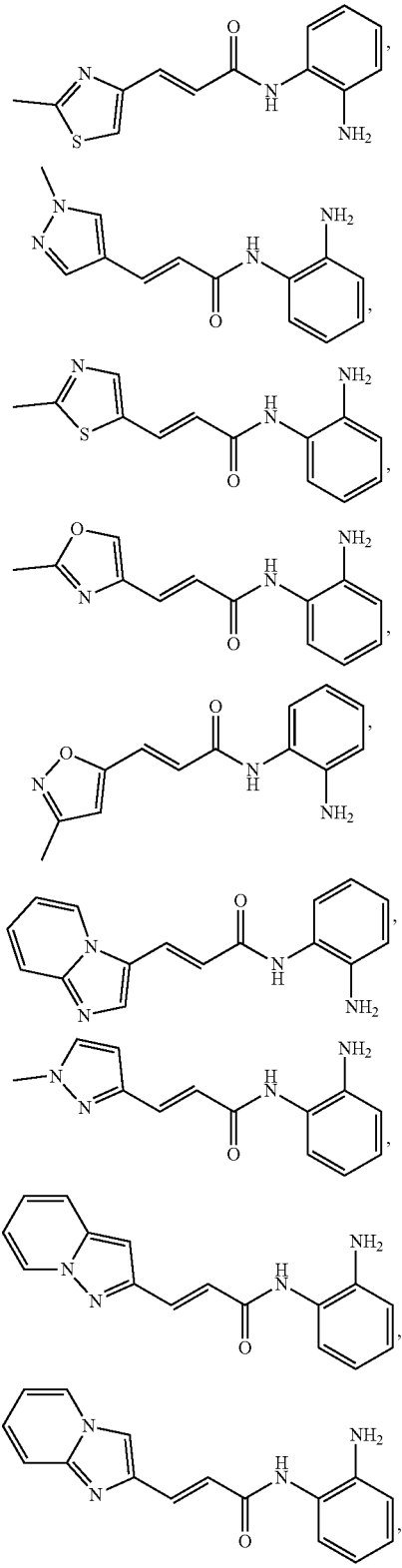
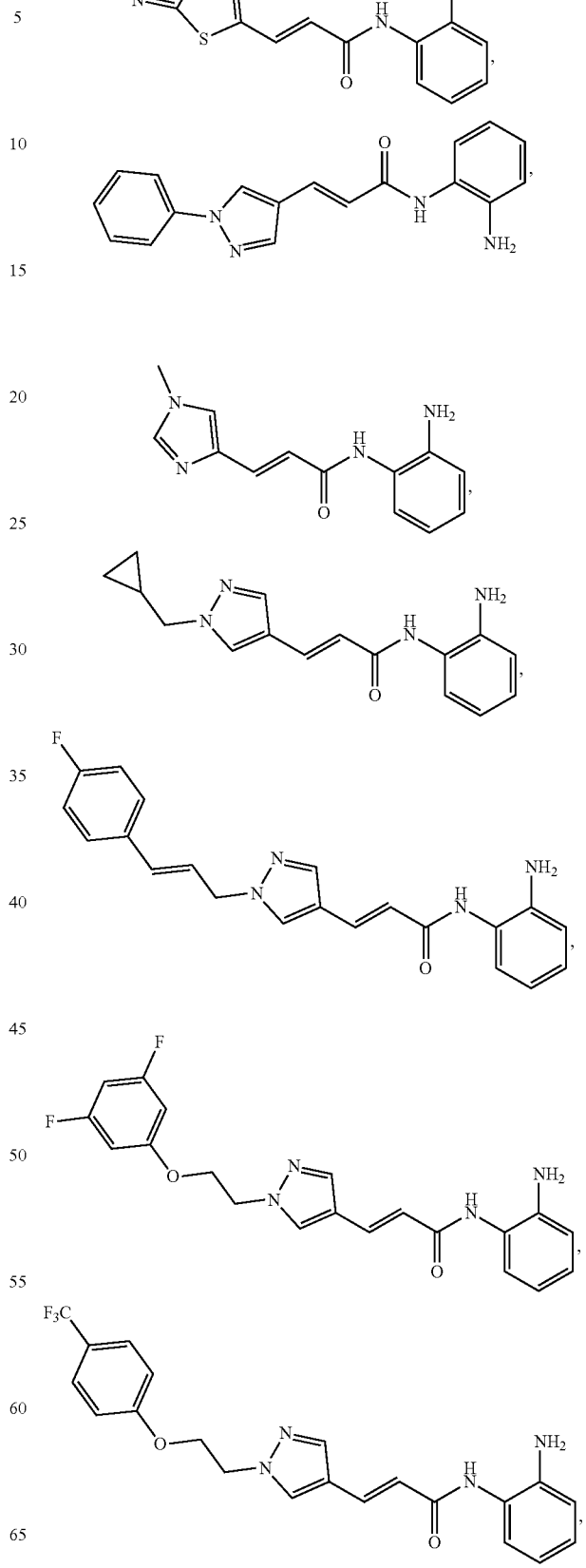

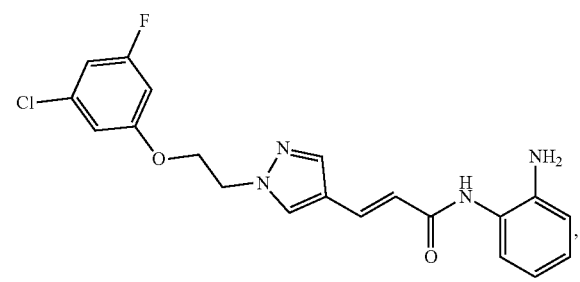
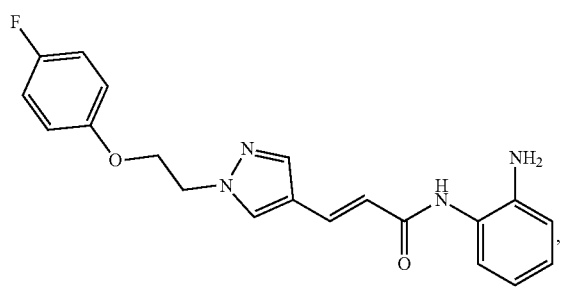
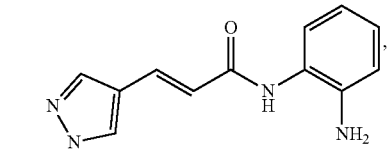
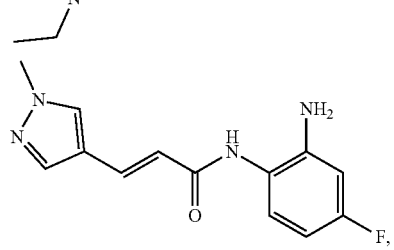
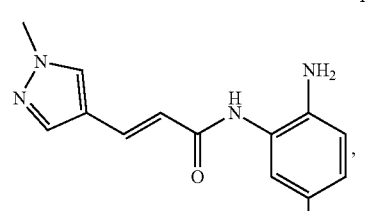
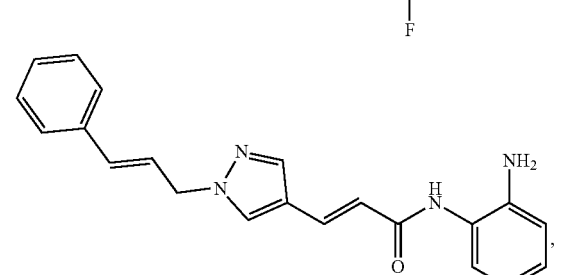
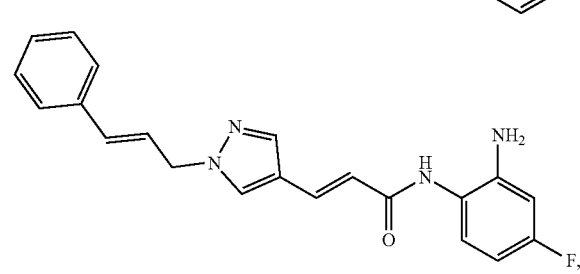
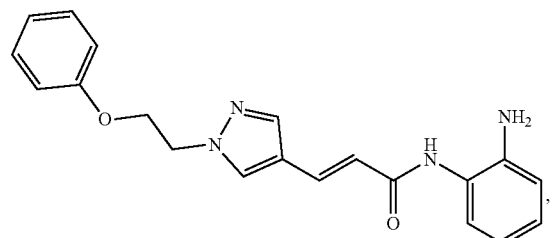
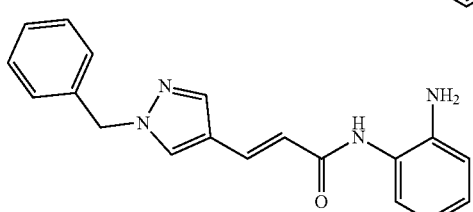
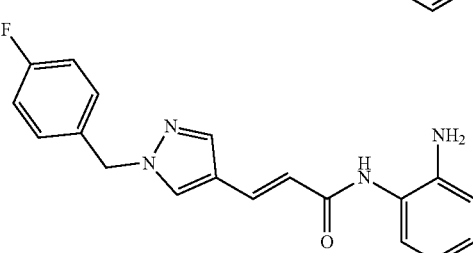
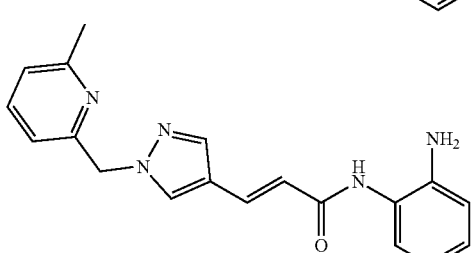
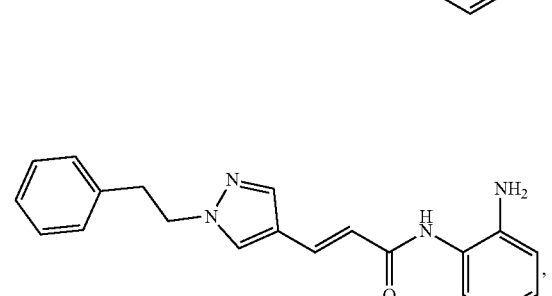
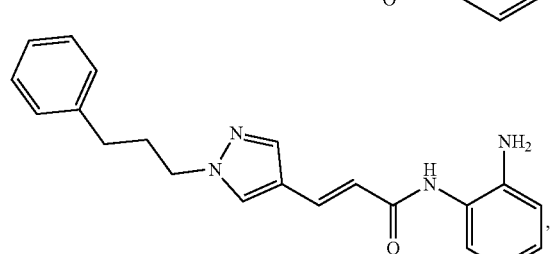
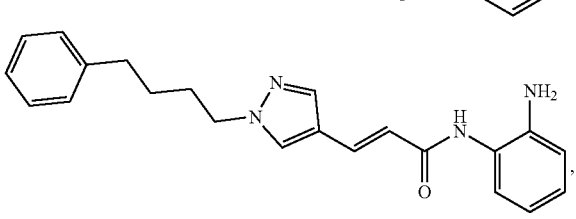

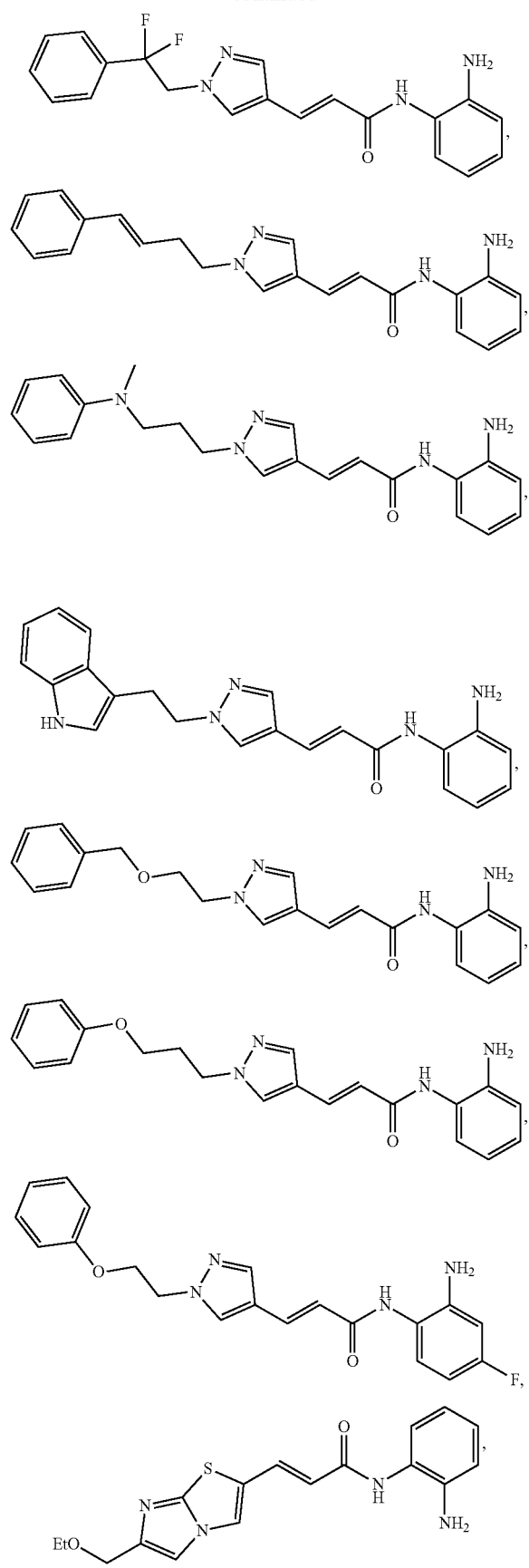
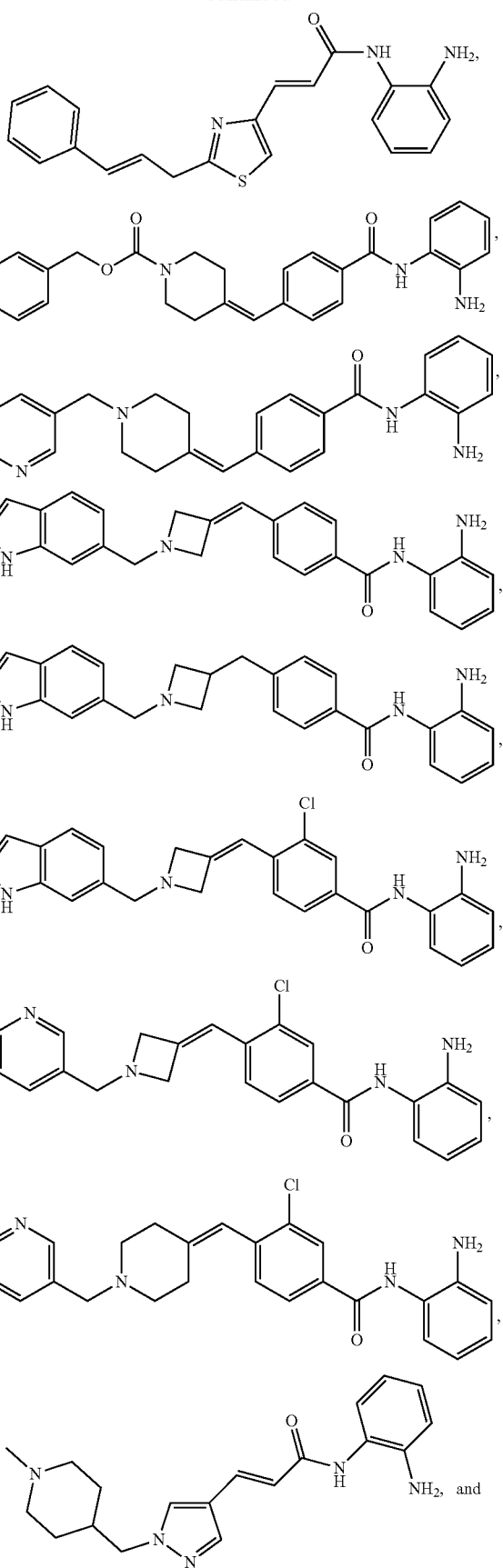

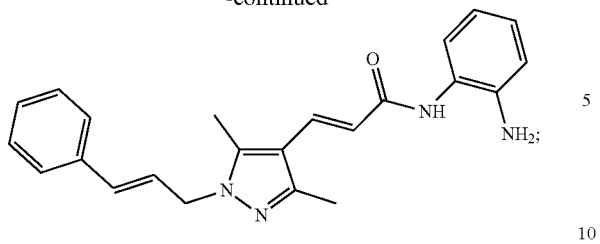
or a pharmaceutically acceptable salt thereof.
24. The method of claim 23, wherein the disease or disorder is Friedreich's ataxia.
25. The method of claim 1, wherein the disease or disorder is a neurological disease.
26. The method of claim 25, wherein the disease or disorder is Friedreich's ataxia.
* * * * *

UNITED STATES PATENT AND TRADEMARK OFFICE
CERTIFICATE OF CORRECTION

PATENT NO. : 10,059,723 B2  
APPLICATION NO. : 15/346877  
DATED : August 28, 2018  
INVENTOR(S) : Vincent Jacques et al.

Page 1 of 1

It is certified that error appears in the above-identified patent and that said Letters Patent is hereby corrected as shown below:

In the Claims

At Column 114, Line 29, "Cl—C6 alkyl," should be -- C1-C6 alkyl, --.

At Column 114, Line 30, "(Cl—C6 alkyl)," should be -- (C1-C6 alkyl), --.

At Column 114, Line 31, "Cl—C6 alkyl," should be -- C1-C6 alkyl, --.

At Column 114, Line 32, "(C6-Cl0 aryl)," should be -- (C6-C10 aryl), --.

At Column 114, Line 34, "Cl—C6 alkyl," should be -- C1-C6 alkyl, --.

At Column 114, Line 35, "(Cl—C6 alkyl)," should be -- (C1-C6 alkyl), --.

At Column 114, Line 37, "Cl—C6 alkoxy, Cl—C6" should be -- C1-C6 alkoxy, C1-C6 --.

Signed and Sealed this  
Twelfth Day of March, 2019

Andrei Iancu  
*Director of the United States Patent and Trademark Office*